US010335289B2

(12) United States Patent
Gamache et al.

(10) Patent No.: US 10,335,289 B2
(45) Date of Patent: Jul. 2, 2019

(54) STAND ALONE INTERVERTEBRAL FUSION DEVICE

(71) Applicant: DePuy Synthes Products, Inc., Raynham, MA (US)

(72) Inventors: Thomas Gamache, Raynham, MA (US); Joseph Childs, Raynham, MA (US); Derek Shaw, Raynham, MA (US); Jonathan Howe, Warwick, RI (US); Michael Gorhan, Raynham, MA (US); Shawn Stad, Raynham, MA (US); Kevin Flaherty, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/712,135

(22) Filed: May 14, 2015

(65) Prior Publication Data
US 2015/0297356 A1 Oct. 22, 2015

Related U.S. Application Data

(62) Division of application No. 13/237,233, filed on Sep. 20, 2011.
(Continued)

(51) Int. Cl.
*A61F 2/44* (2006.01)
*A61F 2/46* (2006.01)
(Continued)

(52) U.S. Cl.
CPC ........ *A61F 2/4455* (2013.01); *A61B 17/8047* (2013.01); *A61B 17/8052* (2013.01);
(Continued)

(58) Field of Classification Search
CPC .......... A61F 2/4455; A61F 2002/30504; A61F 2002/30578; A61F 2002/30604; A61F 2/30744
See application file for complete search history.

(56) References Cited

U.S. PATENT DOCUMENTS 1,636,636 A   7/1927   Humble
1,677,337 A   7/1928   Grove
(Continued)

FOREIGN PATENT DOCUMENTS

CN    201244104 Y    5/2009
DE    19710392       7/1999
(Continued)

OTHER PUBLICATIONS

Allcock, "Polyphosphazenes", The Encyclopedia of Polymer Science, vol. 13, pp. 31-41, Wiley Intersciences, John Wiley & Sons, (1988).
(Continued)

*Primary Examiner* — Jacqueline T Johanas
(74) *Attorney, Agent, or Firm* — BakerHostetler

(57) ABSTRACT

An angled fixation device, such as an angled screw. This angled fixation device may be used by the surgeon to secure a spacer to a spinal disc space. The proximal end portion of the angled fixation device is driven perpendicular to the anterior wall of the spacer, and so is parallel to the vertebral endplates and in-line with the inserter. The distal end portion of the angled fixation device is oriented at about a 45 degree angle (plus or minus 30 degrees) to the vertebral endplate it enters.

33 Claims, 50 Drawing Sheets

Related U.S. Application Data

(60) Provisional application No. 61/385,959, filed on Sep. 23, 2010, provisional application No. 61/466,309, filed on Mar. 22, 2011, provisional application No. 61/466,321, filed on Mar. 22, 2011.

(51) Int. Cl.
*A61B 17/86* (2006.01)
*A61B 17/80* (2006.01)
A61B 17/00 (2006.01)
A61F 2/30 (2006.01)
A61F 2/28 (2006.01)

(52) U.S. Cl.
CPC .......... *A61B 17/8625* (2013.01); *A61F 2/442* (2013.01); *A61F 2/447* (2013.01); *A61F 2/4465* (2013.01); *A61F 2/4611* (2013.01); A61B 17/8685 (2013.01); A61B 2017/00004 (2013.01); A61F 2/30744 (2013.01); A61F 2002/2835 (2013.01); A61F 2002/305 (2013.01); A61F 2002/3038 (2013.01); A61F 2002/30266 (2013.01); A61F 2002/30281 (2013.01); A61F 2002/30387 (2013.01); A61F 2002/30405 (2013.01); A61F 2002/30472 (2013.01); A61F 2002/30504 (2013.01); A61F 2002/30514 (2013.01); A61F 2002/30576 (2013.01); A61F 2002/30578 (2013.01); A61F 2002/30604 (2013.01); A61F 2002/30607 (2013.01); A61F 2002/30616 (2013.01); A61F 2002/30736 (2013.01); A61F 2002/30787 (2013.01); A61F 2002/30841 (2013.01); A61F 2002/30843 (2013.01); A61F 2002/30904 (2013.01); A61F 2002/4475 (2013.01); A61F 2002/4615 (2013.01); A61F 2220/0016 (2013.01); A61F 2230/0073 (2013.01); A61F 2310/00179 (2013.01); A61F 2310/00293 (2013.01)

(56) References Cited

U.S. PATENT DOCUMENTS

| | | | |
|---|---|---|---|
| 2,304,703 A | 12/1942 | O'Leary | |
| 4,105,034 A | 8/1978 | Shalaby | |
| 4,130,639 A | 12/1978 | Shalaby | |
| 4,140,678 A | 2/1979 | Shalaby | |
| 4,141,087 A | 2/1979 | Shalaby | |
| 4,205,399 A | 6/1980 | Shalaby | |
| 4,208,511 A | 6/1980 | Shalaby | |
| 4,743,256 A | 5/1988 | Brantigan | |
| 4,904,261 A | 2/1990 | Dove | |
| 4,955,908 A | 9/1990 | Frey | |
| 5,041,113 A | 8/1991 | Biedermann | |
| 5,123,926 A | 6/1992 | Pisharodi | |
| 5,147,361 A | 9/1992 | Ojima et al. | |
| 5,209,751 A | 5/1993 | Farris et al. | |
| 5,306,308 A | 4/1994 | Gross et al. | |
| 5,352,231 A | 10/1994 | Brumfield | |
| 5,391,170 A | 2/1995 | McGuire | |
| 5,395,372 A | 3/1995 | Holt | |
| 5,397,364 A | 3/1995 | Kozak | |
| 5,443,514 A | 8/1995 | Steffee | |
| 5,443,515 A | 8/1995 | Cohen | |
| 5,464,407 A | 11/1995 | McGuire | |
| 5,464,929 A | 11/1995 | Bezwada | |
| 5,499,986 A | 3/1996 | Dimarco | |
| 5,529,580 A | 6/1996 | Kusunoki et al. | |
| 5,534,031 A | 7/1996 | Matsuzaki | |
| 5,578,034 A | 11/1996 | Estes | |
| 5,591,166 A | 1/1997 | Bernhardt et al. | |
| 5,595,751 A | 1/1997 | Bezwada | |
| 5,597,579 A | 1/1997 | Bezwada | |
| 5,601,553 A | 2/1997 | Trebing et al. | |
| 5,607,687 A | 3/1997 | Bezwada | |
| 5,609,636 A | 3/1997 | Kohrs et al. | |
| 5,618,552 A | 4/1997 | Bezwada | |
| 5,620,458 A | 4/1997 | Green et al. | |
| 5,620,698 A | 4/1997 | Bezwada | |
| 5,645,598 A | 7/1997 | Brosnahan, III | |
| 5,645,850 A | 7/1997 | Bezwada | |
| 5,648,088 A | 7/1997 | Bezwada | |
| 5,662,655 A | 9/1997 | Laboureau | |
| 5,676,666 A | 10/1997 | Oxland et al. | |
| 5,698,213 A | 12/1997 | Jamiolkowski | |
| 5,700,583 A | 12/1997 | Jamiolkowski | |
| 5,713,899 A | 2/1998 | Marnay | |
| 5,716,415 A | 2/1998 | Steffee | |
| 5,755,796 A | 5/1998 | Ibo et al. | |
| 5,776,196 A | 7/1998 | Matsuzaki | |
| 5,779,707 A | 7/1998 | Bertholet | |
| 5,785,713 A | 7/1998 | Jobe | |
| 5,788,698 A | 8/1998 | Savornin | |
| 5,797,912 A | 8/1998 | Runciman | |
| 5,797,918 A | 8/1998 | McGuire | |
| 5,800,435 A | 9/1998 | Errico et al. | |
| 5,800,440 A | 9/1998 | Stead | |
| 5,859,150 A | 1/1999 | Jamiolkowski | |
| 5,888,223 A | 3/1999 | Bray, Jr. | |
| 5,904,689 A | 5/1999 | Jonjic | |
| 5,913,860 A | 6/1999 | Scholl | |
| 6,039,761 A | 3/2000 | Li et al. | |
| 6,049,026 A | 4/2000 | Muschler | |
| 6,056,749 A | 5/2000 | Kuslich | |
| 6,066,175 A | 5/2000 | Henderson | |
| 6,086,593 A | 7/2000 | Bonutti | |
| 6,093,205 A | 7/2000 | McLeod | |
| 6,099,531 A | 8/2000 | Bonutti | |
| 6,106,557 A | 8/2000 | Robioneck | |
| 6,117,174 A | 9/2000 | Nolan | |
| 6,120,503 A | 9/2000 | Michelson | |
| 6,126,689 A | 10/2000 | Brett | |
| 6,127,597 A | 10/2000 | Beyar et al. | |
| 6,139,550 A | 10/2000 | Michelson | |
| 6,156,037 A | 12/2000 | LeHuec | |
| 6,159,211 A | 12/2000 | Boriani | |
| 6,159,244 A | 12/2000 | Suddaby | |
| 6,174,311 B1 | 1/2001 | Branch et al. | |
| 6,179,875 B1 | 1/2001 | Von Strempel | |
| 6,190,414 B1 | 2/2001 | Young et al. | |
| 6,193,757 B1 | 2/2001 | Foley et al. | |
| 6,200,306 B1 | 3/2001 | Klostermeyer | |
| 6,206,922 B1 | 3/2001 | Zdeblick | |
| 6,224,602 B1 * | 5/2001 | Hayes ................ | A61B 17/8042 606/280 |
| 6,231,610 B1 | 5/2001 | Geisler | |
| 6,235,059 B1 | 5/2001 | Benezech | |
| 6,306,170 B2 | 10/2001 | Ray | |
| 6,330,845 B1 | 12/2001 | Meulink | |
| 6,336,928 B1 | 1/2002 | Guerin | |
| 6,342,055 B1 | 1/2002 | Eisermann | |
| 6,342,074 B1 | 1/2002 | Simpson | |
| 6,364,880 B1 | 4/2002 | Michelson | |
| 6,368,351 B1 | 4/2002 | Glenn et al. | |
| 6,375,462 B2 | 4/2002 | Holweg et al. | |
| 6,387,130 B1 | 5/2002 | Stone | |
| 6,395,031 B1 | 5/2002 | Foley et al. | |
| 6,406,478 B1 | 6/2002 | Kuo | |
| 6,409,766 B1 | 6/2002 | Brett | |
| 6,413,278 B1 | 7/2002 | Marchosky | |
| 6,423,063 B1 | 7/2002 | Bonutti | |
| 6,428,575 B2 | 8/2002 | Koo | |
| 6,432,106 B1 | 8/2002 | Fraser | |
| 6,447,544 B1 * | 9/2002 | Michelson .......... | A61F 2/30744 606/247 |
| 6,447,546 B1 | 9/2002 | Bramlet | |
| 6,454,769 B2 | 9/2002 | Wagner et al. | |
| 6,461,359 B1 | 10/2002 | Tribus | |
| 6,471,724 B2 | 10/2002 | Zdeblick | |
| 6,488,710 B2 | 12/2002 | Besselink | |
| 6,508,818 B2 | 1/2003 | Steiner et al. | |
| 6,558,387 B2 | 5/2003 | Errico | |

(56) References Cited

U.S. PATENT DOCUMENTS

| | | |
|---|---|---|
| 6,558,423 B1 | 5/2003 | Michelson |
| 6,562,073 B2 | 5/2003 | Foley |
| 6,565,570 B2 | 5/2003 | Sterett |
| 6,572,619 B2 | 6/2003 | Santilli |
| 6,579,290 B1 | 6/2003 | Hardcastle |
| 6,602,257 B1 | 8/2003 | Thramann |
| 6,629,998 B1 | 10/2003 | Lin |
| 6,682,563 B2 | 1/2004 | Scharf |
| 6,695,846 B2 * | 2/2004 | Richelsoph ........ A61B 17/7059 606/290 |
| 6,730,125 B1 | 5/2004 | Lin |
| 6,730,127 B2 | 5/2004 | Michelson |
| 6,733,531 B1 | 5/2004 | Trieu |
| 6,736,850 B2 | 5/2004 | Davis |
| 6,743,257 B2 | 6/2004 | Castro |
| 6,745,255 B2 | 6/2004 | Yen et al. |
| 6,761,738 B1 | 7/2004 | Boyd |
| 6,770,096 B2 | 8/2004 | Bolger |
| 6,773,437 B2 | 8/2004 | Ogilvie |
| 6,776,781 B1 | 8/2004 | Uwaydah |
| 6,805,714 B2 | 10/2004 | Sutcliffe |
| 6,808,537 B2 | 10/2004 | Michelson |
| 6,824,564 B2 | 11/2004 | Crozet |
| 6,824,565 B2 | 11/2004 | Muhanna et al. |
| 6,833,006 B2 | 12/2004 | Foley et al. |
| 6,835,208 B2 | 12/2004 | Marchosky |
| 6,837,905 B1 | 1/2005 | Lieberman |
| 6,849,093 B2 | 2/2005 | Michelson |
| 6,890,335 B2 | 5/2005 | Grabowski et al. |
| 6,890,355 B2 | 5/2005 | Michelson |
| 6,945,973 B2 | 9/2005 | Bray |
| 6,972,019 B2 | 12/2005 | Michelson |
| 6,974,479 B2 | 12/2005 | Trieu |
| 6,974,480 B2 | 12/2005 | Messerli et al. |
| 6,984,234 B2 | 1/2006 | Bray |
| 7,001,385 B2 | 2/2006 | Bonutti |
| 7,033,394 B2 | 4/2006 | Michelson |
| 7,041,135 B2 | 5/2006 | Michelson |
| 7,044,971 B2 | 5/2006 | Suddaby |
| 7,056,341 B2 | 6/2006 | Crozet |
| 7,063,491 B2 | 6/2006 | French |
| 7,070,598 B2 | 7/2006 | Lim et al. |
| 7,077,864 B2 | 7/2006 | Byrd, III |
| 7,087,055 B2 | 8/2006 | Lim et al. |
| 7,112,222 B2 | 9/2006 | Fraser |
| 7,112,223 B2 | 9/2006 | Davis |
| 7,135,024 B2 | 11/2006 | Cook |
| 7,135,043 B2 | 11/2006 | Nakahara |
| 7,163,561 B2 | 1/2007 | Michelson |
| 7,172,627 B2 | 2/2007 | Fiere |
| 7,226,482 B2 | 6/2007 | Messerli |
| 7,232,463 B2 | 6/2007 | Falahee |
| 7,232,464 B2 | 6/2007 | Mathieu |
| 7,238,203 B2 | 7/2007 | Bagga |
| 7,238,206 B2 | 7/2007 | Lange |
| 7,255,698 B2 | 8/2007 | Michelson |
| 7,276,081 B1 | 10/2007 | Coates |
| 7,288,094 B2 | 10/2007 | Lindemann |
| 7,288,095 B2 | 10/2007 | Baynham et al. |
| 7,288,114 B2 | 10/2007 | Lange |
| 7,306,605 B2 | 12/2007 | Ross |
| 7,309,358 B2 | 12/2007 | Berry |
| 7,311,734 B2 | 12/2007 | Van Hoeck |
| 7,316,714 B2 | 1/2008 | Gordon |
| 7,318,839 B2 | 1/2008 | Malberg et al. |
| 7,323,011 B2 | 1/2008 | Shepard |
| 7,326,248 B2 | 2/2008 | Michelson |
| 7,338,525 B2 | 3/2008 | Ferree |
| 7,341,587 B2 | 3/2008 | Molz |
| 7,341,590 B2 | 3/2008 | Ferree |
| 7,354,452 B2 | 4/2008 | Foley |
| 7,361,193 B2 | 4/2008 | Frey |
| 7,332,209 B2 | 10/2008 | Michelson |
| 7,435,262 B2 | 10/2008 | Michelson |
| 7,438,715 B2 | 10/2008 | Doubler |
| 7,442,209 B2 | 10/2008 | Michelson |
| 7,452,370 B2 | 11/2008 | Anderson |
| 7,491,237 B2 | 2/2009 | Randall |
| 7,527,641 B2 | 5/2009 | Suh |
| 7,593,931 B2 | 9/2009 | Louis |
| 7,594,931 B2 | 9/2009 | Louis |
| 7,594,932 B2 | 9/2009 | Aferzon |
| 7,601,171 B2 | 10/2009 | Ainsworth et al. |
| 7,601,173 B2 | 10/2009 | Messerli |
| 7,608,062 B2 | 10/2009 | Sweeney |
| 7,618,456 B2 | 11/2009 | Mathieu |
| 7,628,816 B2 | 12/2009 | Magerl |
| 7,641,665 B2 | 1/2010 | Zubok |
| 7,655,042 B2 | 2/2010 | Foley et al. |
| 7,658,766 B2 | 2/2010 | Melkent |
| 7,662,182 B2 | 2/2010 | Zubok |
| 7,674,279 B2 | 3/2010 | Johnson |
| 7,704,255 B2 | 4/2010 | Michelson |
| 7,726,002 B2 | 6/2010 | Shimp |
| 7,794,502 B2 | 9/2010 | Michelson |
| 7,815,643 B2 | 10/2010 | Johnson et al. |
| 7,815,681 B2 | 10/2010 | Ferguson |
| 7,846,206 B2 | 12/2010 | Leonard et al. |
| 7,871,441 B2 | 1/2011 | Eckman |
| 7,875,062 B2 | 1/2011 | Lindemann |
| 7,875,076 B2 | 1/2011 | Mathieu |
| 7,883,531 B2 | 2/2011 | de Coninck et al. |
| 7,887,591 B2 | 2/2011 | Aebi et al. |
| 7,887,595 B1 | 2/2011 | Pimenta |
| 7,993,403 B2 | 8/2011 | Foley et al. |
| 8,002,808 B2 | 8/2011 | Morrison et al. |
| 8,007,523 B2 | 8/2011 | Wagner |
| 8,187,329 B2 * | 5/2012 | Theofilos ................ 623/17.11 |
| 8,206,423 B2 | 6/2012 | Siegal |
| 8,216,312 B2 | 7/2012 | Gray |
| 8,236,029 B2 | 8/2012 | Siegal |
| 8,241,328 B2 | 8/2012 | Siegal |
| 8,246,622 B2 | 8/2012 | Siegal et al. |
| 8,323,342 B2 | 12/2012 | Schwab |
| 8,328,812 B2 | 12/2012 | Siegal et al. |
| 8,337,559 B2 | 12/2012 | Hansell et al. |
| 8,343,219 B2 | 1/2013 | Allain |
| 8,349,015 B2 | 1/2013 | Bae et al. |
| 8,357,200 B2 | 1/2013 | Adl |
| 8,454,694 B2 | 6/2013 | Armstrong et al. |
| 8,460,385 B1 | 6/2013 | Wensel |
| 8,460,387 B2 * | 6/2013 | Theofilos ................ 623/17.16 |
| 8,465,524 B2 | 6/2013 | Siegal |
| 8,470,044 B2 | 6/2013 | Bertholet et al. |
| 8,480,747 B2 | 7/2013 | Melkent et al. |
| 8,486,109 B2 | 7/2013 | Siegal |
| 8,491,658 B1 | 7/2013 | Etminan |
| 8,496,691 B2 * | 7/2013 | Blain ................ A61B 17/7059 606/288 |
| 8,496,708 B2 | 7/2013 | Blain |
| 8,500,783 B2 | 8/2013 | Baynham |
| 8,551,175 B1 | 10/2013 | Wensel |
| 8,562,651 B2 | 10/2013 | Metcalf et al. |
| 8,597,330 B2 | 12/2013 | Siegal |
| 8,613,772 B2 | 12/2013 | Bray et al. |
| 8,617,245 B2 | 12/2013 | Brett |
| 8,628,578 B2 | 1/2014 | Miller et al. |
| 8,641,765 B2 | 2/2014 | Muhanna |
| 8,672,977 B2 | 3/2014 | Siegal et al. |
| 8,690,928 B1 | 4/2014 | Walkenhorst et al. |
| 8,690,948 B2 | 4/2014 | Armstrong et al. |
| 8,747,443 B2 * | 6/2014 | Aferzon ............. A61B 17/8042 606/295 |
| 8,758,439 B2 | 6/2014 | Linares |
| 8,777,993 B2 | 7/2014 | Siegal et al. |
| 8,821,555 B2 | 9/2014 | Bae |
| 8,845,638 B2 | 9/2014 | Siegal et al. |
| 8,900,235 B2 | 12/2014 | Siegal |
| 8,906,098 B2 | 12/2014 | Siegal |
| 8,932,359 B2 | 1/2015 | Brett |
| 8,956,416 B2 | 2/2015 | McCarthy |
| 9,005,295 B2 | 4/2015 | Kueenzi et al. |
| 9,017,408 B2 | 4/2015 | Siegal et al. |
| 9,017,413 B2 | 4/2015 | Siegal et al. |

(56) References Cited

U.S. PATENT DOCUMENTS

| | | |
|---|---|---|
| 9,044,334 B2 | 6/2015 | Siegal et al. |
| 9,138,330 B2 | 9/2015 | Hansell et al. |
| 9,192,419 B2 * | 11/2015 | McDonough ...... A61B 17/1728 |
| 9,248,028 B2 | 2/2016 | Gamache |
| 9,254,138 B2 | 2/2016 | Siegal et al. |
| 9,265,546 B2 * | 2/2016 | Blain ................. A61B 17/7059 |
| 9,265,621 B2 | 2/2016 | Voellmicke |
| 9,278,009 B2 | 3/2016 | Bray et al. |
| 9,283,092 B2 | 3/2016 | Siegal et al. |
| 9,289,311 B1 | 3/2016 | Whipple |
| 9,364,272 B2 * | 6/2016 | Binder, Jr. ......... A61B 17/8047 |
| 9,402,735 B2 * | 8/2016 | McDonough ...... A61B 17/1728 |
| 9,402,738 B2 | 8/2016 | Niemic |
| 9,408,712 B2 | 8/2016 | Siegal et al. |
| 9,492,286 B2 | 11/2016 | Biedermann et al. |
| 9,662,225 B2 | 5/2017 | Pavento |
| 9,668,877 B2 | 6/2017 | Pavento |
| 9,848,992 B2 | 12/2017 | McDonough et al. |
| 2001/0031968 A1 | 10/2001 | Dorchak et al. |
| 2001/0032020 A1 | 10/2001 | Besselink |
| 2002/0029044 A1 | 3/2002 | Monassevitch |
| 2002/0029082 A1 | 3/2002 | Muhanna |
| 2002/0095155 A1 | 7/2002 | Michelson |
| 2002/0099376 A1 | 7/2002 | Michelson |
| 2002/0138146 A1 | 9/2002 | Jackson |
| 2002/0143328 A1 | 10/2002 | Shulzas |
| 2002/0151976 A1 | 10/2002 | Foley et al. |
| 2002/0156475 A1 | 10/2002 | Lerch et al. |
| 2003/0004576 A1 | 1/2003 | Thalgott |
| 2003/0023305 A1 | 1/2003 | McKay |
| 2003/0028197 A1 | 2/2003 | Hanson |
| 2003/0045940 A1 | 3/2003 | Eberlein et al. |
| 2003/0050645 A1 | 3/2003 | Parker |
| 2003/0083748 A1 | 5/2003 | Lee et al. |
| 2003/0100949 A1 | 5/2003 | Michelson |
| 2003/0125739 A1 | 7/2003 | Bagga |
| 2003/0130739 A1 | 7/2003 | Gerbec et al. |
| 2003/0153975 A1 | 8/2003 | Byrd |
| 2003/0158555 A1 | 8/2003 | Sanders |
| 2003/0187440 A1 * | 10/2003 | Richelsoph ........ A61B 17/7059 606/287 |
| 2003/0187506 A1 | 10/2003 | Ross |
| 2003/0195632 A1 | 10/2003 | Foley |
| 2003/0208203 A1 | 11/2003 | Lim |
| 2003/0225409 A1 | 12/2003 | Freid et al. |
| 2004/0024464 A1 | 2/2004 | Errico |
| 2004/0034430 A1 | 2/2004 | Falahee |
| 2004/0092929 A1 | 5/2004 | Zindrick |
| 2004/0106996 A1 | 6/2004 | Liu et al. |
| 2004/0111089 A1 | 6/2004 | Stevens et al. |
| 2004/0127902 A1 | 7/2004 | Suzuki |
| 2004/0127990 A1 | 7/2004 | Bartish |
| 2004/0138662 A1 | 7/2004 | Landry et al. |
| 2004/0153065 A1 | 8/2004 | Lim |
| 2004/0153072 A1 | 8/2004 | Bonutti |
| 2004/0167625 A1 | 8/2004 | Beyar et al. |
| 2004/0199253 A1 | 10/2004 | Link |
| 2004/0199254 A1 | 10/2004 | Louis |
| 2004/0210219 A1 | 10/2004 | Bray |
| 2004/0249377 A1 | 12/2004 | Kaes |
| 2004/0254644 A1 | 12/2004 | Taylor |
| 2004/0260286 A1 | 12/2004 | Ferree |
| 2005/0021144 A1 | 1/2005 | Malberg et al. |
| 2005/0033433 A1 | 2/2005 | Michelson |
| 2005/0038513 A1 | 2/2005 | Michelson |
| 2005/0043800 A1 | 2/2005 | Paul et al. |
| 2005/0065608 A1 | 3/2005 | Michelson |
| 2005/0071006 A1 | 3/2005 | Kirschman |
| 2005/0071008 A1 | 3/2005 | Kirschman |
| 2005/0085913 A1 | 4/2005 | Fraser |
| 2005/0096657 A1 | 5/2005 | Autericque et al. |
| 2005/0101960 A1 | 5/2005 | Fiere et al. |
| 2005/0113920 A1 | 5/2005 | Foley et al. |
| 2005/0143749 A1 | 6/2005 | Zalenski |
| 2005/0143827 A1 | 6/2005 | Globerman et al. |
| 2005/0149192 A1 | 7/2005 | Zucherman |
| 2005/0149193 A1 | 7/2005 | Zucherman |
| 2005/0154391 A1 | 7/2005 | Doherty et al. |
| 2005/0159813 A1 | 7/2005 | Molz |
| 2005/0177240 A1 | 8/2005 | Blain |
| 2005/0177245 A1 | 8/2005 | Leatherbury et al. |
| 2005/0182416 A1 | 8/2005 | Lim et al. |
| 2005/0209696 A1 | 9/2005 | Lin et al. |
| 2005/0251260 A1 | 11/2005 | Gerber et al. |
| 2005/0261768 A1 | 11/2005 | Trieu |
| 2005/0277938 A1 | 12/2005 | Parsons |
| 2005/0278036 A1 | 12/2005 | Leonard |
| 2006/0025860 A1 | 2/2006 | Li |
| 2006/0030851 A1 | 2/2006 | Bray |
| 2006/0058801 A1 | 3/2006 | Schlienger et al. |
| 2006/0079961 A1 | 4/2006 | Michelson |
| 2006/0085071 A1 | 4/2006 | Lechmann |
| 2006/0116768 A1 | 6/2006 | Krueger |
| 2006/0129424 A1 | 6/2006 | Chan |
| 2006/0142765 A9 | 6/2006 | Dixon |
| 2006/0142858 A1 | 6/2006 | Colleran et al. |
| 2006/0142863 A1 | 6/2006 | Fraser |
| 2006/0152863 A1 | 6/2006 | Fraser |
| 2006/0178745 A1 | 8/2006 | Bartish et al. |
| 2006/0190083 A1 | 8/2006 | Arnin |
| 2006/0211952 A1 | 9/2006 | Kennedy |
| 2006/0229609 A1 | 10/2006 | Wang |
| 2006/0229729 A1 | 10/2006 | Gordon et al. |
| 2006/0235403 A1 | 10/2006 | Blain |
| 2006/0235409 A1 | 10/2006 | Blain |
| 2006/0235411 A1 * | 10/2006 | Blain ................. A61B 17/7059 606/281 |
| 2006/0235518 A1 * | 10/2006 | Blain ................. A61B 17/7059 623/17.11 |
| 2006/0235535 A1 | 10/2006 | Ferree |
| 2006/0241597 A1 | 10/2006 | Mitchell et al. |
| 2006/0241761 A1 | 10/2006 | Gately |
| 2006/0247650 A1 | 11/2006 | Yerby et al. |
| 2006/0259147 A1 | 11/2006 | Krishna et al. |
| 2006/0265068 A1 | 11/2006 | Schwab |
| 2006/0293753 A1 | 12/2006 | Thramann |
| 2007/0049941 A1 | 3/2007 | Thramann |
| 2007/0055252 A1 | 3/2007 | Blain |
| 2007/0067035 A1 | 3/2007 | Falahee |
| 2007/0073398 A1 | 3/2007 | Fabian et al. |
| 2007/0106384 A1 | 5/2007 | Bray |
| 2007/0106388 A1 | 5/2007 | Micheslon |
| 2007/0129804 A1 | 6/2007 | Bentley |
| 2007/0149978 A1 | 6/2007 | Shezifi |
| 2007/0162138 A1 | 7/2007 | Heinz |
| 2007/0198016 A1 | 8/2007 | Zang et al. |
| 2007/0213737 A1 | 9/2007 | Schemmerhorn et al. |
| 2007/0219635 A1 | 9/2007 | Mathieu |
| 2007/0233118 A1 | 10/2007 | McLain |
| 2007/0233253 A1 | 10/2007 | Bray |
| 2007/0233254 A1 | 10/2007 | Grotz |
| 2007/0233261 A1 | 10/2007 | Lopez et al. |
| 2007/0233263 A1 | 10/2007 | Melkent |
| 2007/0250167 A1 | 10/2007 | Bray |
| 2007/0255416 A1 | 11/2007 | Melkent |
| 2007/0265631 A1 | 11/2007 | Fox |
| 2007/0270957 A1 | 11/2007 | Heinz |
| 2007/0270965 A1 | 11/2007 | Ferguson |
| 2007/0276490 A1 | 11/2007 | Mateyka |
| 2007/0282443 A1 | 12/2007 | Globerman et al. |
| 2007/0282449 A1 | 12/2007 | De Villiers et al. |
| 2007/0293948 A1 | 12/2007 | Bagga |
| 2007/0299521 A1 | 12/2007 | Glenn et al. |
| 2008/0015694 A1 | 1/2008 | Tribus |
| 2008/0027550 A1 | 1/2008 | Link |
| 2008/0033440 A1 | 2/2008 | Moskowitz |
| 2008/0051890 A1 | 2/2008 | Waugh et al. |
| 2008/0051897 A1 | 2/2008 | Lopez et al. |
| 2008/0065219 A1 | 3/2008 | Dye |
| 2008/0077247 A1 | 3/2008 | Murillo |
| 2008/0082173 A1 | 4/2008 | Delurio |
| 2008/0097436 A1 | 4/2008 | Culbert |
| 2008/0103597 A1 | 5/2008 | Lechman et al. |
| 2008/0103598 A1 | 5/2008 | Trudeau |

(56) References Cited

U.S. PATENT DOCUMENTS

| | | |
|---|---|---|
| 2008/0109005 A1 | 5/2008 | Trudeau et al. |
| 2008/0125865 A1 | 5/2008 | Abdelgany |
| 2008/0132949 A1 | 6/2008 | Aferzon |
| 2008/0132958 A1 | 6/2008 | Pech |
| 2008/0133012 A1 | 6/2008 | McGuckin |
| 2008/0133014 A1 | 6/2008 | Gately et al. |
| 2008/0161925 A1 | 7/2008 | Brittan |
| 2008/0167666 A1 | 7/2008 | Fiere |
| 2008/0172128 A1 | 7/2008 | Perez-Cruet |
| 2008/0177307 A1 | 7/2008 | Moskowitz |
| 2008/0183293 A1 | 7/2008 | Parry |
| 2008/0183294 A1 | 7/2008 | Adl |
| 2008/0221690 A1 | 9/2008 | Chaput |
| 2008/0221694 A1 | 9/2008 | Warnick et al. |
| 2008/0234822 A1 | 9/2008 | Govil |
| 2008/0243136 A1 | 10/2008 | Prager |
| 2008/0249569 A1 | 10/2008 | Waugh |
| 2008/0249575 A1 | 10/2008 | Waugh |
| 2008/0249625 A1 | 10/2008 | Waugh |
| 2008/0255620 A1 | 10/2008 | Strauss |
| 2008/0269806 A1 | 10/2008 | Zhang |
| 2008/0281425 A1 | 11/2008 | Thalgott |
| 2008/0294262 A1 | 11/2008 | Levieux |
| 2008/0300601 A1 | 12/2008 | Fabian et al. |
| 2008/0300634 A1* | 12/2008 | Gray ............... A61B 17/7059 606/280 |
| 2008/0306596 A1 | 12/2008 | Jones |
| 2008/0306598 A1 | 12/2008 | Hansen |
| 2008/0312698 A1 | 12/2008 | Bergeron |
| 2008/0312742 A1 | 12/2008 | Abernathie |
| 2008/0312743 A1 | 12/2008 | Vila et al. |
| 2009/0012529 A1 | 1/2009 | Blain et al. |
| 2009/0030421 A1 | 1/2009 | Hawkins |
| 2009/0030519 A1 | 1/2009 | Falahee |
| 2009/0030520 A1 | 1/2009 | Biedermann |
| 2009/0062921 A1 | 3/2009 | Michelson |
| 2009/0088849 A1 | 4/2009 | Armstrong |
| 2009/0099554 A1 | 4/2009 | Forster |
| 2009/0099610 A1 | 4/2009 | Johnson et al. |
| 2009/0099661 A1 | 4/2009 | Bhattacharya |
| 2009/0105771 A1 | 4/2009 | Lei |
| 2009/0105774 A1 | 4/2009 | Jones |
| 2009/0105830 A1 | 4/2009 | Jones |
| 2009/0105831 A1 | 4/2009 | Jones |
| 2009/0105832 A1 | 4/2009 | Allain et al. |
| 2009/0125028 A1 | 5/2009 | Tiesen et al. |
| 2009/0131988 A1 | 5/2009 | Bush |
| 2009/0132054 A1 | 5/2009 | Zeegers |
| 2009/0143859 A1 | 6/2009 | McClellan |
| 2009/0164020 A1 | 6/2009 | Janowski |
| 2009/0182428 A1 | 7/2009 | McClellan et al. |
| 2009/0182430 A1 | 7/2009 | Tyber |
| 2009/0192549 A1 | 7/2009 | Sanders |
| 2009/0192613 A1 | 7/2009 | Wing |
| 2009/0192614 A1 | 7/2009 | Beger et al. |
| 2009/0192615 A1 | 7/2009 | Tyber |
| 2009/0192616 A1 | 7/2009 | Zielinski |
| 2009/0198245 A1 | 8/2009 | Phan |
| 2009/0198287 A1 | 8/2009 | Chiu |
| 2009/0198339 A1 | 8/2009 | Kleiner et al. |
| 2009/0210062 A1 | 8/2009 | Thalgott |
| 2009/0210064 A1 | 8/2009 | Lechmann |
| 2009/0224023 A1 | 9/2009 | Moskowitz |
| 2009/0234364 A1 | 9/2009 | Crook |
| 2009/0248092 A1 | 10/2009 | Bellas et al. |
| 2009/0259316 A1 | 10/2009 | Ginn |
| 2009/0265007 A1 | 10/2009 | Colleran |
| 2009/0270873 A1 | 10/2009 | Fabian |
| 2009/0287251 A1 | 11/2009 | Bae |
| 2009/0306779 A1 | 12/2009 | Ahn |
| 2009/0326543 A1 | 12/2009 | Fabian |
| 2009/0326580 A1 | 12/2009 | Anderson et al. |
| 2009/0326589 A1 | 12/2009 | Lemoine et al. |
| 2010/0004747 A1 | 1/2010 | Lin |
| 2010/0016901 A1 | 1/2010 | Robinson |
| 2010/0016973 A1 | 1/2010 | De Villiers et al. |
| 2010/0023128 A1 | 1/2010 | Malberg |
| 2010/0030334 A1 | 2/2010 | Molz, IV |
| 2010/0036496 A1 | 2/2010 | Yu |
| 2010/0042159 A1 | 2/2010 | Butler |
| 2010/0057206 A1 | 3/2010 | Duffield |
| 2010/0069969 A1 | 3/2010 | Ampuero |
| 2010/0070037 A1 | 3/2010 | Parry et al. |
| 2010/0087925 A1 | 4/2010 | Kostuik |
| 2010/0106249 A1 | 4/2010 | Tyber |
| 2010/0137987 A1 | 6/2010 | Diao et al. |
| 2010/0145457 A1 | 6/2010 | Felt |
| 2010/0145459 A1 | 6/2010 | McDonough |
| 2010/0145460 A1 | 6/2010 | McDonough |
| 2010/0179656 A1 | 7/2010 | Theofilos |
| 2010/0185287 A1 | 7/2010 | Allard et al. |
| 2010/0185289 A1 | 7/2010 | Kirwan |
| 2010/0185292 A1 | 7/2010 | Hochschuler et al. |
| 2010/0204739 A1 | 8/2010 | Bae et al. |
| 2010/0217325 A1 | 8/2010 | Hochschuler et al. |
| 2010/0217393 A1 | 8/2010 | Theofilos |
| 2010/0249935 A1 | 9/2010 | Slivka |
| 2010/0249937 A1 | 9/2010 | Blain et al. |
| 2010/0268338 A1 | 10/2010 | Melkent et al. |
| 2010/0286777 A1 | 11/2010 | Errico |
| 2010/0286781 A1 | 11/2010 | Bullard |
| 2010/0286783 A1 | 11/2010 | Lechmann et al. |
| 2010/0292696 A1 | 11/2010 | Chantelot |
| 2010/0292737 A1 | 11/2010 | Suh |
| 2010/0305704 A1 | 12/2010 | Messerli |
| 2010/0312345 A1 | 12/2010 | Duffield |
| 2011/0009908 A1 | 1/2011 | Ferguson |
| 2011/0009966 A1 | 1/2011 | Michelson |
| 2011/0015675 A1 | 1/2011 | Howard |
| 2011/0015745 A1 | 1/2011 | Bucci |
| 2011/0082550 A1 | 4/2011 | Yeh |
| 2011/0082555 A1 | 4/2011 | Martz |
| 2011/0098747 A1 | 4/2011 | Donner et al. |
| 2011/0106159 A1 | 5/2011 | Nazeck |
| 2011/0144703 A1 | 6/2011 | Krause et al. |
| 2011/0166656 A1* | 7/2011 | Thalgott ............... A61F 2/4455 623/17.16 |
| 2011/0184415 A1 | 7/2011 | Anderson et al. |
| 2011/0190892 A1 | 8/2011 | Kirschman |
| 2011/0202136 A1 | 8/2011 | Brittan et al. |
| 2011/0208311 A1 | 8/2011 | Janowski |
| 2011/0213421 A1 | 9/2011 | Binder et al. |
| 2011/0230971 A1 | 9/2011 | Donner et al. |
| 2011/0251689 A1 | 10/2011 | Seifert et al. |
| 2011/0282453 A1 | 11/2011 | Greenhalgh |
| 2011/0295371 A1 | 12/2011 | Moskowitz et al. |
| 2011/0319896 A1 | 12/2011 | Papenfuss et al. |
| 2011/0319898 A1 | 12/2011 | O'Neil et al. |
| 2011/0319998 A1 | 12/2011 | O'Neil |
| 2012/0041559 A1 | 2/2012 | Melkent et al. |
| 2012/0078371 A1 | 3/2012 | Gamache |
| 2012/0078372 A1 | 3/2012 | Gamache |
| 2012/0078373 A1 | 3/2012 | Gamache |
| 2012/0083889 A1 | 4/2012 | Purcell et al. |
| 2012/0143336 A1 | 6/2012 | Aflatoon et al. |
| 2012/0150301 A1 | 6/2012 | Gamache |
| 2012/0150303 A1 | 6/2012 | Linares |
| 2012/0158143 A1 | 6/2012 | Shapiro |
| 2012/0191190 A1 | 7/2012 | Trieu |
| 2012/0197401 A1 | 8/2012 | Duncan |
| 2012/0203230 A1 | 8/2012 | Adams |
| 2012/0209331 A1 | 8/2012 | Michelson |
| 2012/0226319 A1 | 9/2012 | Armstrong et al. |
| 2012/0253406 A1 | 10/2012 | Bae |
| 2013/0041471 A1 | 2/2013 | Siegal et al. |
| 2013/0060337 A1 | 3/2013 | Petersheim et al. |
| 2013/0073044 A1 | 3/2013 | Gamache |
| 2013/0079883 A1 | 3/2013 | Butler et al. |
| 2013/0166027 A1 | 6/2013 | Bellas |
| 2013/0238095 A1 | 9/2013 | Pavento et al. |
| 2013/0268080 A1 | 10/2013 | Melkent et al. |
| 2013/0310939 A1 | 11/2013 | Fabian |
| 2013/0325071 A1 | 12/2013 | Niemiec et al. |
| 2013/0345813 A1 | 12/2013 | Frank et al. |

(56) References Cited

U.S. PATENT DOCUMENTS

| | | |
|---|---|---|
| 2014/0039623 A1 | 2/2014 | Iott et al. |
| 2014/0067069 A1 | 3/2014 | Lopez |
| 2014/0107786 A1 | 4/2014 | Geisler et al. |
| 2014/0114415 A1 | 4/2014 | Tyber |
| 2014/0135930 A1 | 5/2014 | Georges |
| 2014/0142705 A1 | 5/2014 | Duffield et al. |
| 2014/0156009 A1 | 6/2014 | Armstrong et al. |
| 2014/0172103 A1 | 6/2014 | O'Neil et al. |
| 2014/0364917 A1 | 12/2014 | Sandstrom |
| 2015/0313721 A1 | 11/2015 | Gamache et al. |
| 2015/0374511 A1 | 12/2015 | Pavento et al. |
| 2016/0045325 A1 | 2/2016 | Bellas et al. |
| 2016/0128846 A1 | 5/2016 | Voellmicke |
| 2016/0213487 A1 | 7/2016 | Wilson et al. |
| 2016/0317317 A1 | 11/2016 | Marchek et al. |
| 2017/0304068 A1 | 10/2017 | Bellas et al. |
| 2017/0312090 A1 | 11/2017 | Sharabani et al. |

FOREIGN PATENT DOCUMENTS

| | | |
|---|---|---|
| EP | 1609444 A1 | 12/2005 |
| EP | 1459711 B1 | 7/2007 |
| EP | 1683490 | 7/2008 |
| EP | 1506753 B1 | 9/2009 |
| EP | 1774926 | 6/2010 |
| EP | 1847240 | 11/2011 |
| FR | 2894130 A1 | 6/2007 |
| GB | 2220729 A | 1/1990 |
| GB | 457673 | 8/2009 |
| GB | 2457673 | 8/2009 |
| JP | 2006-524114 A | 10/2006 |
| JP | 2007-516808 | 6/2007 |
| JP | 2012-508044 | 4/2012 |
| WO | WO 1998/004217 | 2/1998 |
| WO | WO 1998/034568 A1 | 8/1998 |
| WO | WO 1999/052473 | 10/1999 |
| WO | WO 1999/038463 | 11/1999 |
| WO | WO 2001/008864 A1 | 2/2001 |
| WO | WO 2002/013732 | 5/2002 |
| WO | WO 2003/003951 A1 | 1/2003 |
| WO | WO 2003/005938 | 1/2003 |
| WO | WO 2003/005939 | 5/2003 |
| WO | WO 03/047473 | 6/2003 |
| WO | WO 2003/090650 | 11/2003 |
| WO | WO 2004/069106 | 8/2004 |
| WO | WO 2003/070128 | 10/2004 |
| WO | WO 2005/020861 | 3/2005 |
| WO | WO 2006/084057 | 8/2006 |
| WO | WO 2006/058281 A3 | 10/2006 |
| WO | WO 2007/003785 | 1/2007 |
| WO | WO 2007/118856 | 10/2007 |
| WO | WO 2007/098288 | 3/2008 |
| WO | WO 2009/025841 | 2/2009 |
| WO | WO 2008/149223 | 4/2009 |
| WO | WO 2009/064644 | 5/2009 |
| WO | WO 2009/091775 A2 | 7/2009 |
| WO | WO 2009/136009 | 11/2009 |
| WO | WO 2010/028045 | 3/2010 |
| WO | WO 2010/033786 | 3/2010 |
| WO | WO 2010/054208 | 5/2010 |
| WO | WO 2010/092893 | 8/2010 |
| WO | WO 2010/121028 A2 | 10/2010 |
| WO | WO 2010/099239 | 1/2011 |
| WO | WO 2011/008864 | 1/2011 |
| WO | WO 2011/035126 | 3/2011 |
| WO | WO 2011/080535 | 7/2011 |
| WO | WO 2012/056119 | 5/2012 |
| WO | WO 2013/018062 | 2/2013 |
| WO | WO 2013/096192 | 6/2013 |
| WO | WO 2013/191979 | 12/2013 |

OTHER PUBLICATIONS

Cain, "New Stand-Alone Anterior Lumbar Interbody Fusion Device" Biomechanical Comparison with Established Fixation Techniques, Spine, vol. 30, No. 23, p. 2631-2636, 2005, Lippincott Williams & Wilkins Inc.

Cohn et al., "Biodegradable PEO/PLA Block Copolymers", Journal of Biomaterials Research, 1998, vol. 22, pp. 993-1009.

Cohn, "Polymer Preprints", ACS Division of Polymer Chemistry, vol. 30(1), 1989, p. 498, (e.g. PEO/PLA).

Gercek, "Subsidence of Stand-Alone Cervical Cages in Anterior Interbody Fusion: Warning", Eur. Spine Journal, vol. 12, pp. 513-516, 2003, Springer-Verlag.

Heller, "Poly(Ortho Esters)", Handbook of Biodegradable Polymers, edited by Domb, et al, Hardwood Academic Press, pp. 99-118, 1997.

Humphries, "Anterior Fusion of the Lumbar Spine Using an Internal Fixative Device", Surgical Forum, vol. 1X, pp. 770-773, American College of Surgeons, 1959, Chicago, Illinois.

Kandziora, "Biomechanical Comparison of Cervical Spine Interbody Fusion Cages", Spine, vol. 26, No. 17, pp. 1850-1857, 2001, Lippincott Williams & Wilkins, Inc.

Kemnitzer et al., "Degradable Polymers Derived From the Amino Acid L-Tyrozine", The Handbook of Biodegradable Polymers, edited by Domb, et al., Hardwood Academic Press, 1997, pp. 251-272.

Oxland, "A Comparative Biomechanical Investigation of Anterior Lumbar Interbody Cages: Central and Bilateral Approaches", The Journal of Bone and Joint Surgery, pp. 383-393, vol. 82A, No., Mar. 2000.

Pavlov, "Good Outcome and Restoration of Lordosis After Anterior Lumbar Interbody Fusion With Additional Posterior Fixation", Spine, vol. 29, No. 17, pp. 1893-1900, 2004, Lippincott Williams & Watkins.

Pederson, "Thermal Assembly of a Biomimetic Mineral/Collagen Composite", Biomaterials, 2003, vol. 2, pp. 4881-3890, Elsevier.

Samandouras, "A New Anterior Cervical Instrumentation System Combining an Intradiscal Cage With an Integrated Plate", Spine, vol. 26, No. 10, pp. 1188-1192, 2001, Lippincott Williams and Watkins, Inc.

Vandorpe, "Biodegradable Polyphosphazenes for Biomedical Applications", The Handbook of Biodegradable Polymers, edited by Domb et al., Hardwood Academic Press, 1997, pp. 161-182.

International Search Report dated May 23, 2013 issued in PCT/US2013/029026.

International Preliminary Report on Patentability, International Application No. PCT/US2013/029026, dated Sep. 9, 2014, 10 pages.

International Search Report dated Nov. 15, 2013 issued in PCT/US2013/045360, 4 pgs.

International Preliminary Report on Patentability dated Dec. 23, 2014, issued in PCT/US2013/045360, 10 pgs.

International Search Report dated Apr. 11, 2013 issued in PCT/US2012/070082, 3 pgs.

International Preliminary Report on Patentability, dated Jun. 24, 2014 issued in PCT/US2012/070082, 7 pgs.

European Search Report dated Oct. 1, 2015 issued in European Application 13757720, 6pgs.

European Examination Report dated Mar. 19, 2014 for EP07855287.4.

Search Report dated Jan. 20, 2012 for EP07855287.

Schmiedberg, Isolation and characterization of metallic wear debris from a dynamic intervertebral disc prosthesis, J. Biomed. Mater. Res., vol. 28, Issue 11, 1277-1288, 1994.

* cited by examiner

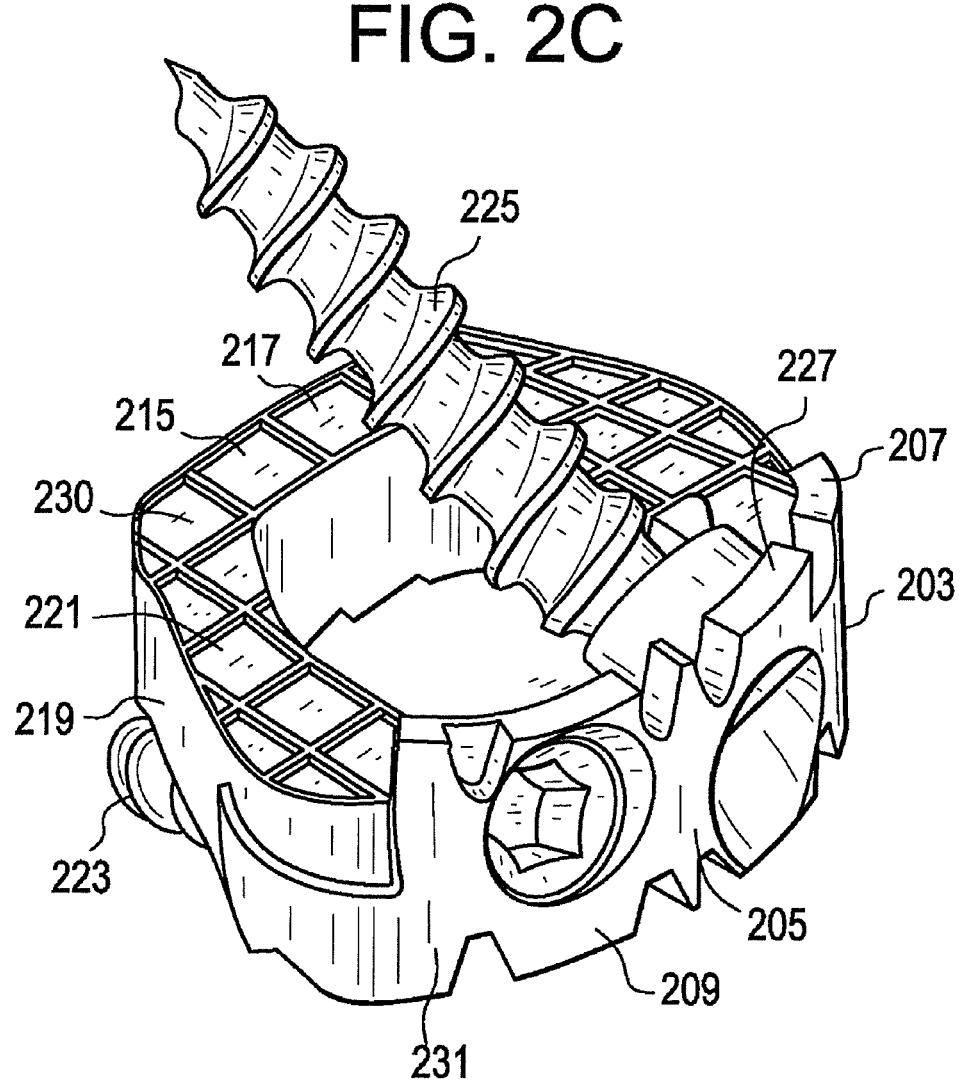

571

577 575
579

668

670

STAND ALONE INTERVERTEBRAL FUSION DEVICE

CONTINUING DATA

This is a divisional patent application of U.S. Ser. No. 13/237,233, filed Sep. 20, 2011, which claims priority from U.S. Ser. No. 61/385,959, filed Sep. 23, 2010, the specification of each of which is incorporated by reference in its entirety.

U.S. Ser. No. 13/237,233, filed Sep. 20, 2011, further claims priority from U.S. Ser. No. 61/466,309, filed Mar. 22, 2011, and entitled "Novel Implant Inserter Having a Laterally-Extending Dovetail Engagement Feature," the specification of which is incorporated by reference in its entirety. Ser. No. 13/237,233, filed Sep. 20, 2011, is related to U.S. Ser. No. 13/237,200 filed Sep. 20, 2011, entitled "Novel Implant Inserter Having a Laterally-Extending Dovetail Engagement Feature," the specification of which is incorporated by reference in its entirety.

U.S. Ser. No. 13/237,233, filed Sep. 20, 2011, further claims priority from U.S. Ser. No. 61/466,321, filed Mar. 22, 2011, and entitled "Fusion Cage with In-Line Single Piece Fixation," the specification of which is incorporated by reference in its entirety. U.S. Ser. No. 13/237,233, filed Sep. 20, 2011, is related to U.S. Ser. No. 13/237,174, filed Sep. 20, 2011, entitled "Fusion Cage with In-Line Single Piece Fixation," the specification of which is incorporated by reference in its entirety.

BACKGROUND OF THE INVENTION

During cervical spinal surgery for the fusion of an intervertebral disc, an anterior approach, discectomy and insertion of a spacer/cage are often performed. However, in these situations, the spine surgeon often prefers not to insert a plate on the anterior surface of the disc space with fixation through the anterior face of the cephalaud and caudal vertebral bodies. This reluctance stems from the observation that the anterior plate can be situated too proud and so its profile can sometimes cause patient discomfort and cause dysphasia and/or dysphonia.

In some fusion cases using a stand alone spacer, the surgeon must insert a fixation device (such as a screw) into the spacer at a sharp angle through sometimes challenging approaches. This can be especially difficult for the cervical spine, as the surgeon needs to either deliver the screw down into the inferior vertebral body but may be obstructed by the patient's chin, or deliver the screw up into the superior vertebral body but may be obstructed by the patient's sternum.

U.S. Pat. No. 7,135,043 (Nakahara) discloses an intervertebral cage comprising regulated insertion direction ridges. The cage may include a main body defined by an upper surface, a lower surface, and a pair of side surfaces. A withdrawal prevention portion is provided on the upper and/or the lower surfaces of the main body and asymmetrically with respect to the side surfaces in a top or bottom plan view. The withdrawal prevention portion regulates an insertion direction of the intervertebral cage. The portion of the Nakahara device that holds the screws does not possess teeth upon its upper and lower surfaces.

U.S. Patent Publication No. 2007-0250167 ("Bray") discloses a device for the fixation and support of bone bodies includes a base member for implantation into a patient at a location between two bone bodies. The base member of the device includes an enclosed chamber for receiving fusion material and apertures for receiving bone fasteners that can be embedded into the adjacent bone bodies. The device further includes protrusions extending from the base member, wherein the protrusions are configured for engagement with one or more bone bodies upon implantation and for progressive penetration into at least one bone body over a period of time subsequent to the implantation. However, the faceplate that holds the screws is not designed to be implanted in the disc space, but rather cloaks the anterior wall of the upper vertebral body.

The Globus Coalition Cage has protrusions that begin from the anterior face, and upon insertion, displace bone from the anterior face through the desired depth in a track formation rather than penetrating from within the space.

U.S. Pat. No. 7,232,464 (Mathieu) discloses an intervertebral implant in the form of a three-dimensional structure comprising (a) a top side and an underside that are designed to rest against the end plates of two adjacent vertebras, (b) a left side face and a right side face, (c) a front face and a rear face, (d) a horizontal center plane situated between the top side and the underside, (e) a vertical center plane situated between the left side face and the right side face and (f) a plurality of boreholes passing through the implant structure that are designed to receive longitudinal affixation elements, the axes of said elements intersecting the horizontal center plane. At least one of the boreholes is designed in a manner that the affixation element received in it can be rigidly connected to the intervertebral implant. The connection is implemented using a thread or by matching conical surfaces.

U.S. Patent Publication No. 2008-0306596 ("Jones") discloses a method and apparatus for use in spinal fusion procedures. An interbody fusion device has a first piece that is a load bearing device designed to bear the axial loading from the end plates of adjacent vertebrae. A second piece of the interbody fusion device is a retention device whose function is to prevent migration of the load bearing device. One or more fasteners secure the retention device to the vertebrae above and below the load bearing device. The fasteners cause the end plates of the vertebrae to compress the end plates to the load bearing device to facilitate proper fusion.

U.S. Patent Publication No. 2008-0249625 (Waugh) discloses a composite interbody spacer includes a first portion (such as a faceplate) formed of a first material and a second portion (such as a cage) formed of a second material.

U.S. Patent Publication No. 2008-0249575 ("Waugh") discloses a stand alone fusion cage in which the apertures that receive the bone anchors have an integral locking ring formed therein.

PCT Published Patent Application WO 02/13732 ("Bramlet") discloses an apparatus and method for fusing opposing spinal vertebrae. In an embodiment for a spinal implant of the present invention, the implant includes a body assembly and a retention member coupled to the body assembly. The retention member includes a tang where the tang is extendible from the body assembly. In a method of the present invention, the method includes the step of inserting an implant between adjacent vertebrae with a retention member of the implant in a first retracted configuration. The method also includes the step of configuring the retention member in a second extended configuration wherein the retention member is in its second extended configuration, a portion of a tang of the retention member extends from the implant and into one of the adjacent vertebrae.

U.S. Pat. No. 6,336,928 ("DePuy France") discloses a device for joining at least two vertebral bodies, which comprises at least one plate equipped at each end with anchoring parts which can be introduced substantially vertically into seats previously established in the vertebral bodies to be joined, and then, after introduction, can be folded back at an angle towards one another in order to exert a constant compression of the vertebral bodies and to ensure perfect anchoring, wherein each anchoring part is connected to the ends of the corresponding plate via a central connection zone delimiting two profiled notches in order to permit deformation of the zone, in such a way that each pair of anchoring parts permits a compression, both at the level of the plate and at the level of its ends, and in such a way that the anchoring parts at each end of the plate permit a clamping which prevents any extraction.

U.S. Pat. No. 6,773,437 ("Ogilvie") discloses a fusionless method of correcting spinal deformities in growing adolescents is disclosed utilizing a shape memory alloy staple. Various embodiments of the shape memory alloy staple include features such as barbs on the inner and outer surfaces of the prongs in the shape memory alloy staple as well as the use of notches on the crossbar or cross plate connecting the prongs to the shape memory alloy staple. In some embodiments, the shape memory alloy staple has an aperture defined through the cross plate for receiving a bone screw or other bone anchor which in turn allows the interconnection of a longitudinal member.

U.S. Pat. No. 7,594,931 ("LDR I") discloses an intervertebral arthrodesis for insertion in an intervertebral space separating opposite faces of two adjacent vertebrae has a ring shaped intervertebral cage having a bar that extends perpendicular to the axis of the spine. The bar has a height less than the rest of the cage. A surface of the cage contacting the vertebrae has an undulating shape for limiting sliding of the cage in a plane parallel to the vertebrae faces.

PCT Published Patent Application WO 2008/149223 ("LDR II") discloses an intersomatic cage, an intervertebral prosthesis, an anchoring device and an instrument for implantation of the cage or the prosthesis and the anchoring device, as well as a system and a method for implanting spinal implants and anchoring devices in vertebrae. An intersomatic cage or an intervertebral prosthesis fit closely to the anchoring device, which includes a body of elongated shape on a longitudinal axis, of curved shape describing, along the longitudinal axis, an arc whose dimensions and radius of curvature are designed in such a manner that the anchoring device may be implanted in the vertebral plate of a vertebra by presenting its longitudinal axis substantially along the plane of the intervertebral space, where the anchoring device is inserted, by means of the instrument, through a slot located in at least one peripheral wall of the cage or on at least one plate of the intervertebral disc prosthesis to penetrate into at least one vertebral plate PCT Published Patent Application WO-2010/028045 ("Lawton") discloses an intervertebral implant for insertion into an intervertebral disc space between adjacent vertebral bodies or between two bone portions. The implant includes a spacer portion, a plate portion operatively coupled to the spacer portion and one or more blades for securing the implant to the adjacent vertebral bodies. The blades preferably include superior and inferior cylindrical pins for engaging the adjacent vertebral bodies. The implant may be configured to be inserted via a direct lateral transposals approach. Alternatively, the implant may be configured for insertion via an anterior approach.

U.S. Published Patent Application 2005-0149192 ("Zucherman I") discloses an intervertebral implant has a fusion body with at least one keel that anchors the implant into cancellous bone of at least one vertebral body. A method for implantation includes lateral implantation of the implant.

U.S. Published Patent Application 2005-0149193 ("Zucherman II") discloses an intervertebral implant has a fusion body with at least one keel that anchors the implant into cancellous bone of at least one vertebral body. A method for implantation includes lateral implantation of the implant.

U.S. Published Patent Application 2004-0260286 ("Ferree") discloses an intradiscal components associated with Total Disc Replacements (TDRs), for example, are maintained in a disc space with keels having attributes that resist extrusion, pull-out, and/or backout. In the preferred embodiment, the keel is curved to resist extrusion, particularly anterior or posterior extrusion. The invention may include a TDR with a pair of endplates, each with a keel extending into a different vertebral body, and wherein the keels are angled or curved in different directions to resist extrusion. In alternative embodiments, the keel may include one or more members that extend outwardly to resist extrusion. Such members may be spring-biased, composed of a shape-memory material, or extend outwardly in response to an applied mechanical force, as might be applied by turning a screw. The keel may further include a bone-ingrowth plug or coating or 'teeth' to resist extrusion. Keels according to the invention may also be configured to resist extrusion through the addition of an elongate member that penetrates a vertebral body and the keel. Such a member may be a secondary keel or screw.

U.S. Published Patent Application 2008-0167666 ("Fiere") discloses equipment including at least one U-shaped clip whose lateral branches have sections and widths such that they may be inserted in the vertebral bodies of two vertebrae by impaction on the intermediate branch of the clip, so as to rest along the cortical bones of the vertebral bodies, and whose intermediate branch is deformable in such a way as to allow a reduction of the distance between the lateral branches; the intermediate branch, before implantation, has a length such that one of the lateral branches may be positioned slightly above the cortical bone forming the plate of the subjacent vertebra while the other lateral branch may be positioned slightly below the cortical bone forming the plate of the subjacent vertebra, and has, after deformation, a length such that the two lateral branches may be brought closer to each other.

U.S. Published Patent Application 2010-0004747 ("Lin") discloses a trans-vertebral and intra-vertebral plate and a rectangular cage with a slot for the plate of spinal fixation device are for neutralizing intervertebral movement for the spinal interbody fusion. The rectangular cage with a vertical or oblique slot is inserted into the intervertebral space from the lateral or anterior side of the spinal column and then the plate is inserted through the slot of the cage and hammered into and buried inside two adjacent vertebral bodies, to achieve three-dimensional intervertebral fixation.

The cited art does not disclose a fusion device that accommodates anti-migration fixation elements adjacent to the device, wherein the anti-migration fixation elements are then secured to the fusion device with another component.

The prior art does not disclose a zero-profile cage with anti migration elements secured into bone approximately adjacent to a surface of the cage within disc space, wherein the anti-migration fixation elements have the ability to provide compression onto the graft area upon addition of another component to the construct.

WO2009-064644 (Synthes) discloses a low profile intervertebral implant for implantation in an intervertebral disc space in-between adjacent vertebral bodies. The intervertebral implant includes a plate preferably coupled to a spacer. The plate is preferably formed from a first material and the spacer is preferably formed from a second material, the first material being different from the second material. The plate is preferably sized and configured so that the plate does not extend beyond the perimeter of the spacer. In this manner, the plate preferably does not increase the height profile of the spacer and the plate may be implanted within the intervertebral disc space in conjunction with the spacer.

SUMMARY OF THE INVENTION

In a first embodiment of the present invention, there is provided an angled fixation device, such as an angled screw. This angled fixation device may be used by the surgeon to secure a spacer to a spinal disc space. The proximal end portion of the angled fixation device is driven perpendicular to the anterior wall of the spacer, and so is parallel to the vertebral endplates and in-line with the inserter. The distal end portion of the angled fixation device is oriented at about a 45 degree angle (plus or minus 30 degrees) to the vertebral endplate it enters. In inserting the angled fixation device, the surgeon advances the drive mechanism perpendicular to the anterior wall of the spacer (and parallel to the endplates) to force the angled fixation device to take an angled trajectory into the adjacent vertebral body.

The in-line insertion of the angled fixation device allows for a smaller incision and access site for the spacer and angled fixation device, and also allows the surgeon to avoid having to insert the fixation device with the inserter disposed at a sharp angle. This essentially in-line approach can be especially advantageous for the cervical spine, as it allows the surgeon to avoid the patient's chin or sternum.

Therefore, in accordance with the present invention, there is provided intervertebral device comprising:
a) an intervertebral spacer having an anterior wall, a posterior wall, and first and second side walls connecting the anterior and posterior walls, the anterior wall having an anterior surface, an upper surface and a lower surface, a first throughhole extending upwards from the anterior surface and a second throughhole extending downwards from the anterior surface,
b) a first screw received in the first throughhole, the first screw having a distal tip, an intermediate shaft having a threadform thereon, and a proximal head, wherein the shaft of the first screw is angled.

Therefore, in accordance with the present invention, there is provided a medical implant comprising:
a) a wall having an upper surface and a lower surface, and a front surface, and a first hole extending into the wall from the front surface,
b) a first screw received in the first hole and having a distal tip, an intermediate shaft having a first thread, and a proximal head,
wherein a portion of the shaft is disposed at an angle to the first hole.

Therefore, in accordance with the present invention, there is provided an intervertebral device comprising:
a) an intervertebral spacer having an anterior wall, a posterior wall, and first and second side walls connecting the anterior and posterior walls, the anterior wall having an anterior surface, an upper surface and a lower surface, a first throughhole extending upwards from the anterior surface and a second throughhole extending downwards from the anterior surface,
b) a first nail received in the first throughhole, the first nail having a distal tip, an intermediate shaft having a plurality of barbs thereon, and a proximal head, wherein the shaft of the first nail is angled.

DESCRIPTION OF THE FIGURES

FIGS. 2B-3C disclose stand alone cage of the present invention with screws.

DETAILED DESCRIPTION OF THE INVENTION

For the purposes of the present invention, a "cage" is the spacer of the present invention without the anterior wall.

That is, the cage consists essentially of the posterior wall and the first and second side walls. The anterior wall may also be referred to as a "faceplate".

Figure 1A:
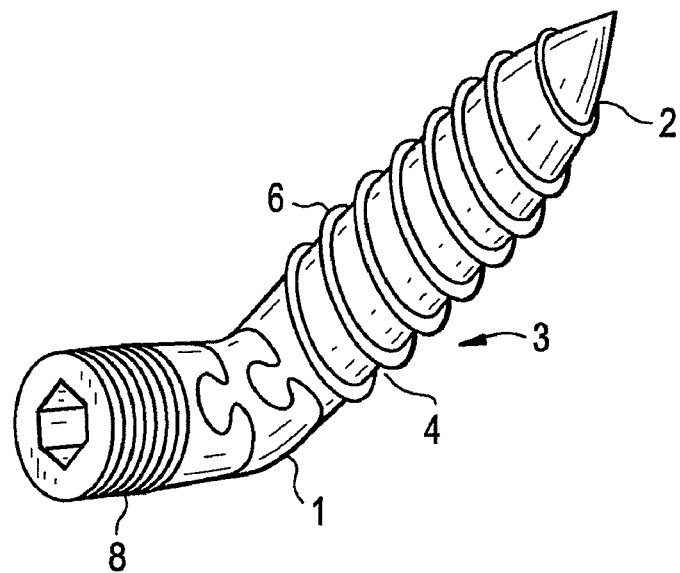
FIGS. 1A and 1B disclose jointed screws of the present invention.
Figure 1B:
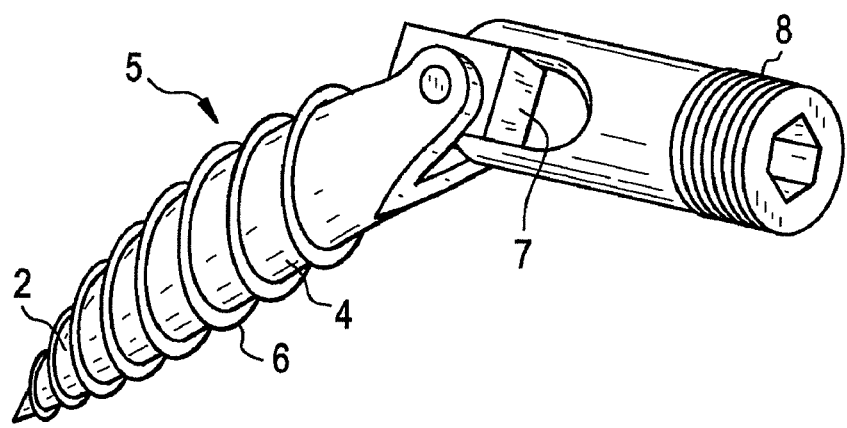
Figure 1C:
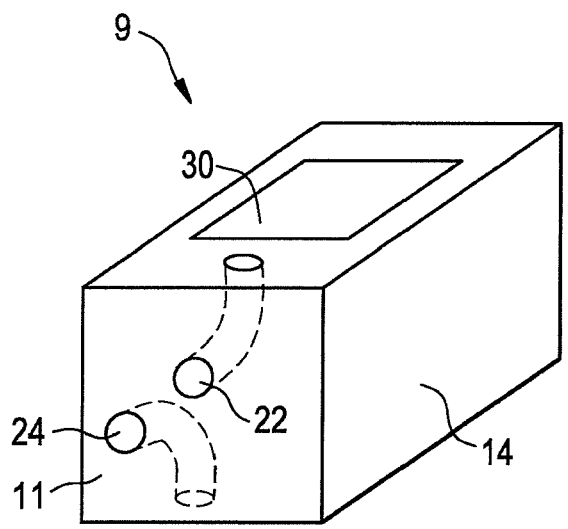
FIGS. 1C and 1D disclose cages for use with the jointed screw of the present invention.
Figure 1D:
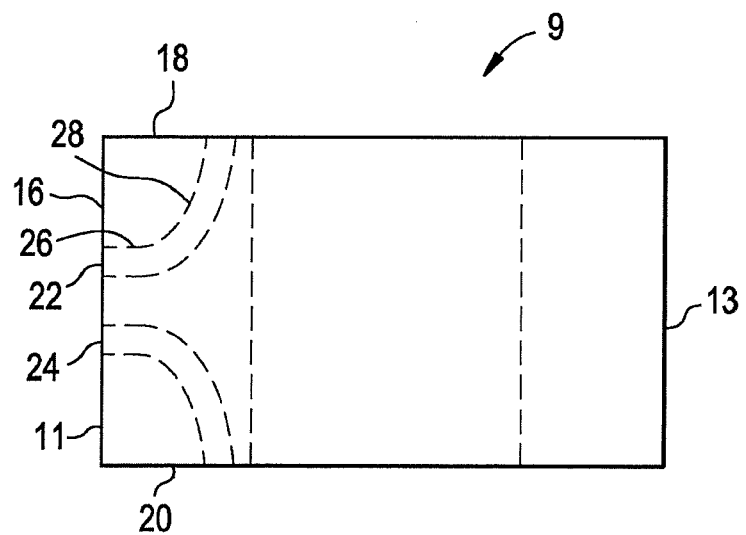

Now referring to FIG. 1A, in some embodiments, there is provided a first screw 3 having a distal tip 2 an intermediate shaft 4 having a threadform 6 thereon, and a proximal head 8. The angled shaft portion 1 of the first screw 3 is made of a flexible material. Now referring to FIG. 1B, in other embodiments, there is provided a second screw 5 having a distal tip 2 an intermediate shaft 4 having a threadform 6 thereon, and a proximal head 8. The angled shaft portion 7 includes a joint, such as a universal joint or a ball-and-socket joint.

Now referring to FIGS. 1A-1F, there is provided an intervertebral device comprising:
  a) an intervertebral spacer 9 having an anterior wall 11, a posterior wall 13, and first and second side walls 14 connecting the anterior and posterior walls, the anterior wall having an anterior surface 16, an upper surface 18 and a lower surface 20, a first throughhole 22 extending upwards from the anterior surface and a second throughhole 24 extending downwards from the anterior surface,
  b) a first bone fastener (such as screw 15) received in the first throughhole, the first screw having a distal tip 17, an intermediate shaft 19 having a threadform 21 thereon, and a proximal head 23,
  wherein the shaft of the first screw is angled.

In some embodiments, the angled shaft is made of a flexible structure, while in others, the angled shaft includes a joint, such as a universal joint or a ball-and-socket joint.

In some embodiments, the screw can be replaced by a nail having barbs.

In some embodiments, the spacer comprises a cage consisting essentially of the posterior wall and the first and second side walls, and the anterior wall is a separately manufactured faceplate that is mated to the cage.

In some embodiments, the first throughhole extends upwards through the upper surface of the anterior wall, and the second throughhole extends downwards through the lower surface of the anterior wall.

In some embodiments, the first throughhole 22 has an anterior portion 26 that extends substantially perpendicular to the anterior wall, and a posterior portion 28 that extends to the upper surface 18 of the anterior wall. In addition, posterior portion 28 can extend partially or fully into the graft window (not just the upper surface).

In some embodiments, wherein the anterior wall comprises a posterior surface 30, and the first throughhole extends upwards through the posterior surface of the anterior wall, and the second throughhole extends downwards through the posterior surface of the anterior wall.

In some embodiments, there is provided a second screw received in the second throughhole, the second screw having a distal tip, an intermediate shaft having a threadform thereon, and a proximal head, wherein the shaft of the second screw is angled.

Thus, the device of the present invention can generally be considered to be a medical implant comprising:
  a) a wall having an upper surface and a lower surface, and a front surface, and a first hole extending into the wall from the front surface,
  b) a first screw received in the first hole and having a distal tip, an intermediate shaft having a first thread, and a proximal head,
wherein a portion of the shaft is disposed at an angle to the first hole.

In this general embodiment, the first hole preferably extends into the wall at an angle that is not perpendicular to the front surface, and the shaft of the first screw is angled. Preferably, the shaft of the first screw is flexible.

Thus, the present invention can also generally be considered to be a method of fixing a medical implant having a wall having a front surface and a first hole extending into the wall from the front surface, the method comprising the steps of:
  a) implanting the implant in a patient, and
  b) inserting a first screw having a shaft into the first hole, wherein a portion of the shaft is disposed at an angle to the first hole during insertion.

For the purposes of the present invention, the flexible structure comprising the angled shaft can be either made of an intrinsically flexible material or an intrinsically stiff material having a geometry that enables flexing or bending.

Figure 1E:
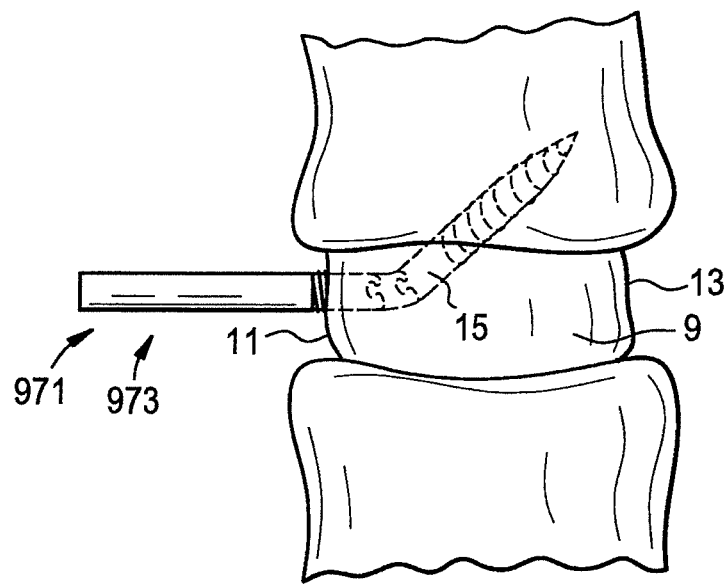
FIGS. 1E and 1F disclose the jointed screw and cage implanted in a disc.
Figure 1F:
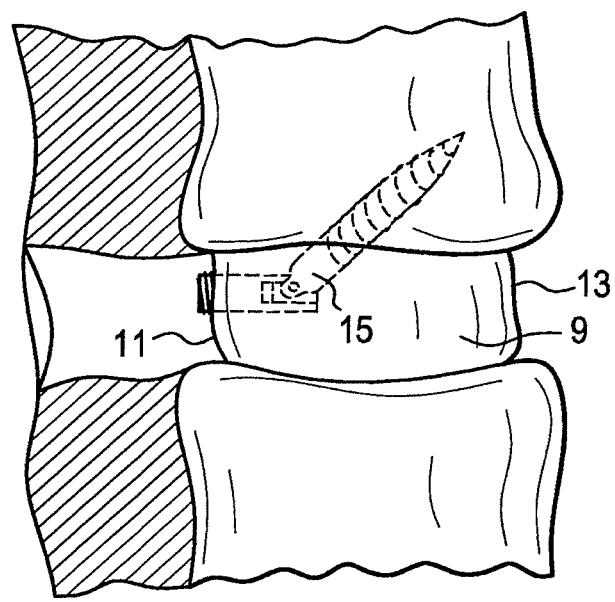

In inserting the angled fixation device, and now referring to FIG. 1E, the surgeon advances the drive mechanism 973 of the inserter 371 perpendicular to the anterior wall of the spacer (and parallel to the endplates) to force the angled fixation device to take an angled trajectory into the adjacent vertebral body.

Second Aspect of the Invention

In accordance with the present invention, there is provided a zero-profile or low-profile implant that can be used in a fusion procedure and sit completely inside the disc space. The implant includes features incorporated into one or more surfaces of the implant that control the amount of endplate subsidence into the implant. These features can be positioned around the periphery of the implant to capture targeted bone.

In general, a "controlled subsidence feature" on an implant provides increasing resistance against endplate subsidence as the subsidence progresses into the implant. The increase in resistance is generally accomplished by increasing the contact area between the implant and the endplates, thereby lowering the maximum stress experienced by the endplates. Typically, any surface having an acutely angled projection will function so as to control subsidence. Such a projection will have greater and greater contact with the endplate as the endplate subsides into the implant. Typically, controlled subsidence features include pyramids, cones and wedges. In some embodiments, the controlled subsidence feature is a pointed projection extending outward from an upper or lower surface of the implant. Such a feature will also help prevent cage migration as well as increase the implant's rotational stability.

In some embodiments, the implant comprises two separate components: a three-walled cage plus an anterior faceplate having a desirable mechanical rigidity that can house a cam, bushing, and/or a thread form to allow anchors to pass therethrough, if desired.

Also disclosed is a method of securing the cage of the present invention to one or more levels of the spine with optional fixation devices, such as bone anchors such as screws. The optional fixation device preferably passes through at least a portion of the anterior wall of the cage. In these embodiments, the fixation devices enter the superior and inferior vertebral bodies somewhere in and along the anterior wall from within or partially within the disc space. The hybrid plate/cage assembly of the present invention having optional fixation essentially creates a near zero-profile assembly.

In some embodiments, the anterior wall is a separately-manufactured faceplate having anti-migration features. This faceplate can attach to a separate cage component made from such diverse materials as ceramics, hydroxyapatite, tricalcium phosphate, allograft, CFRP, PEEK and Endolign. These components can couple to each other from numerous planes (i.e., from the front-to-back, from the top-to-bottom, and from the side-to-side) so as to form a desirable net shape assembly that conforms to the patient anatomy based on the chosen surgical approach.

In some embodiments, there is provided a multi-piece intervertebral fusion device assembly having anti-migration/anti-expulsion features on both cage and faceplate components.

In some embodiments, there is provided an implant having a thin anterior wall containing features designed to control subsidence into bone. Preferably, these features are present on both the upper and lower faces of the anterior wall and are distributed evenly across the anterior wall. More preferably they are symmetrically distributed.

In some embodiments, the anti-migration features of the faceplate are in the form of a pyramid, tooth, spike, diamond, keel or ridge. They are distributed anatomically across the front face to assist in load sharing with the graft spacer and to aid in ensuring final placement prior to fusion.

Figure 2A:
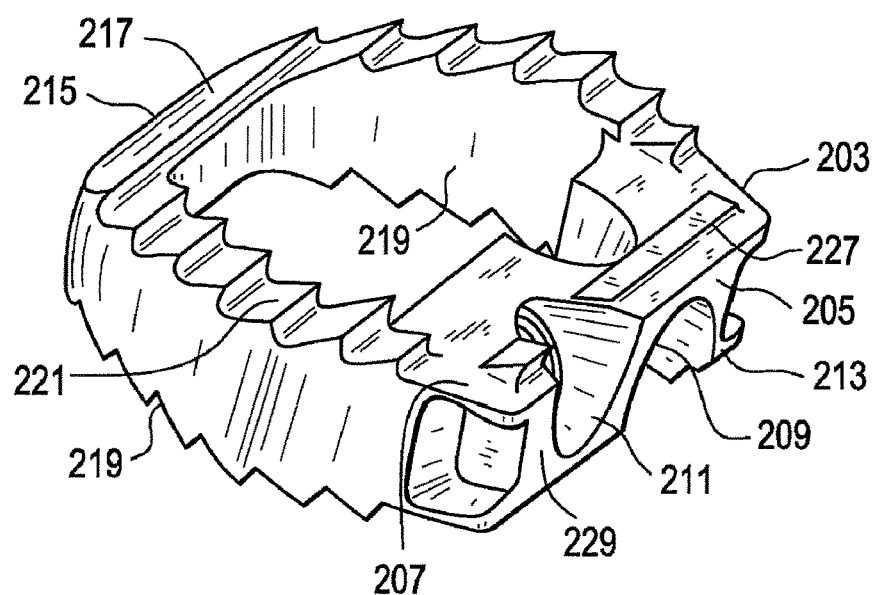
FIG. 2A discloses one embodiment of a stand alone cage of the present invention.
Figure 2B:
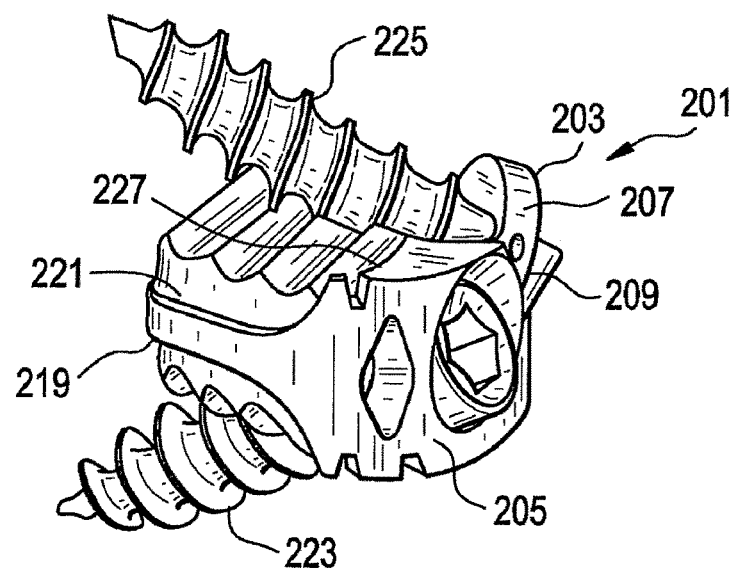

Now referring to FIGS. 2A-2C, there is provided an intervertebral device 201 for insertion into a disc space defined by opposing vertebral endplates, comprising
i) an intervertebral spacer 203 comprising:
 a) an anterior wall 205 having an upper surface 207 and a lower surface, an anterior surface 209, and a first throughhole 211 extending upwards from the anterior surface and a second throughhole 213 extending downwards from the anterior surface,
 b) a posterior wall 215 having an upper surface 217 and a lower surface, and
 c) first and second side walls 219 connecting the anterior and posterior walls, each side wall having an upper surface 221 and a lower surface,
ii) a first bone anchor 223 received in the first through hole,
iii) a second bone anchor 225 received in the second through hole,
wherein the upper and lower surfaces of the anterior wall contact the opposing vertebral endplates,
wherein at least one of the upper and lower surfaces of the anterior wall comprises a controlled subsidence feature 227,
wherein the anterior wall is characterized by a material having an intrinsic strength, the remainder of the spacer is characterized by a material having an intrinsic strength, and the intrinsic strength of the material of the anterior wall is greater than the intrinsic strength of the material of the remainder of the spacer.

In some embodiments, each of the upper or lower surfaces of the anterior wall comprises a controlled subsidence feature.

In some embodiments, the controlled subsidence feature acts to increase contact area between the spacer and the endplates as subsidence increases.

In some embodiments, the controlled subsidence feature comprises an acutely angled projection 229 extending outwards from the upper or lower surface of the anterior wall.

In some embodiments, the controlled subsidence feature is selected from the group consisting of a pyramid, a cone and a wedge.

In some embodiments, the anterior wall comprises attachment features for attaching to the side walls.

In some embodiments, at least one side wall comprises a controlled subsidence feature.

Now referring to FIG. 2C, there is provided an intervertebral device for insertion into a disc space defined by opposing vertebral endplates, the device having an anterior-most surface and comprising
i) an intervertebral cage 230 comprising:
 a) a posterior wall having an upper surface and a lower surface, and
 b) first and second side walls connecting the anterior and posterior walls, each side wall having an upper surface and a lower surface,
ii) a faceplate 231 attaching to each of the side walls and forming the anterior-most surface of the device, the faceplate having an upper surface and a lower surface, and an anterior surface,
iii) a first bone anchor extending upwards and posteriorly from the cage and
iv) a second bone anchor extending downwards and posteriorly from the cage,
wherein the upper and lower surfaces of the faceplate contact the opposing vertebral endplates,
wherein at least one of the upper and lower surfaces of the faceplate comprises a controlled subsidence feature.

In some embodiments, there is provided an intervertebral device for insertion into a disc space defined by opposing vertebral endplates, comprising
i) an intervertebral spacer comprising:
 a) an anterior wall having an upper surface and a lower surface, an anterior surface, and a first throughhole extending upwards from the anterior surface and a second throughhole extending downwards from the anterior surface,
 b) a posterior wall having an upper surface and a lower surface, and
 c) first and second side walls connecting the anterior and posterior walls, each side wall having an upper surface and a lower surface,
ii) a first bone anchor received in the first through hole,
iii) a second bone anchor received in the second through hole,
wherein the upper and lower surfaces of the anterior wall contact the opposing vertebral endplates,
wherein the upper and lower surfaces of the anterior wall define an anterior wall height, and
wherein the upper and lower surfaces of the posterior wall define a posterior wall height, and
wherein the anterior wall height is greater than the posterior wall height.

Preferably, at least one of the upper and lower surfaces of the faceplate comprises a controlled subsidence feature.

Also in accordance with the present invention, there is provided a method of inserting an intervertebral device into a disc space, wherein the device comprises,
i) an intervertebral spacer comprising:
 a) an anterior wall having an upper surface and a lower surface, an anterior surface, and a first throughhole extending upwards from the anterior surface and a second throughhole extending downwards from the anterior surface,
 b) a posterior wall having an upper surface and a lower surface, and
 c) first and second side walls connecting the anterior and posterior walls, each side wall having an upper surface and a lower surface,
ii) a first bone anchor received in the first through hole,
iii) a second bone anchor received in the second through hole, wherein at least one of the upper and lower surfaces of the anterior wall comprises a controlled subsidence feature, wherein the anterior wall is manufactured as a separate component from a remainder of the spacer,
the method comprising the steps of:
  a) creating the disc space between opposing vertebral endplates, and
  b) inserting the device into the disc space so that the upper and lower surfaces of the anterior wall contact the opposing vertebral endplates.

Preferably, the anterior wall is characterized by a material having an intrinsic strength, the remainder of the spacer is characterized by a material having an intrinsic strength, and the intrinsic strength of the material of the anterior wall is greater than the intrinsic strength of the material of the remainder of the spacer.

Third Aspect of the Invention

In some embodiments, the screw associated with the stand alone intervertebral fusion devices of the present invention has an enhanced fixation feature. For the purposes of the present invention, a screw having an enhanced fixation feature is selected from the group consisting of:
  a) a screw coated with bone ingrowth substance such as hydroxyapatite or titanium calcium phosphate. Such a screw would be desirable for use in an aged patient whose osteogenic profile may not be able to provide appropriate bone in-growth;
  b) a fenestrated screw for use with either cement or biologic injections or bone ingrowth material. Such a screw may be useful in improving the pull-out strength of the screw in osteoporotic bone;
  c) an expanding screw, which may be useful in preventing device migration;
  d) a cannulated screw, which may be useful in percutaneous or other minimally invasive procedures using a guidewire;
  e) a resorbable screw that could be gradually eliminated from the patient as fusion occurred. Such a screw could be made from a resorbable material such as PLA, PGA, PLGA, HA-filedd polymer, TCP-filled polymer, or BIOCRYL RAPIDE™.
  f) a screw coated with an anti-bacterial agent, which could be particularly useful in treating trauma cases that pose infection risks; and
  g) a nail having fins extending therefrom (such as a shoulder anchor such as the MITEK™ shoulder anchor.

Figure 3A:
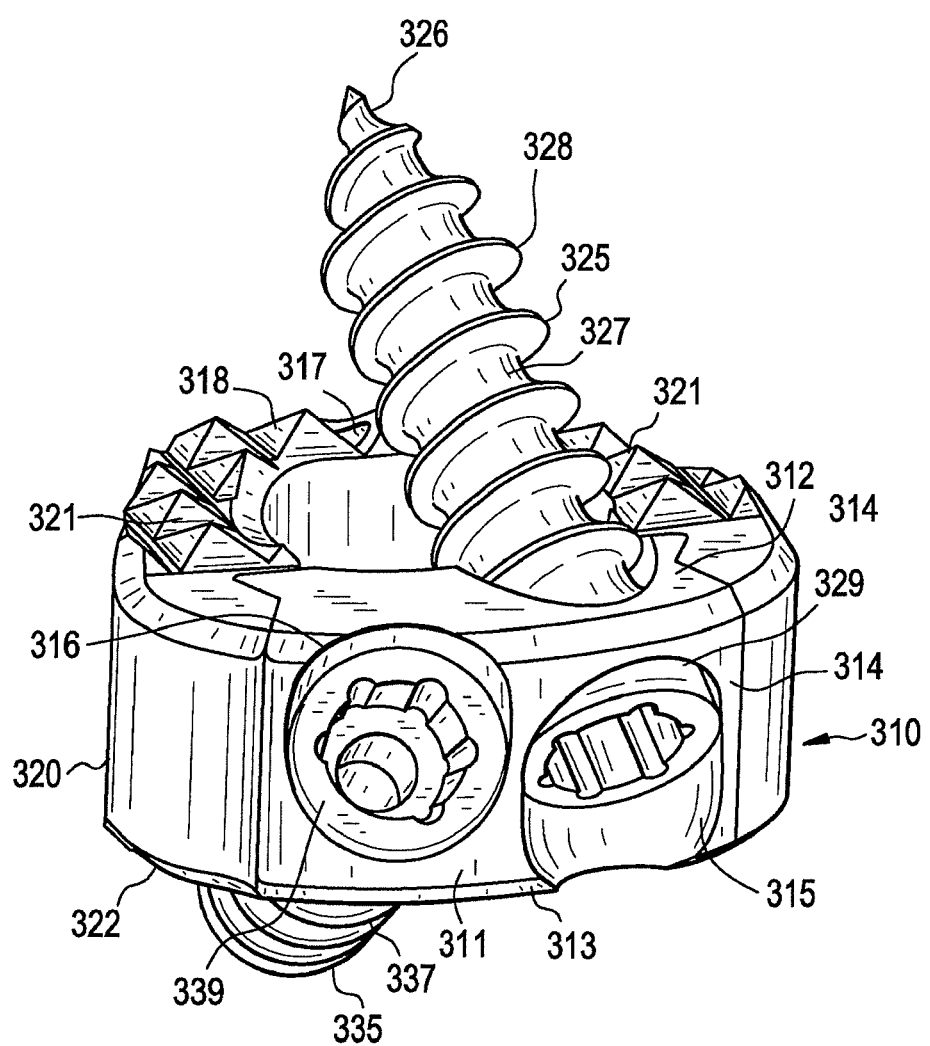
Figure 3B:
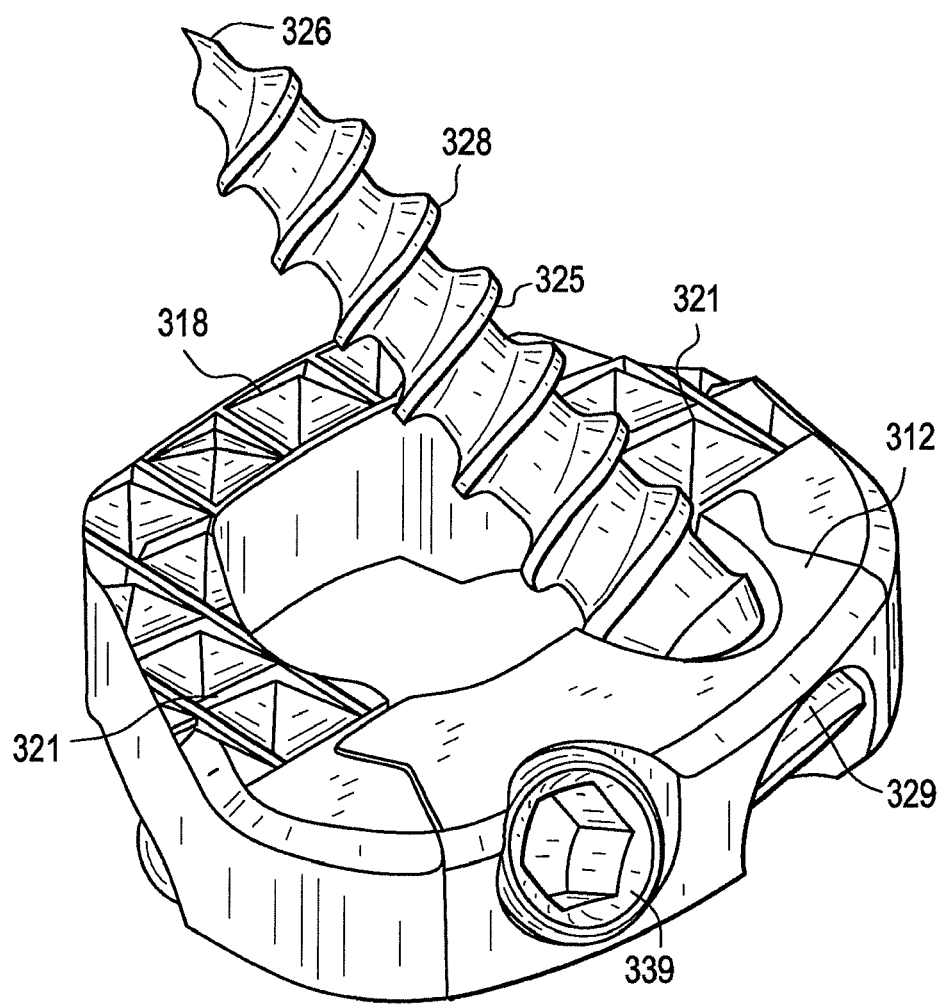
Figure 3C:
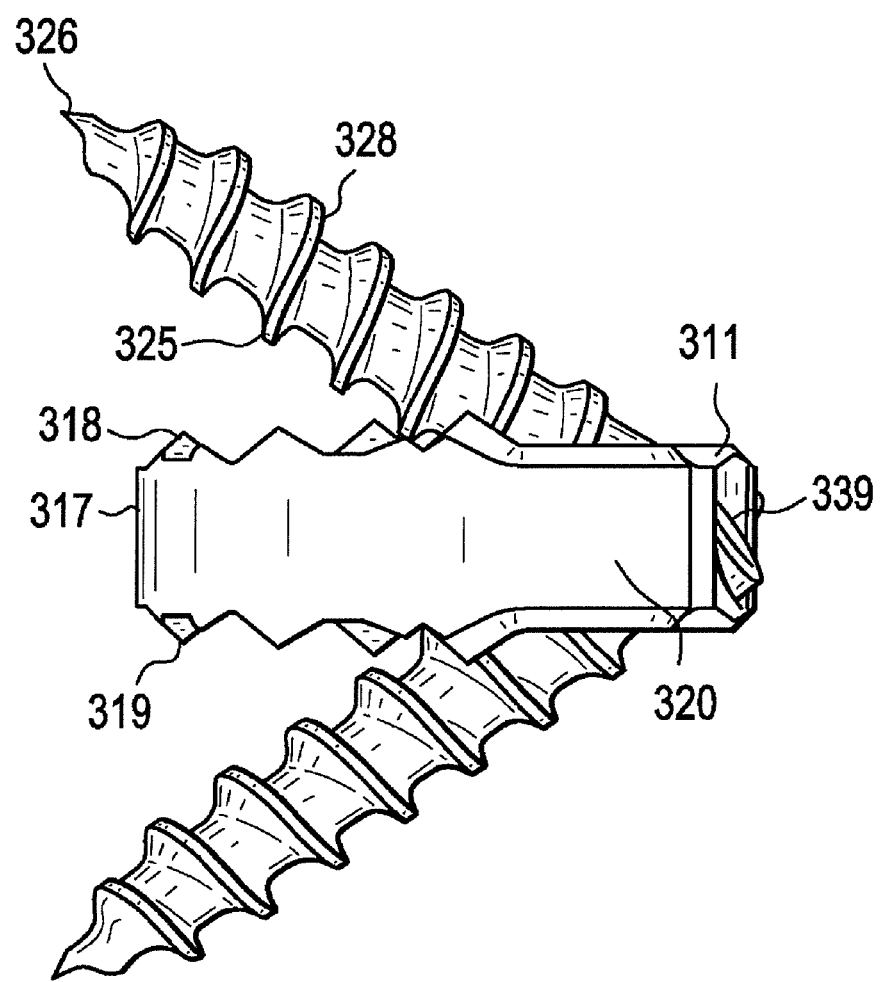

Now generally referring to FIGS. 3a-3c, there is provided an intervertebral device for insertion into a disc space defined by opposing vertebral endplates, comprising
i) an intervertebral spacer 310 comprising:
  a) having an anterior wall 311 having an upper surface 312 and a lower surface 313, an anterior surface 314, and a first hole 315 extending from the anterior surface to the upper surface and a second hole 316 extending from the anterior surface to the lower surface,
  b) a posterior wall 317 having an upper surface 318 and a lower surface 319, and
  c) first and second side walls 320 connecting the anterior and posterior walls, each side wall having an upper surface 321 and a lower surface 322,
ii) a first screw 325 received in the first hole and having a distal tip 326, an intermediate shaft 327 having a first thread 328, and a proximal head 329, and
iii) a second screw 335 received in the first hole and having a distal tip, an intermediate shaft 337 having a first thread, and a proximal head 339.

Fourth Aspect of the Invention

In accordance with the present invention, there is provided an intervertebral implant comprising a spacer made of two or more components made of dissimilar materials coupled together to take advantage of the material properties of each selected material. These components can be coupled via various disclosed geometries.

Figure 4A:
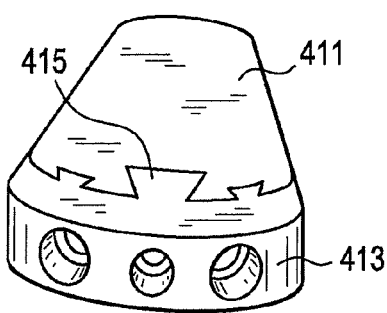
FIGS. 4A-4U disclose various embodiments of stand alone cages comprising dissimilar materials.

Now referring to FIG. 4A, there is provided, in one embodiment, a device comprising a) a cage 411 comprising bone (preferably at least 50 v/o bone) and b) a faceplate 413 comprising a metallic or polymeric material, wherein the faceplate attaches to the bone. In one such embodiment, there is provided an anterior wall consisting essentially of a metallic material, with the remainder of the spacer consisting essentially of bone. One advantage of this design is that it provides more graft-endplate contact than conventional designs that deliver graft. This contact advantage is particularly clear when the device of the present invention is compared to a conventional synthetic spacer having a graft chamber. Because of the enhanced strength of the anterior wall of this design, it may be possible to pass bone anchors through an aperture in the metallic anterior wall portion of the device.

Therefore, in accordance with the present invention, there is provided an intervertebral device for insertion into a disc space defined by opposing vertebral endplates, comprising
i) an intervertebral spacer comprising:
  a) having an anterior wall having an upper surface and a lower surface, an anterior surface, and a first hole extending from the anterior surface to the upper surface and a second hole extending from the anterior surface to the lower surface,
  b) a posterior wall having an upper surface and a lower surface, and
  c) first and second side walls connecting the anterior and posterior walls, each side wall having an upper surface and a lower surface,
ii) a first bone anchor received in the first hole, the first bone anchor having a distal tip, an intermediate shaft, and a proximal head,
iii) a second bone anchor received in the second hole, the second bone anchor having a distal tip, an intermediate shaft, and a proximal head,
wherein the anterior wall is made of a first material and a remainder of the spacer is made of a second material, and
wherein the anterior wall is fixed into the remainder of the spacer so that it does not float.

In some embodiments, the bone cage and metallic faceplate possess matching engagement features, such as dovetail features 415.

Figure 4B:
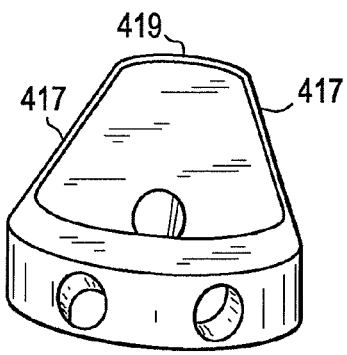
FIG. 4V discloses a plate of a stand alone cage.

In some embodiments, and now referring to FIG. 4B, the metal faceplate has arms 417 that wrap around the bone cage and meet to form a posterior wall 419.

Figure 4C:
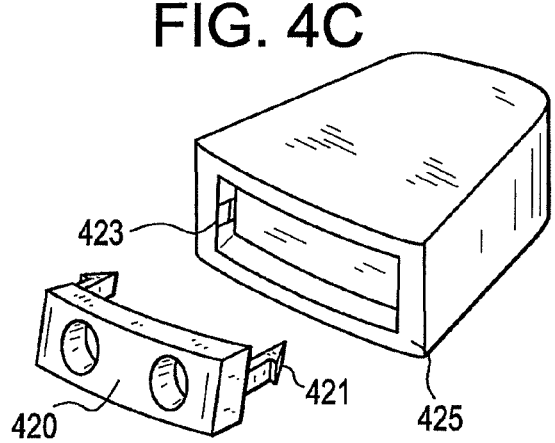

In some embodiments, and now referring to FIG. 4C, the metal faceplate 420 has lateral prongs 421 fit into mating recesses 423 machined into the anterior face 425 of the bone cage.

In alternative embodiments, the material of the anterior wall is less stiff than the material of the remainder of the spacer (i.e., the cage). This condition allows more load to be taken by bone graft contained within a hollow of the cage.

This design could also provide a predetermined amount of micromotion and/or springback, which may be desirable.

Therefore, in accordance with the present invention, there is provided an intervertebral device for insertion into a disc space defined by opposing vertebral endplates, comprising
i) an intervertebral spacer comprising:
   a) an anterior wall having an upper surface and a lower surface, an anterior surface, and a first through hole extending upwards from the anterior surface and a second through hole extending downwards from the anterior surface,
   b) a posterior wall having an upper surface and a lower surface, and
   c) first and second side walls connecting the anterior and posterior walls, each side wall having an upper surface and a lower surface,
ii) a first bone anchor received in the first through hole,
iii) a second bone anchor received in the second though hole,
wherein the anterior wall is made of a first material and a remainder of the spacer is made of a second material,
wherein the material of the anterior wall has a stiffness, the material of the remainder of the spacer has a stiffness, and the stiffness of the anterior wall material is less than the stiffness of the material of the remainder of the spacer.

In general, the dissimilar nature of the materials could cause undesirable micromotion if they were placed next to each other in a floating arrangement. Therefore, it is desirable to fix the two components together to form a non-displaceable, non-floating connection.

In some embodiments, the faceplate is front loaded onto the cage.

Figure 4D:
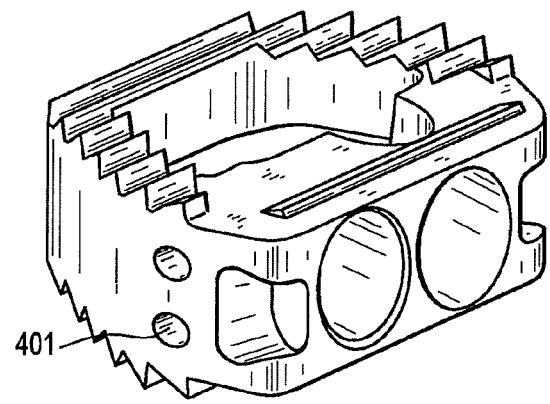

Now referring to FIG. 4D, in some embodiments, the fixed connection of the present invention is accomplished by providing aligned holes in the cage and faceplate and inserting at least one cross pin 401 therethrough.

Figure 4E:
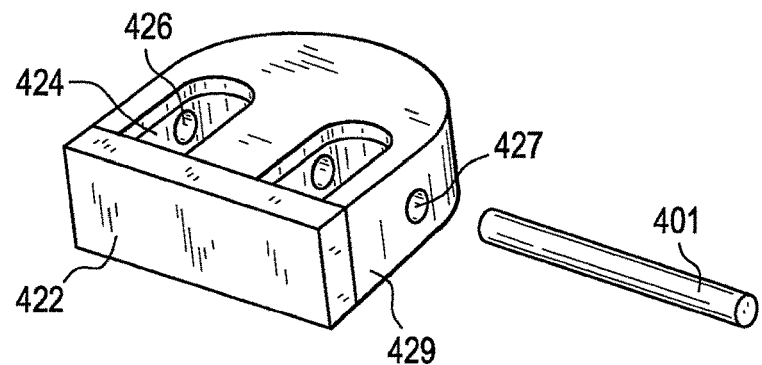

In one embodiment thereof, and now referring to FIG. 4E, the faceplate 422 has wings 424 extending posterior, and the wings have holes 425. When this faceplate is attached to the front of the cage, the holes of the faceplate aligned with holes 427 provided on the sidewalls 429 of the cage.

Figure 4F:
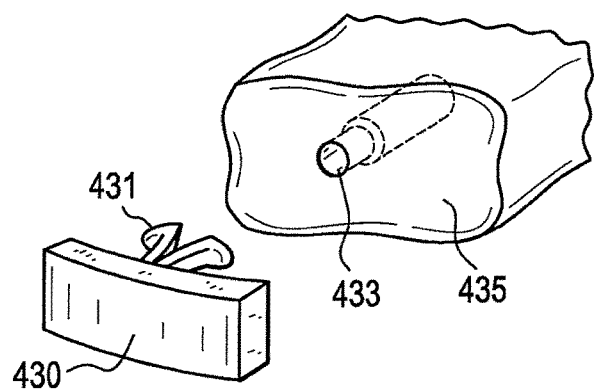

In one embodiment, and now referring to FIG. 4F, the faceplate 430 has a pair of prongs 431 fitting into a central recess 433 machined into the anterior face 435 of the cage.

Figure 4G:
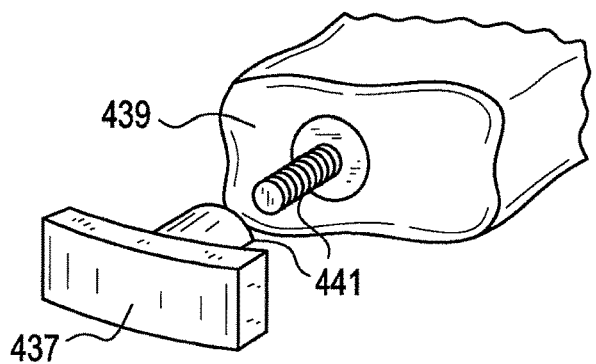

In one embodiment, and now referring to FIG. 4G, the faceplate 437 and the anterior face 439 of the cage are mated through threaded features 441.

Figure 4H:
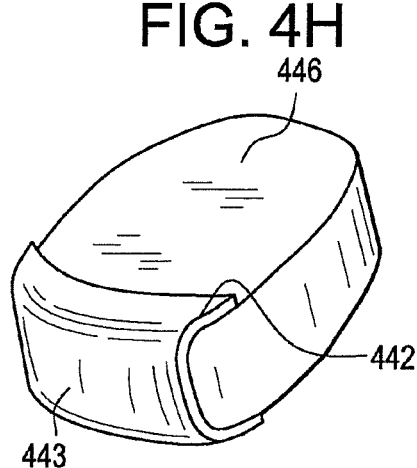

In one embodiments, and now referring to FIG. 4H, the faceplate 443 has a U-shape and is wraps around the anterior wall 445 of the cage. This faceplate is preferably press fit onto the anterior wall of the cage. The arms 442 of the faceplate contact the inferior 444 and superior 446 faces of the cage.

Figure 4I:
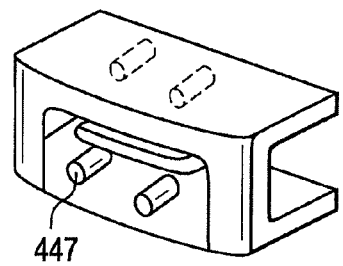

In preferred embodiments thereof, and now referring to FIG. 4I, the U-shaped faceplate has prongs 447 thereon that provide additional securement to the bone cage.

Figure 4J:
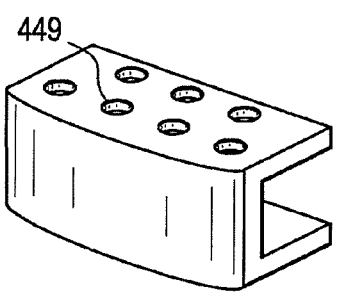

In preferred embodiments thereof, and now referring to FIG. 4J, the U-shaped faceplate has disperse lances 449 therein that provide additional securement to the bone cage.

Figure 4K:
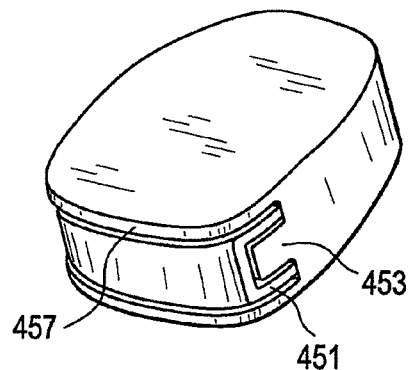

In some preferred embodiments thereof, and now referring to FIG. 4K, the U-shaped faceplate 451 is received into a recess in the anterior wall 453 of the cage so that the posterior face 455 of the faceplate is flush with the anterior surface 457 of the cage.

Figure 4L:
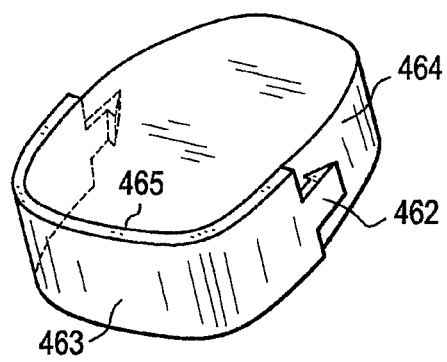

In one embodiments, and now referring to FIG. 4L, the faceplate 463 has a U-shape and is wraps around the anterior wall 465 of the cage. This faceplate is preferably press fit onto the anterior wall of the cage. The arms 462 of the faceplate contact the side walls 464 of the cage.

Figure 4M:
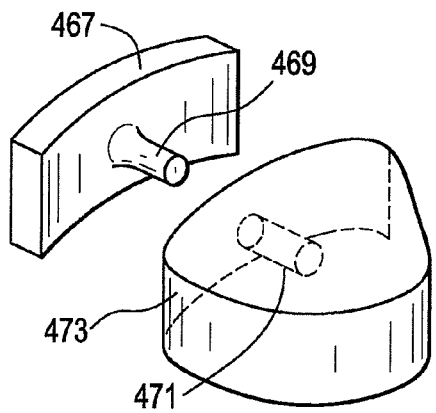

In one embodiments, and now referring to FIG. 4M, the faceplate 467 has a pin 469 extending posteriorly therefrom, and this pin extending into a mating recess 471 provided on the anterior face 473 of the cage.

In some embodiments, the faceplate is side loaded onto the cage.

Figure 4N:
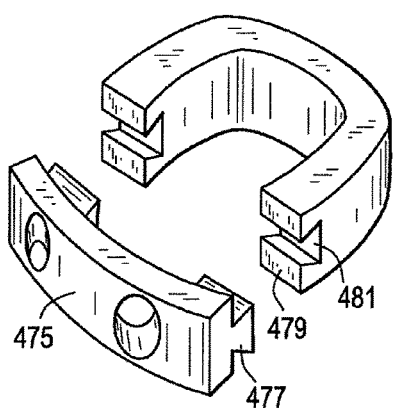

In some embodiments thereof, and now referring to FIG. 4N, the faceplate 475 has dovetails 477 extending posteriorly therefrom, while the anterior face 479 of the bone cage 481 has dovetail recesses 483 formed therein. The dovetails of the faceplate are sideloaded into the dovetail recesses.

Figure 4O:
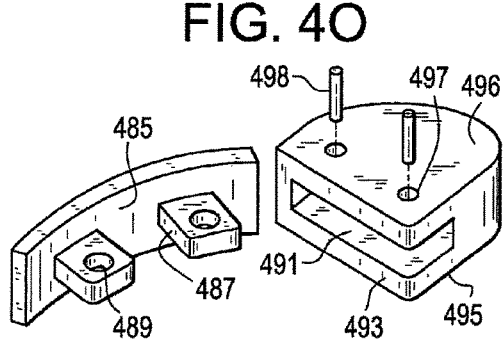

In some embodiments thereof, and now referring to FIG. 4O, the faceplate 485 has tabs 487 extending posteriorly therefrom, within holes 489 extending tabs. This faceplate is sideloaded into a cage having a recess 491 that extends substantially laterally across the anterior face 493 of the cage and partially down a sidewall 495 as well. The upper surface 496 of the cage has a pair of holes 497 bored therein so that the holes of the cage align with the holes of the faceplate. Into these aligned holes is inserted an insertion pin 498.

In some embodiments, the faceplate is top loaded onto the cage.

Figure 4P:
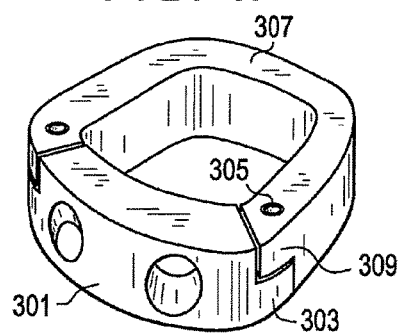

In some embodiments thereof, and now referring to FIG. 4P, the faceplate 301 has tabs 303 extending laterally therefrom, and insertion pins 305 extending from the tabs in the superior direction. Similarly, the cage 307 has tabs 309 extending laterally therefrom, and insertion holes extending through the tabs in the superior direction. The cage and faceplate are mated in a press fit fashion so that the insertion pin of the faceplate extends through the insertion hole of the cage.

Figure 4Q:
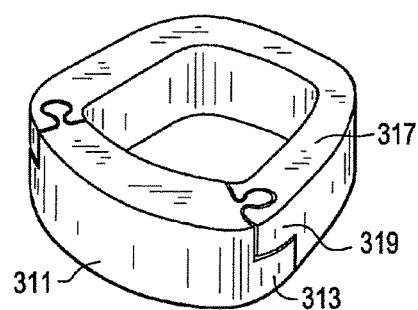

In some embodiments thereof, and now referring to FIG. 4Q, the faceplate 311 has tabs 313 extending laterally therefrom. Similarly, the cage 317 has tabs 319 extending laterally therefrom. These tabs are formed in a jigsaw puzzle manner so that the cage and faceplate can be mated in a press fit fashion so that the tab of the faceplate mates with the tab of the cage.

Figure 4R:
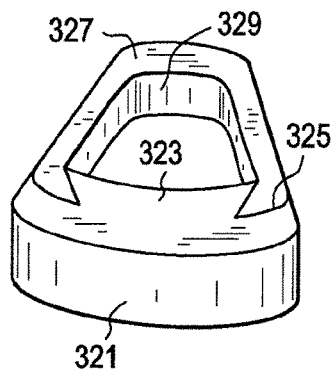

In some embodiments thereof, and now referring to FIG. 4R, the faceplate 321 has a dovetail 323 extending posteriorly therefrom. Similarly, the anterior wall 325 of the cage 327 has a dovetail recess therein extending from the upper surface 329 to the lower surface of the cage. The faceplate is top or bottom loaded into the cage so that the dovetail and corresponding recess mate.

Figure 4S:
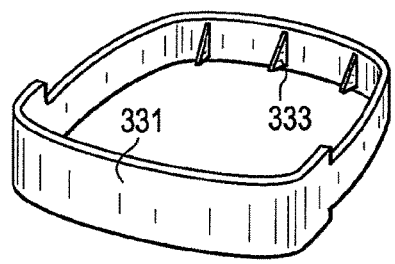

In some embodiments thereof, and now referring to FIG. 4S, the faceplate 331 is essentially a band that wraps around the cage. Provided on the posterior portion of the faceplate is a plurality of crush ribs 333 that enhance the friction fit with the cage (not shown).

Figure 4T:
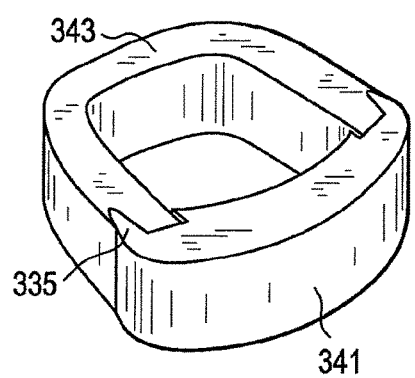

In some embodiments thereof, and now referring to FIG. 4T, the faceplate 341 has outer arms 335 that form an outside dovetail with the cage 343.

Figure 4U:
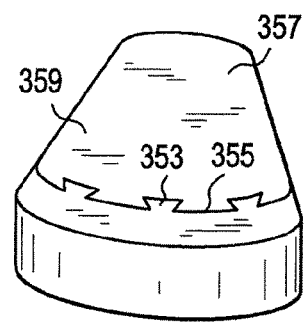

In some embodiments thereof, and now referring to FIG. 4U, the faceplate 351 has a-plurality of dovetails 353 extending posteriorly therefrom. Similarly, the anterior wall 355 of the cage 357 has a plurality of dovetail recesses therein extending from the upper surface 359 to the lower surface of the cage. The faceplate is top or bottom loaded into the cage so that the dovetails and corresponding recesses mate.

Figure 4V:
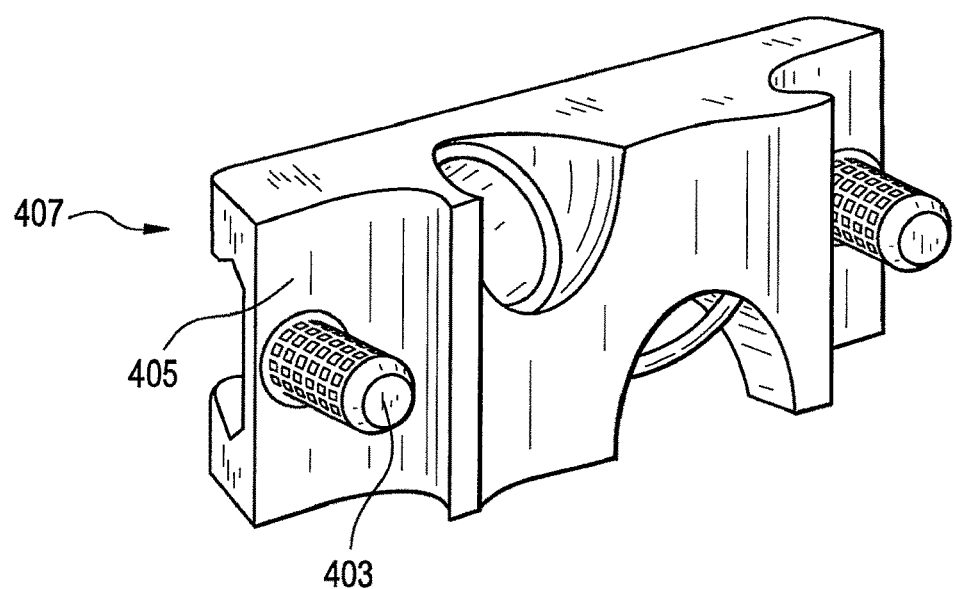

Now referring to FIG. 4V in some embodiments, the fixed connection of the present invention is accomplished by providing insertion pins 403 on the posterior wall 405 of the faceplate 407, along with aligned recesses on the anterior portion of the cage. The insertion pins are then cooled so that they contract. The insertion pins are then inserted into the aligned recesses in the anterior portion of the cage. Once the insertion pins warm, they expand and provide a secure friction fit.

In some embodiments, assembly of the two components could take place in the operating room due to the modularity of the design, thus allowing for intra-operative decision making.

As used herein, the term "bone graft" may include both synthetic bone (such as synthetic hydroxyapatite) and natural bone (such as allograft).

Fifth Aspect of the Invention

There is sometimes a need to re-operate on or revise a patient having an intervertebral spacer that has been secured in place by screws because the screw-spacer interface does not function as intended and so poses a risk of screw backout. Screw backout is a well known safety issue. Accordingly, the surgeon must often engage in extra surgical steps, such as passing another instrument through to the site and turning a cam or cover plate.

Figure 5A:
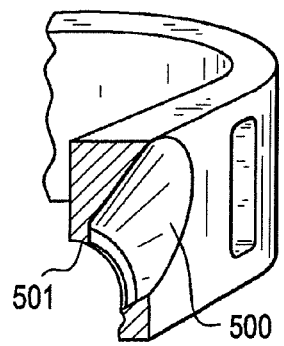
FIGS. 5A-5W disclose various embodiments and component of a stand alone cage having an anti-backout feature.
Figure 5B:
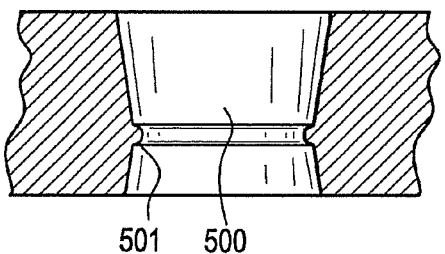
Figure 5C:
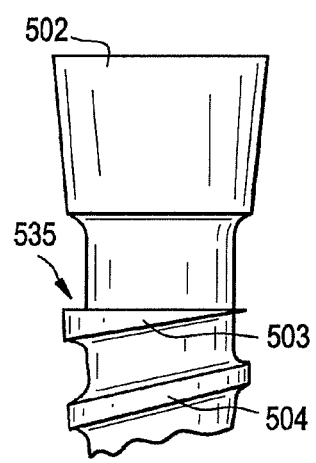

In accordance with the present invention, there is provided a stand alone intervertebral fusion device that provides enhanced securement of the screw to the spacer, and so prevents backout. The design incorporates securement features into the basic device design as part of the spacer's screw hole and as part of the basic screw, and so does not add additional components to the device that could increase profile and complexity. Now referring to FIGS. 5A-5B, the screw hole 500 includes a machined-in ring 501 that is at least partially (and preferably fully) circumferential and is fully contained within the screw hole. Now referring to FIGS. 5C-5E, as for the screw 502, the proximal end portion 503 of its thread 504 includes a proximal sidewall 535 that runs parallel to the ring. In use, the thread passes over the ring to allow passage of the screw into the hole. Once the screw is threaded into position so that the entire threadform has passed over the ring, the distal portion of the screw head proximally abuts the ring, thereby preventing further advance. In addition, if the screw were to begin backout, the last turn of the screw thread (i.e., the proximal end portion of the thread having the parallel sidewall) would soon abut against the ring, thereby preventing backout.

In some embodiments, the ring is sized to provide engagement with the root and/or side wells of the crest of the thread of the screw shank to allow for screw advancement. This mimics a helical threadform machined into the aperture, but need not be a helix.

Due to these design features, the interface between the screw and the spacer in these embodiments should have superior push out strength, ease of use and backout resistance (as compared to previous designs such as a bushing). This is because it is an integral machined-in lip with fewer failure modes. In addition, this design of the present invention will allow the surgeon to secure the screw in a single step-by simply advancing and bottoming out the screw in the spacer, thereby eliminating extra steps for the surgeon to perform. In addition, the design is robust in that it can accommodate rigid or variable screws and allow for controlled screw toggle depending on the surgeon's desire.

Therefore, in accordance with the present invention, there is provided an intervertebral device for insertion into a disc space defined by opposing vertebral endplates, comprising i) an intervertebral spacer comprising:

a) having an anterior wall having an upper surface and a lower surface, an anterior surface, and a first hole extending from the anterior surface to the upper surface and a second hole extending from the anterior surface to the lower surface, b) a posterior wall having an upper surface and a lower surface, and c) first and second side walls connecting the anterior and posterior walls, each side wall having an upper surface and a lower surface, ii) a first screw received in the first hole and having a distal tip, an intermediate shaft having a first thread, and a proximal head, iii) a second screw received in the second hole and having a distal tip, an intermediate shaft having a second thread, and a proximal head, wherein the anterior wall has a first hole surface having a first ring extending therefrom, wherein the first thread has a proximal end portion having a proximal side wall that runs substantially parallel to the ring.

Figure 5D:
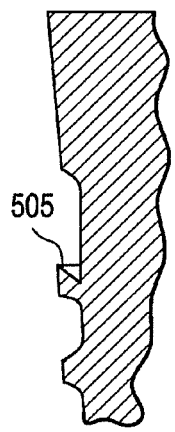
Figure 5E:
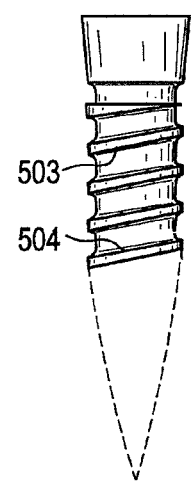

In some embodiments, the proximal end portion of the thread can have a contour selected from the group consisting of a straight cut 503 (as in FIG. 5C), a relief cut, or a reverse cut 505 (as in FIG. 5D).

Figure 5F:
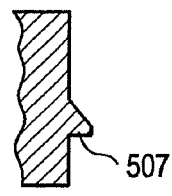
Figure 5G:
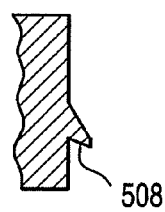
Figure 5H:
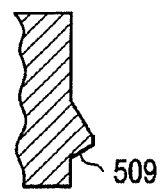

In some embodiments, the machined-in ring can have a contour selected from the group consisting of a straight cut 507 (as in FIG. 5F), a relief cut 509 (as in FIG. 5G) or a reverse cut 508 (as in FIG. 5H).

In some embodiments, the proximal end portion of the thread having the parallel sidewall includes substantially all of the run-out portion of the thread.

Figure 5I:
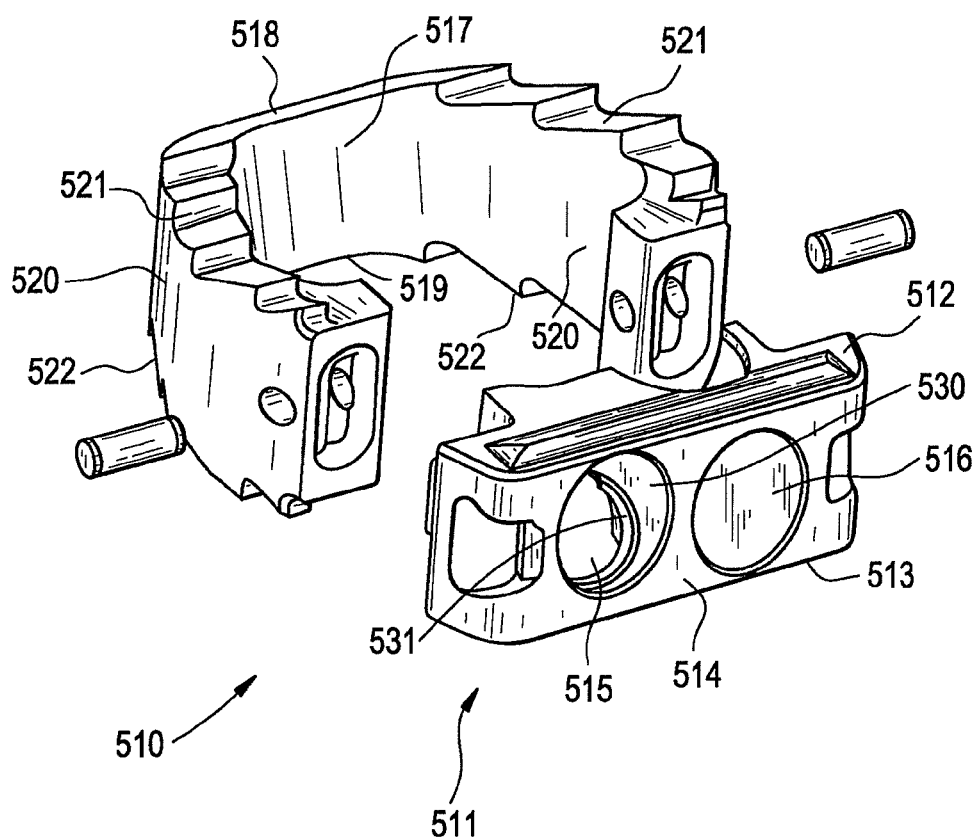
Figure 5J:
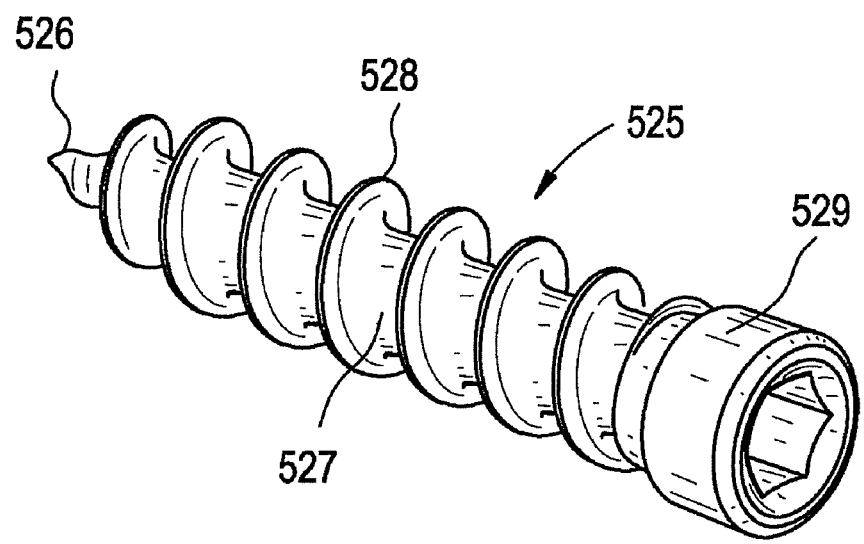
Figure 5K:
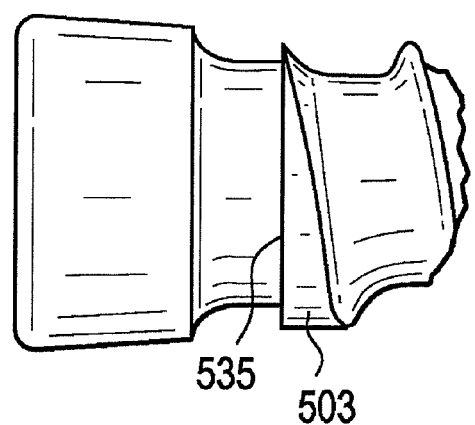

Therefore, and now referring to FIGS. 5I-5K, there is provided an intervertebral device for insertion into a disc space defined by opposing vertebral endplates, comprising i) an intervertebral spacer 510 comprising:

a) having an anterior wall 511 having an upper surface 512 and a lower surface 513, an anterior surface 514, and a first hole 515 extending from the anterior surface to the upper surface and a second hole 516 extending from the anterior surface to the lower surface, b) a posterior wall 517 having an upper surface 518 and a lower surface 519, and c) first and second side walls 520 connecting the anterior and posterior walls, each side wall having an upper surface 521 and a lower surface 522, ii) a first screw 525 received in the first hole and having a distal tip 526, an intermediate shaft 527 having a first thread 528, and a proximal head 529, iii) a second screw received in the second hole and having a distal tip, an intermediate shaft having a second thread, and a proximal head, wherein the anterior wall has a first hole surface 530 having a first ring 531 extending therefrom, wherein the first thread has a proximal end portion having a proximal side wall 535 that runs substantially parallel to the ring.

In some embodiments, the first ring abuts the proximal side wall to prevent backout. Preferably, the ring is sized to allow for passage of the first thread to allow for screw advancement. In some embodiments, the first ring is fully circumferential, while in others it is partially circumferential. In some embodiments, the first ring is an integral portion of the anterior wall. In some embodiments, the first ring is manufactured separately from the anterior wall.

Thus, the present invention generally relates to a medical implant comprising:

a) a wall having an upper surface and a lower surface, and a front surface, and a first hole extending into the wall from the front surface,
b) a first screw received in the first hole and having a distal tip, an intermediate shaft having a first thread, and a proximal head,
wherein the wall has a first hole surface having a first ring extending therefrom,
wherein the first thread has a proximal end portion having a proximal sidewall that runs substantially parallel to the ring.

Likewise, the method of using the present invention generally relates to a method of fixing an implant comprising a wall having a front surface and a first hole extending into the wall from the front surface, wherein the wall has a first hole surface having a first ring extending therefrom, the method comprising the steps of:
a) placing the implant against a bone, and
b) selecting a first screw having a distal tip, an intermediate shaft having a first thread, and a proximal head, wherein the first thread has a proximal end portion having a proximal sidewall that runs substantially parallel to the ring,
c) inserting a first screw through the first hole and into the bone.

In some embodiments, the first screw is inserted into the bone so that the proximal end portion of the first thread is advanced past the ring. In some embodiments, the first screw is inserted into the bone so that the ring is disposed between the proximal end portion of the first thread and the proximal head. In some embodiments, the length of this neck portion can be varied depending on the level of desired compression.

Figure 5L:
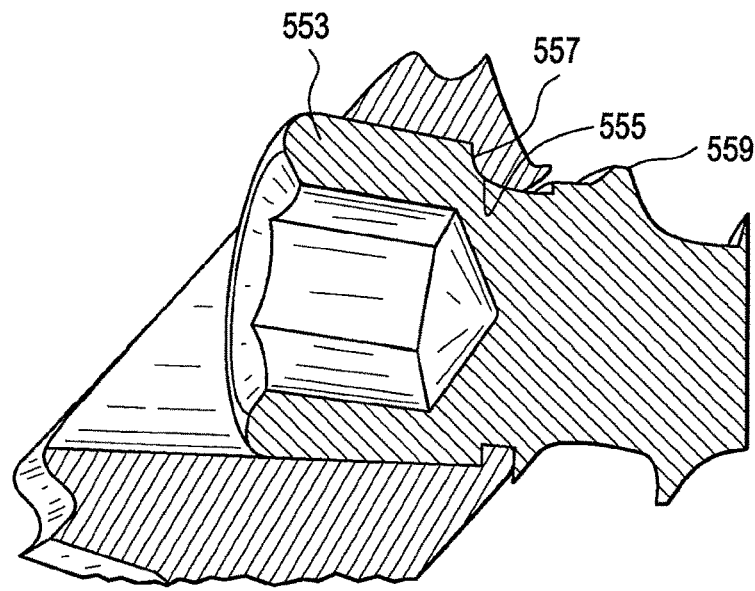
Figure 5M:
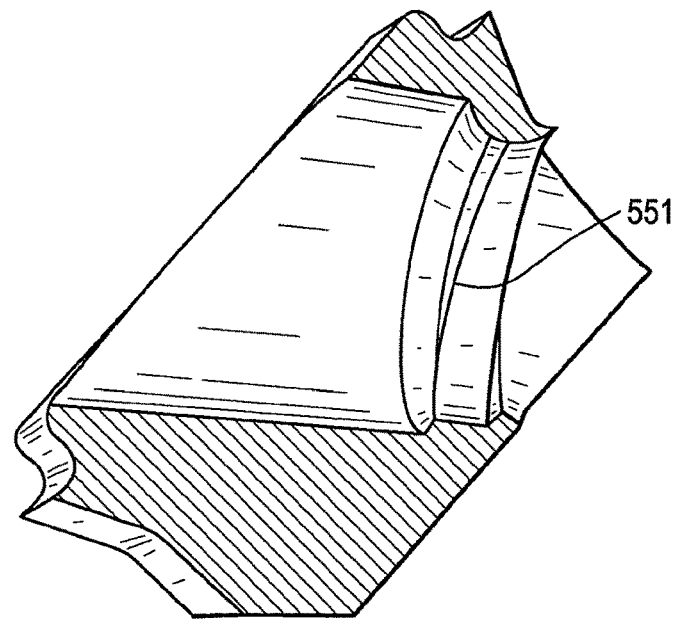
Figure 5N:
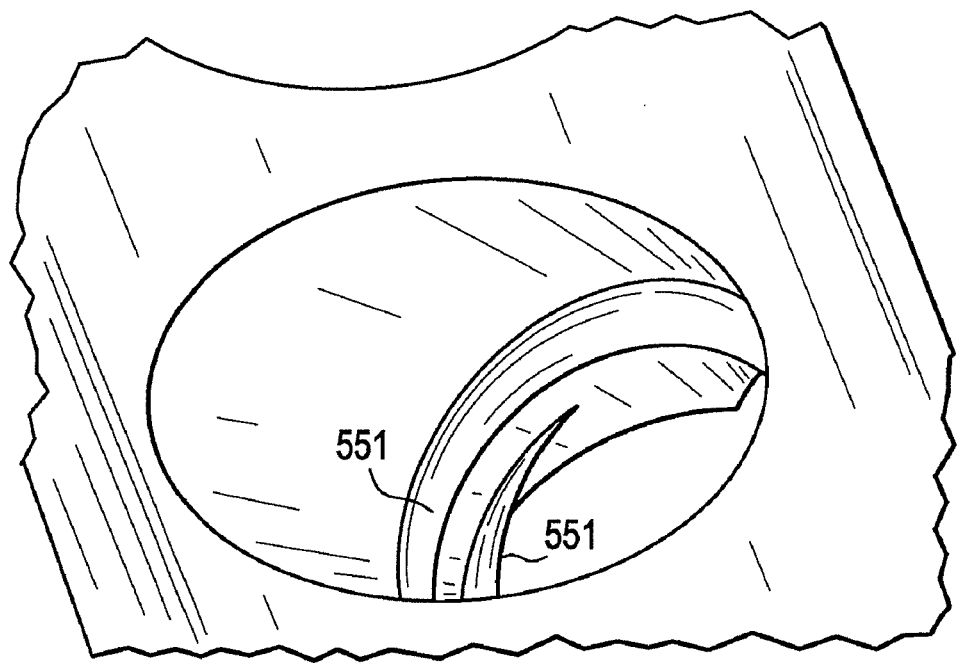
Figure 5O:
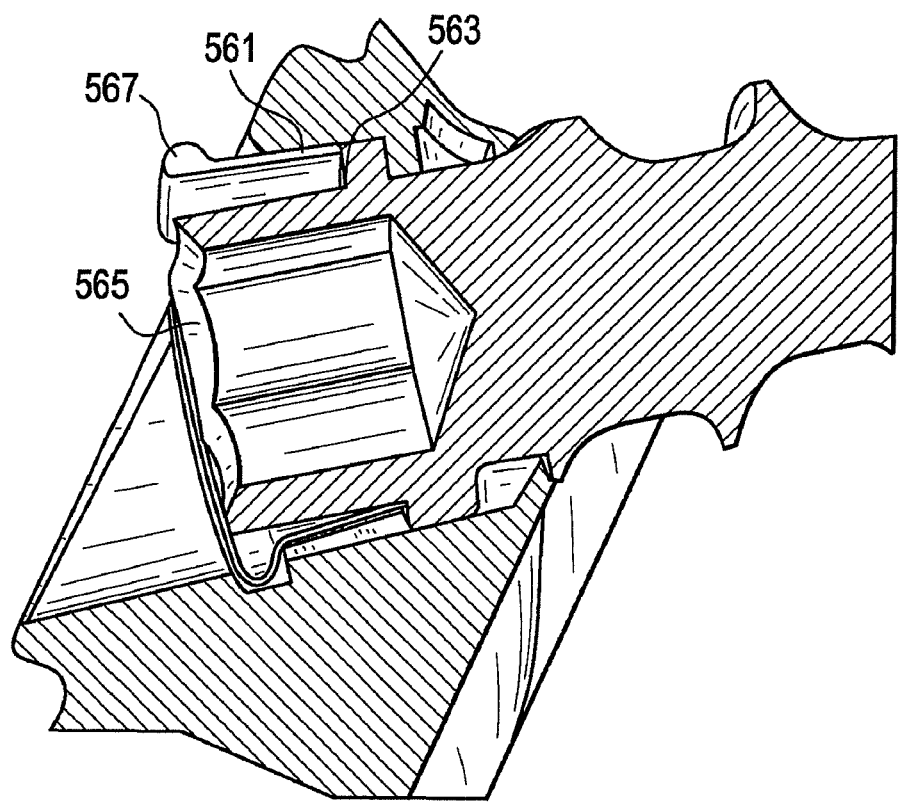
Figure 5P:
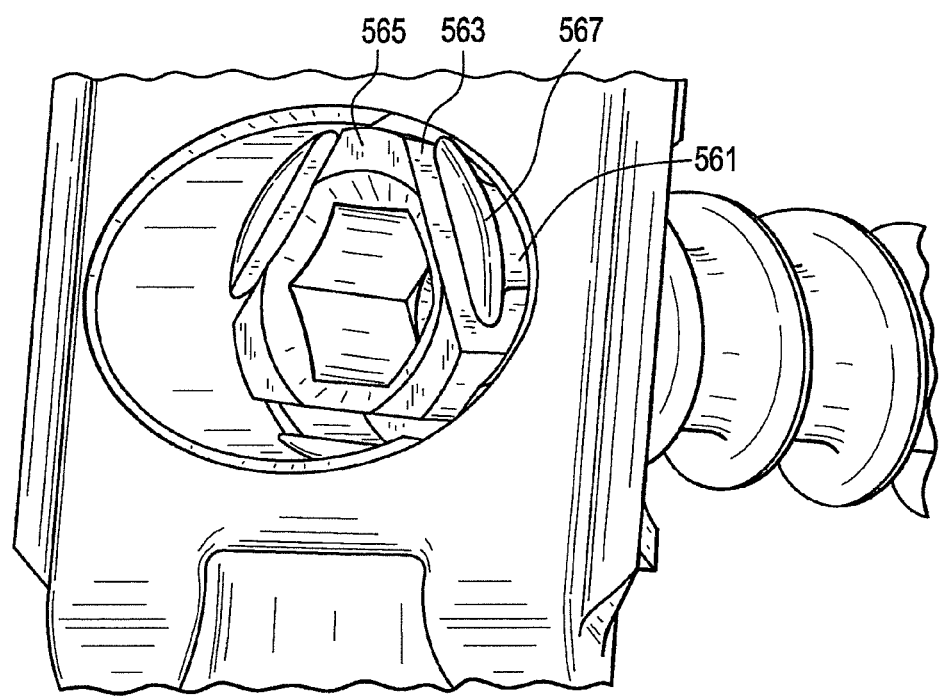
Figure 5Q:
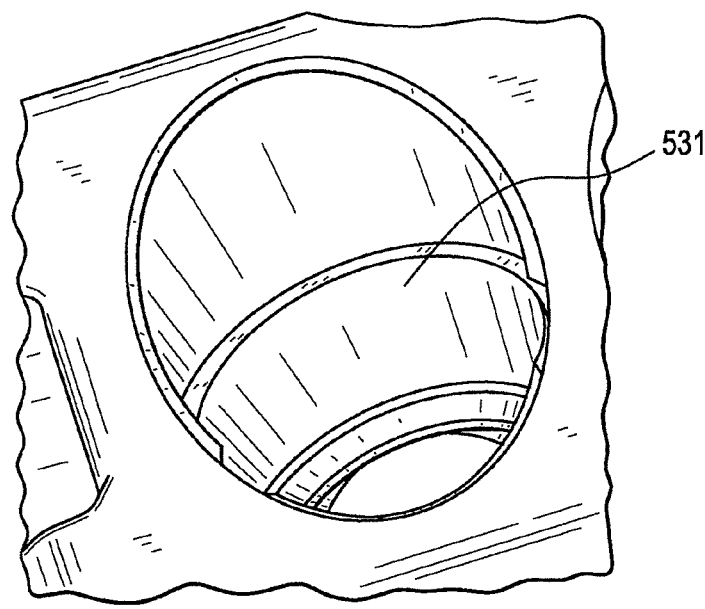
Figure 5R:
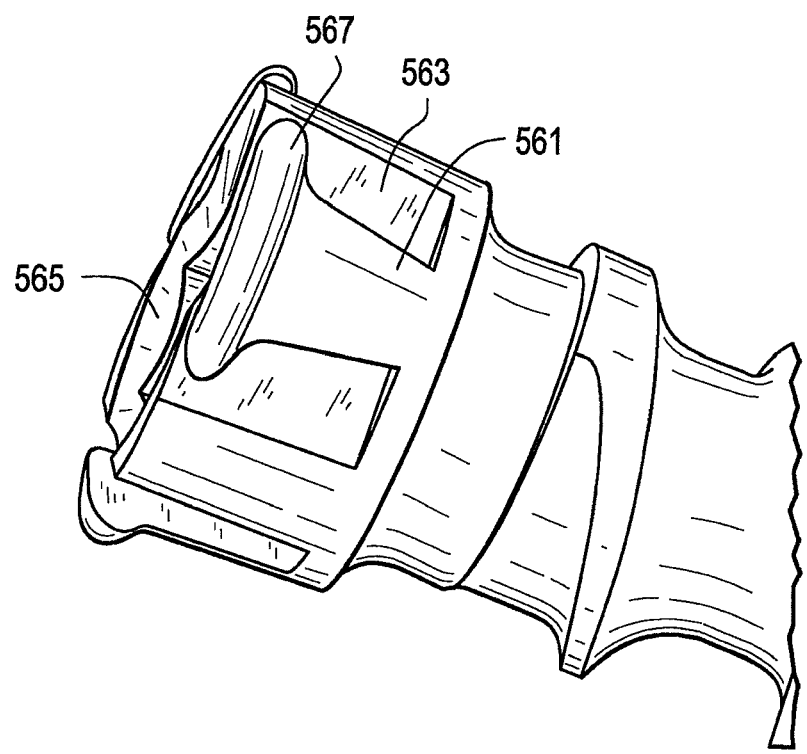
Figure 5S:
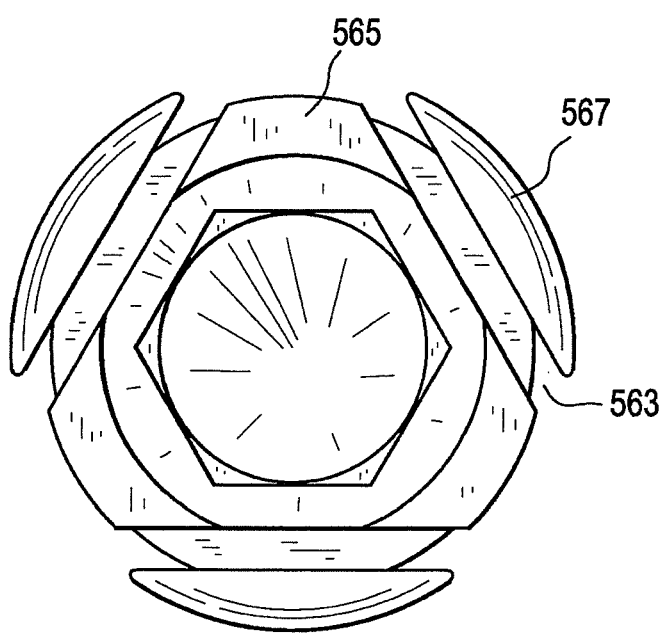
Figure 5T:
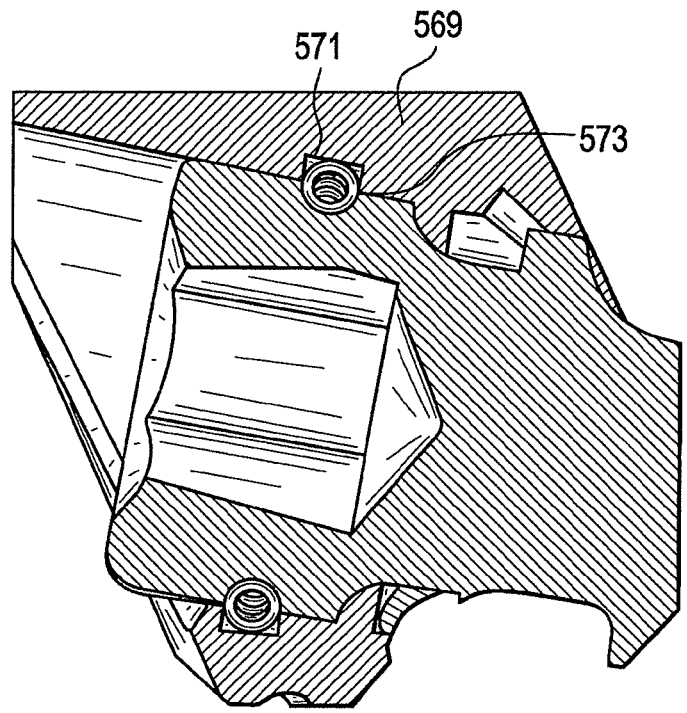
Figure 5U:
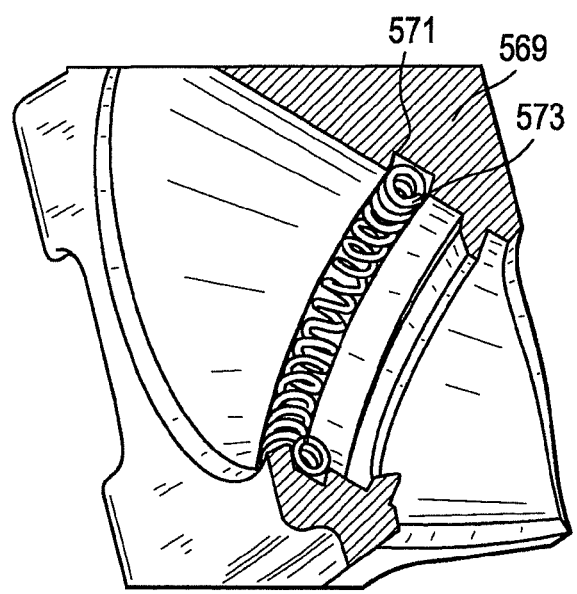
Figure 5V:
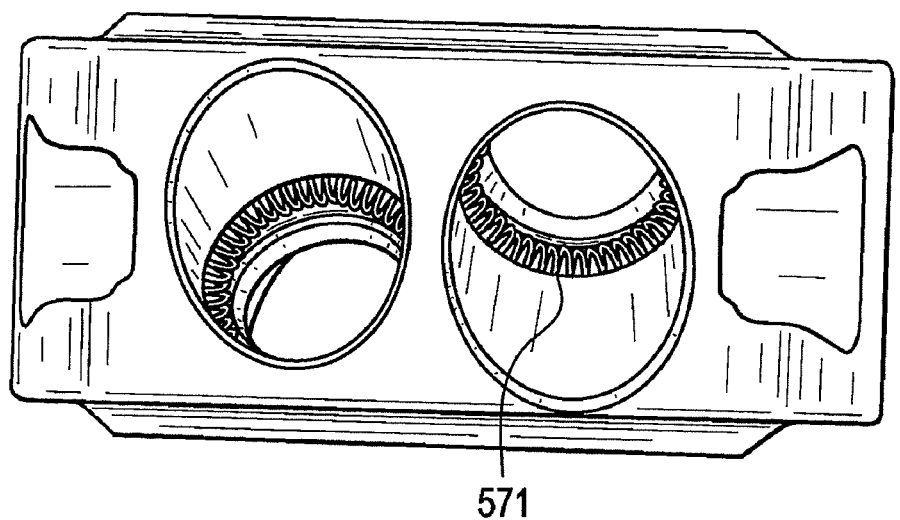
Figure 5W:
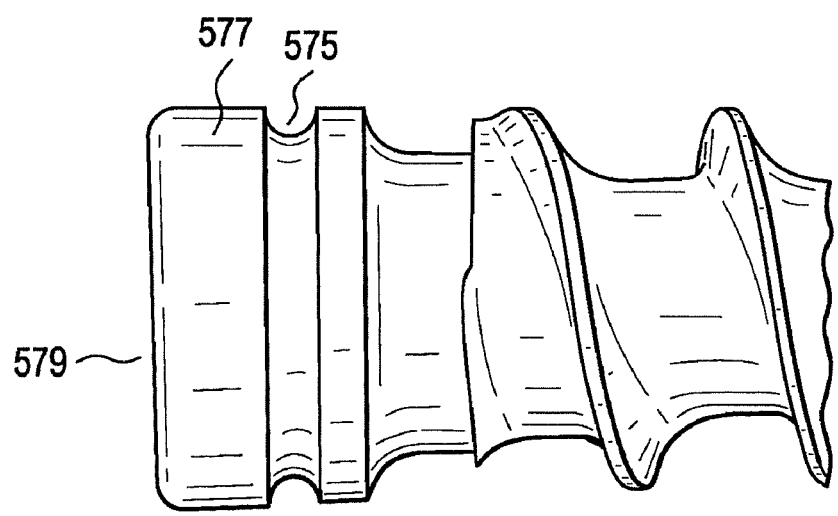

Now referring to the anti-backout embodiment of FIGS. 5L-5N, there is a helical ring 551 to prevent the screw 553 from backing out after insertion. The pitch and shape of the helical ring matches that of the screw so that the screw can be easily inserted. Once the screw has been fully inserted the bottom of the screw head 555 will be in contact with the top 557 of the helical ring. At this point all of the threads 559 on the screw will have fully passed through the helix on the faceplate and the helix will reside between the bottom of the screw head and the end of the last thread on the screw. In order to remove the screw, the threads would have to be re-engaged with the helix. An axial load would not allow the screw to backout once the screw is properly inserted.

Now referring to FIGS. 5O-5S, this anti-backout embodiment comprises a) multiple spring tabs 561 that are formed from recesses 563 cut into the distal surface 565 of the head of the screw and b) a mating groove in the faceplate. When the screw is inserted into the bone, the bottom of the screw head pushes against a continuous ring so that it cannot go through the face plate. At the same time, protrusions 567 on the screw head spring tabs pop into the mating groove on the faceplate to prevent the screw from being able to back out of the faceplate.

Now referring to FIGS. 5T-5W, in this embodiment anti-backout is achieved through the use of a balseal 569. A groove 571 is cut into the faceplate in which a circular spring 573 is placed. Another groove 575 is cut into the head 577 of the screw 579. When the screw is inserted, the bottom of the head will become fully seated against a ring in the faceplate. At this time, the geometry of the head of the screw will have flattened out the spring and once fully seated the spring will recover to its normal position and be housed in the groove on the head of the screw thereby preventing the screw from backing out. The geometry on the head of the screw can be designed so that a minimal amount of force (such as one pound) is required to lock the screw into the spring but a greater force (such as 25 pounds) is required to removed the screw from the balseal.

Sixth Aspect of the Present Invention

After performing an anterior approach discectomy and insertion of a spacer/cage, some spine surgeons prefer not to insert a plate on the anterior surface of a patient with fixation through the anterior face of the cephalaud and caudal vertebral bodies. Often times, the plate can be considered to be too proud and its profile can sometimes cause patient discomfort and cause dysphasia.

Disclosed is a method of securing an intervertebral fusion cage to an intervertebral disc space with fixation elements, and numerous implant embodiments therefor. After the cage is placed and positioned per the surgeon preference, the fixation elements (such as fins, pins, blades, plates, keels, and hooks) are inserted up against a proximal face of the cage. The fixation elements are inserted into the cage in an orientation substantially perpendicular to the proximal face of the cage, and substantially in-line with the inserter. The fixation elements are then deflected outward from the cage during insertion by a sloped feature on the anterior surface of the cage. Preferably, this sloped feature is a tapered section defining an upward sloping surface and a downward sloping surface. Ideally, the deflected fixation elements penetrate the adjacent vertebral bodies and are secured in place with a compression cap.

Once placed in their desired locations, the fixation elements may further provide compression onto the cage. The fixation elements are preferably made of materials and possess shapes designed to accomplish this function. Materials that preferably allow the fixation elements to accomplish this compression function include metals such as stainless steel and titanium alloy, polymers, autograft, allograft, ceramics, and resorbable materials such as HA and TCP. Geometries that preferably allow the fixation elements to accomplish this compression function include those provided in FIGS. 6A-6W.

The fixation cage of the present invention allows the surgeon to create a smaller incision and access site for the cage and fixation elements because direct access that is parallel to the disc space is provided. The in-line insertion of the fixation elements also allows the surgeon to avoid having to insert the fixation elements on a high angle through sometimes challenging approaches.

Figure 6A:
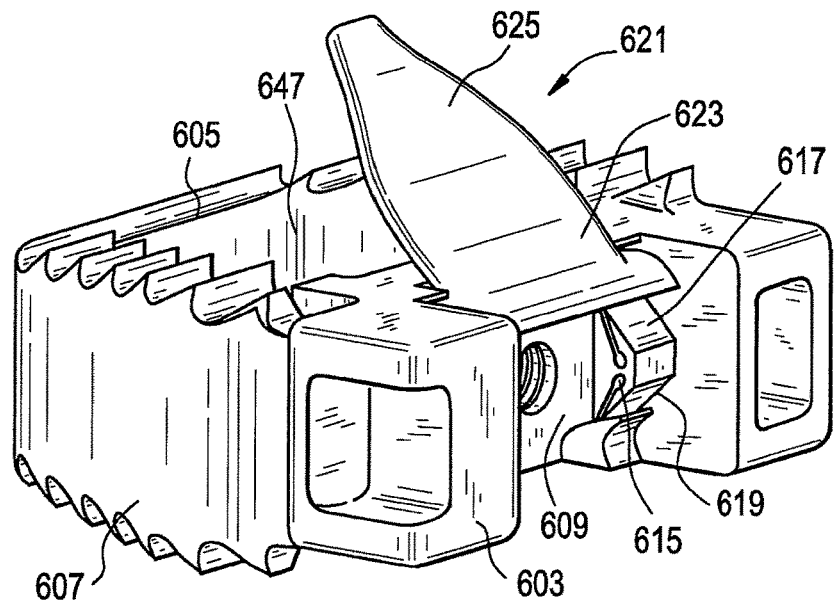
FIGS. 6A-6I discloses various embodiments and components of a stand alone cage having fins.
Figure 6B:
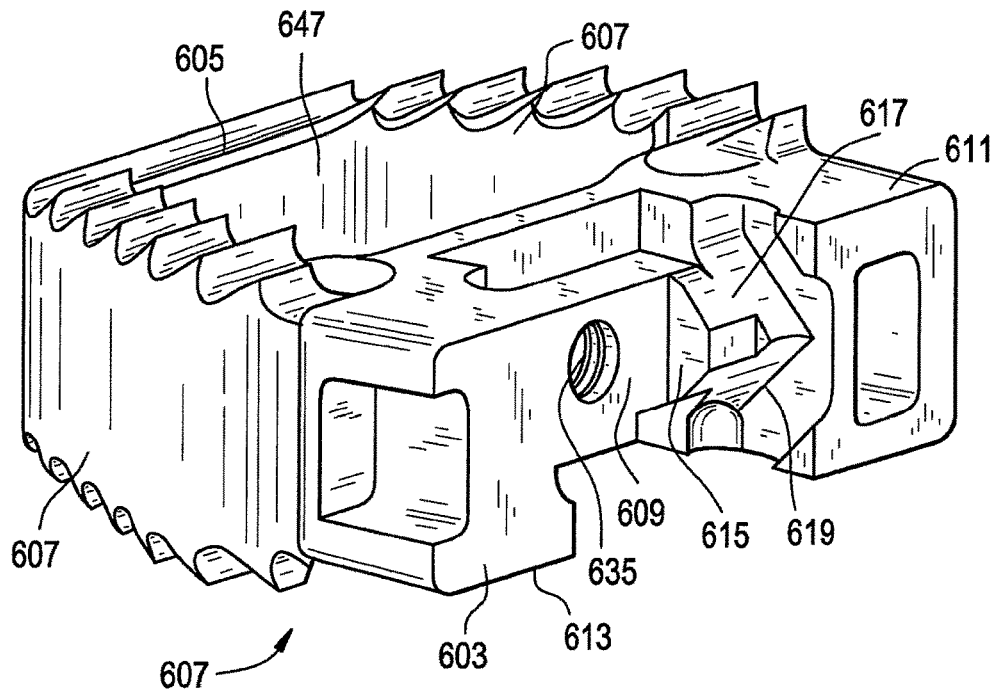
Figure 6C:
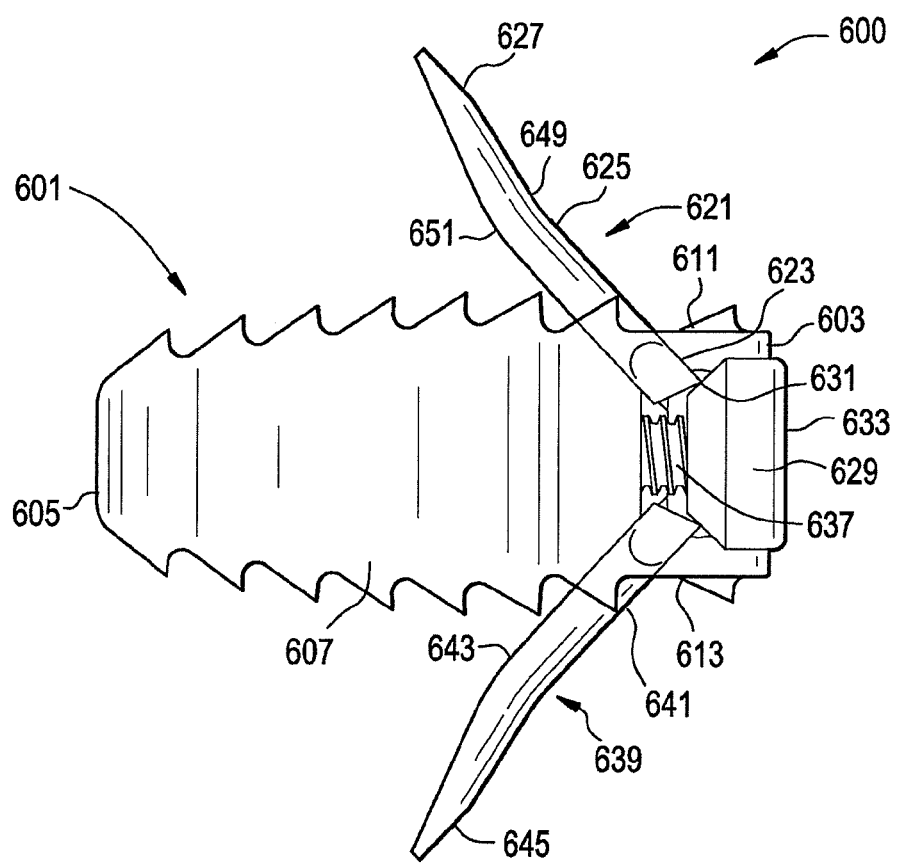

Now referring to FIG. 6A-6C, there is provided, an intervertebral implant 600 comprising:
a) an intervertebral spacer 601 having an anterior wall 603, a posterior wall 605, and first and second side walls 607 connecting the anterior and posterior walls, the anterior wall having an anterior surface 609, an upper surface 611 and a lower surface 613, wherein the anterior surface has a tapered section 615 defining an upward sloping surface 617 and a downward sloping surface 619,
b) a first fin 621 having a proximal section 623, an intermediate section 625 and a distal section 627,
c) a compression cap 629 having a first portion 631 and a second portion 633, wherein the first fin contacts the upward sloping section of the tapered section of the anterior face,
wherein the distal section of the first fin extends above the upper surface of the anterior wall, and
wherein the proximal section of the first fin contacts the first portion of the compression cap.

In some embodiments, the anterior wall further comprises a threaded hole 635 located between the upward and downward sloping surfaces thereof, wherein the compression cap comprises a distal thread 637, and wherein the threaded hole threadably receives the thread of the compression cap. This threaded connection provides a reliable means of securing the fins to the cage.

In some embodiments, there is provided a second fin 639 having a proximal section 641, an intermediate section 643 and a distal section 645, wherein the second fin contacts the downward sloping section of the tapered section of the anterior face, wherein the distal section of the second fin extends below the lower surface of the anterior wall, and wherein the proximal section of the second fin contacts the second portion of the compression cap. The second fin provides for bilateral fixation of the cage between the opposing vertebral bodies.

In some embodiments, the spacer further comprises a hollow portion 647 between the anterior and posterior walls, wherein bone graft is contained within the hollow, and wherein the fins impart compression onto the bone graft. Thus, the fins provide an additional benefit of bone graft compression to the device.

In some embodiments, the first fin comprises a concave surface 649 and an opposing convex surface 651. These surfaces provide the fin with an upward or downward curve that allows the fin to enter the opposing vertebral bodies in an orientation more perpendicular to the endplates.

In some embodiments, the convex surface of the first fin contacts the upward sloping surface of the tapered portion of the anterior surface of the anterior wall. This allows the upward sloping surface to determine the angle of the fin as it extends into the vertebral body.

Figure 6D:
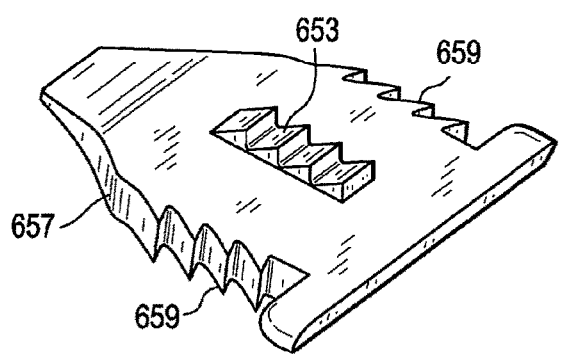

Now referring to FIG. 6D, in some embodiments, wherein at least one of the concave and convex surfaces of the first fin has a tooth 653 extending therefrom. These teeth provide additional fixation character to the fin. Preferably, at least one of the concave and convex surfaces of the first fin has a plurality of teeth extending therefrom.

Figure 6E:
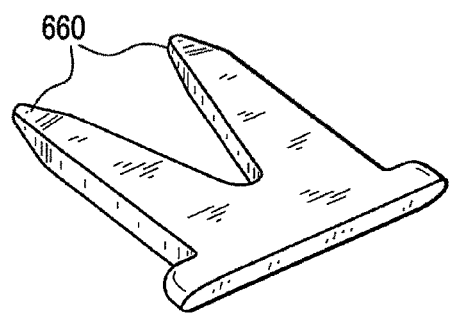
Figure 6F:
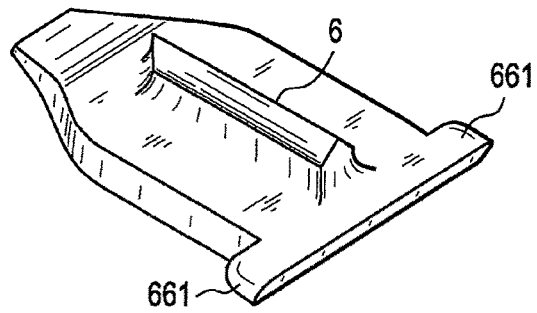
Figure 6G:
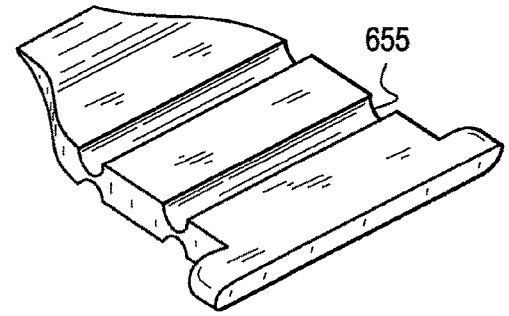

Now referring to FIG. 6G, in some embodiments, at least one of the concave and convex surfaces of the first fin has a groove 655 therein. This groove provides additional fixation character to the fin, or may be designed to allow for intentional bending/flexing to occur.

Now referring to FIG. 6D, in some embodiments, the first fin further comprises at least one side surface 657 extending between the concave and convex surfaces, wherein the at least one side surface comprises a tooth 659 thereon. These teeth provide additional fixation character to the fin.

Now referring to FIG. 6E, in some embodiments, the distal section of the first fin comprises at least two tynes 660 forming a fork. The fork provides two points of fixation and may provide a benefit when existing hardware from a previous surgery is in the space.

Now referring to FIG. 6F, in some embodiments, the proximal portion of the first fin has wings 661 extending laterally therefrom. The wings provide a stop and a pivot point. In some embodiments, thereof, the wings are flexible so as to provide rentention into the tapered anterior wall surfaces.

Figure 6H:
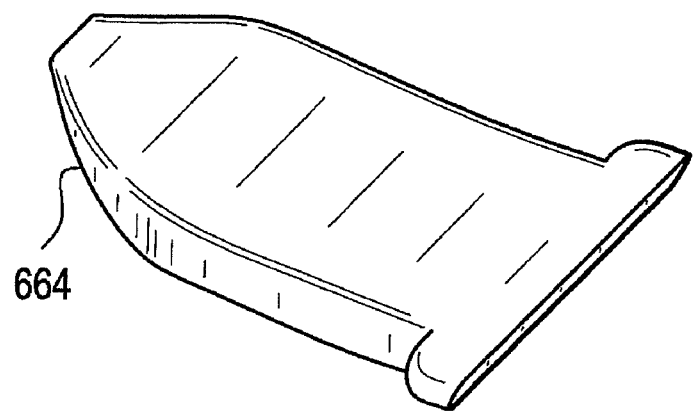

Now referring to FIG. 6H, in some embodiments, the distal portion of the first fin is tapered 664. The taper provides ease of insertion into the bone segment. In some embodiments, the embodiment of FIG. 6H can have a plurality of throughholes running transverse to the fin, as shown in FIG. 6X. In this embodiment there are a series of geometrically patterned holes 681 that pass through the fixation blade. These through holes allow spaces for bone to grow through the blades and provide a more solid fixation and a more complete fusion. These blades or at least the holes could have an osteo-conductive coating to help initiate this bone growth.

Figure 6I:
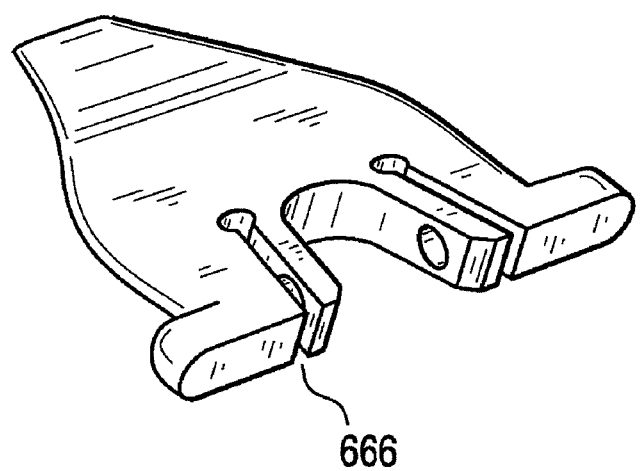
Figure 6J:
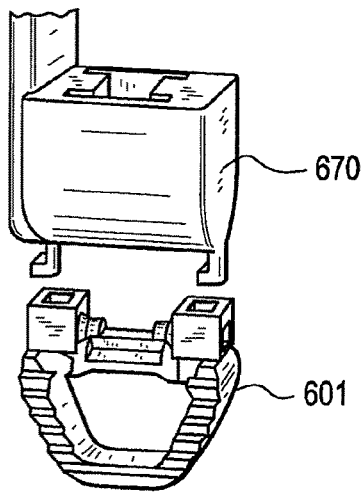
FIGS. 6J-6U disclose a method of implanting a stand alone cage of the present invention.
Figure 6K:
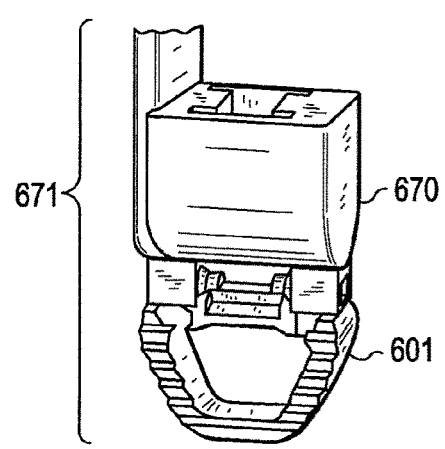
Figure 6L:
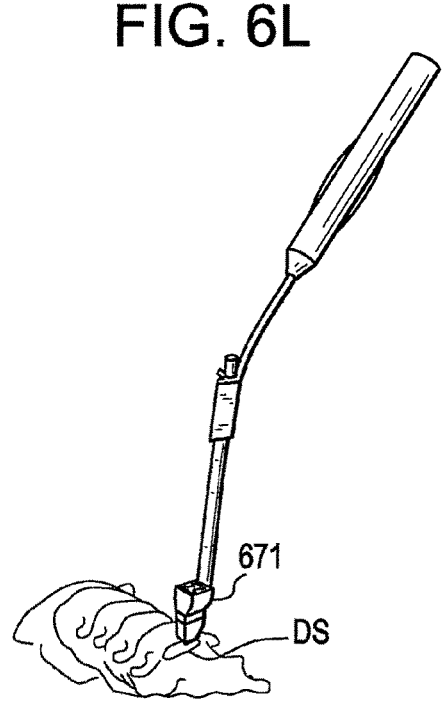
Figure 6M:
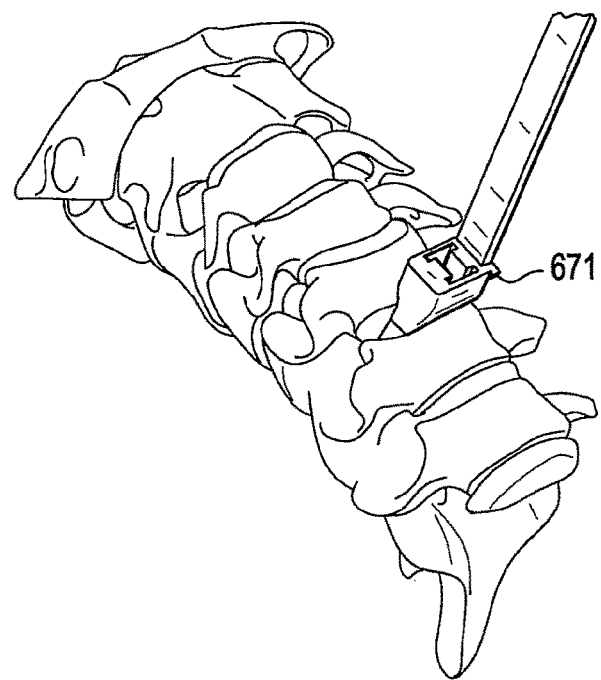
Figure 6N:
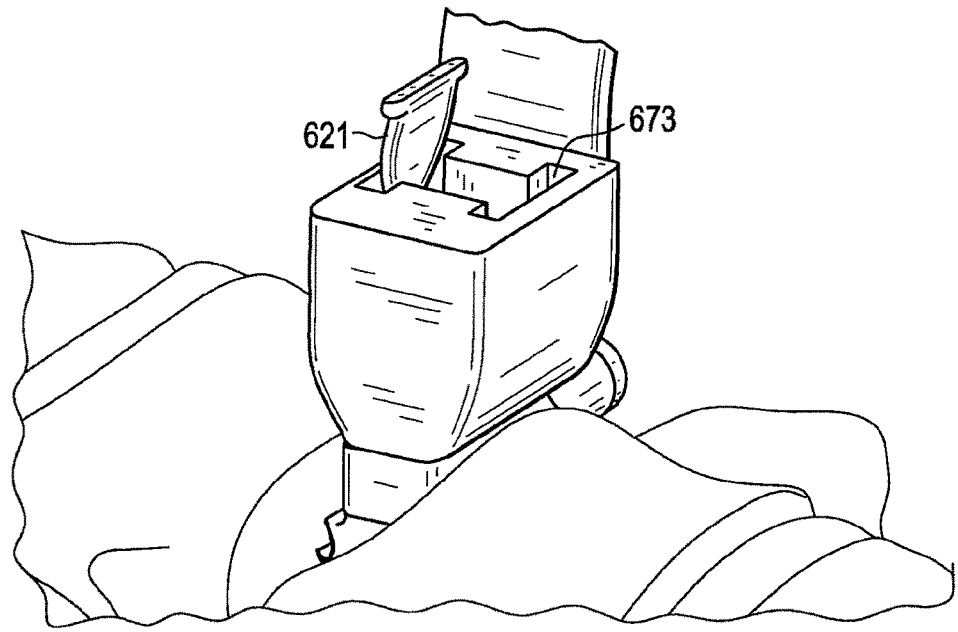
Figure 6O:
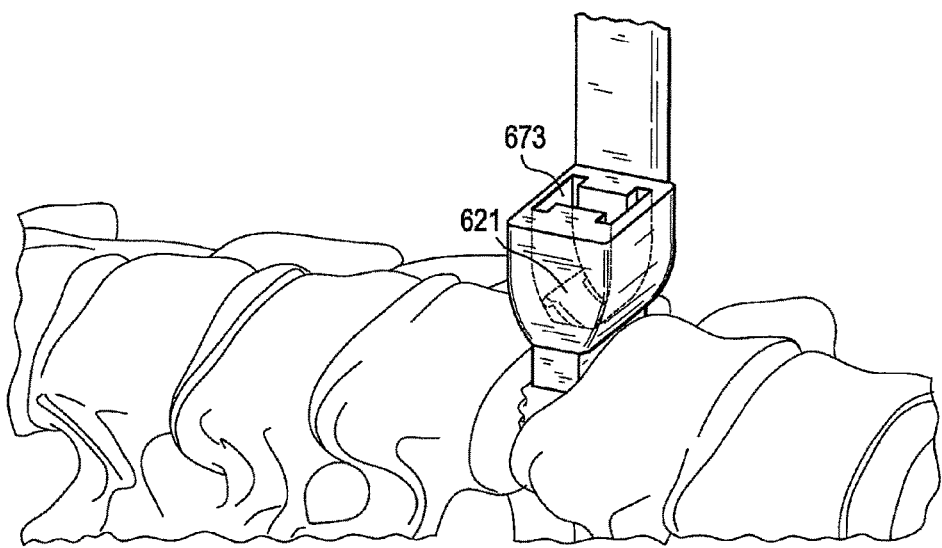
Figure 6P:
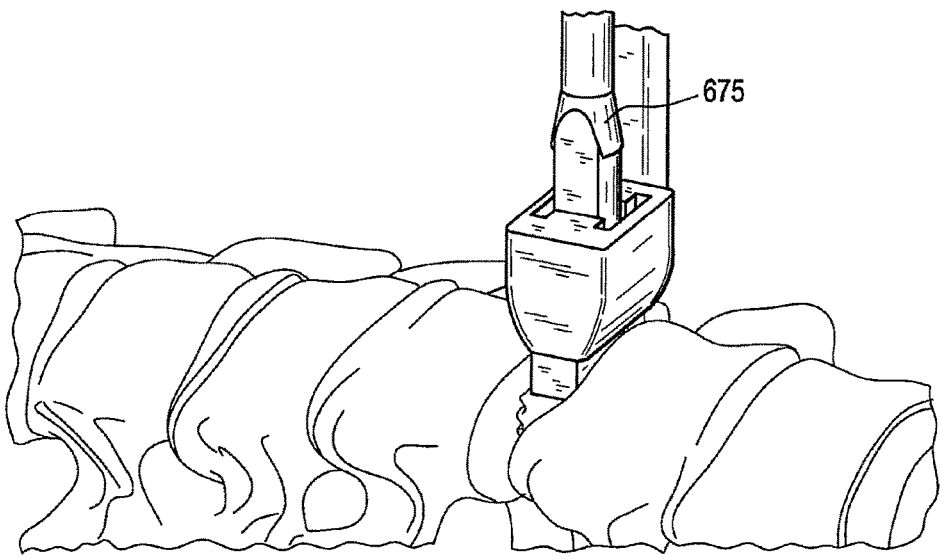
Figure 6Q:
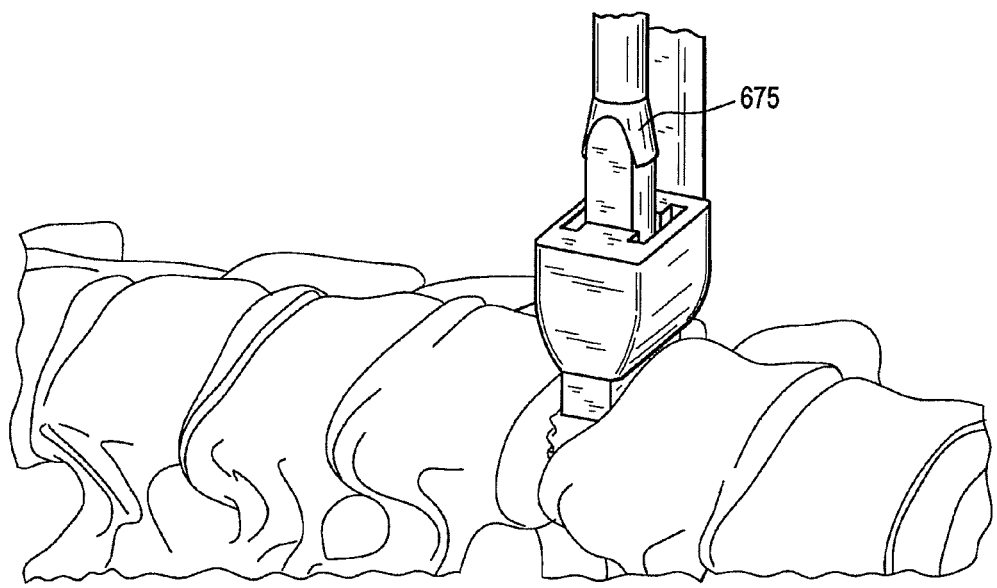
Figure 6R:
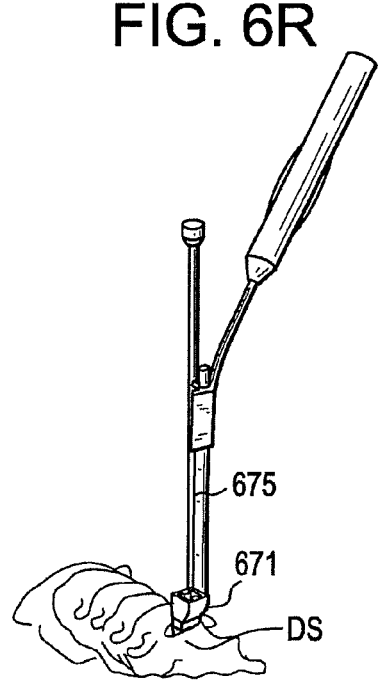
Figure 6S:
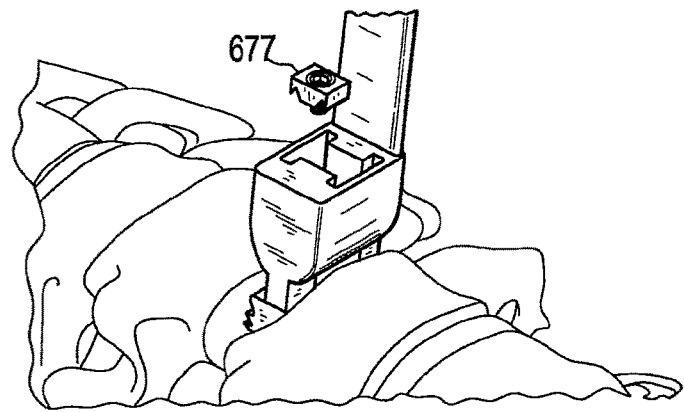
Figure 6T:
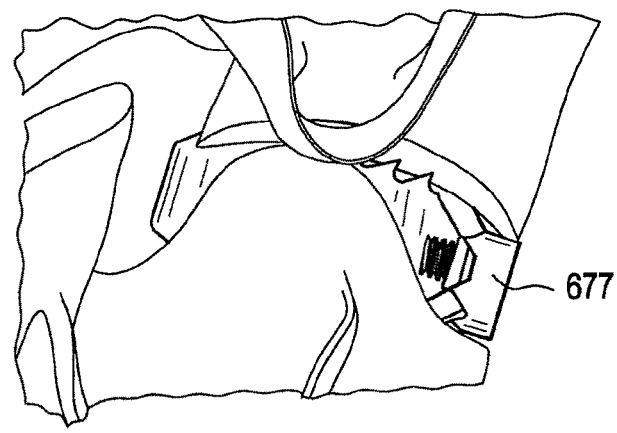
Figure 6U:
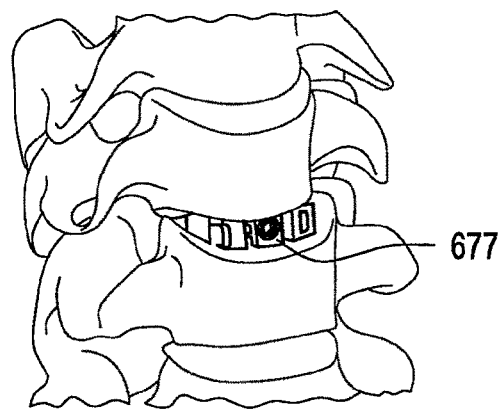

Now referring to FIG. 6I, in some embodiments, the proximal portion of the first fin has a longitudinal groove 666 therein to provide flexibility and/or retention.

In some embodiments, the proximal section of the first fin contacts the upward sloping section of the tapered section of the anterior face. In some embodiments, the intermediate section of the first fin contacts the upward sloping section of the tapered section of the anterior face.

In some embodiments, the first fin extends above the upper surface of the anterior wall at an angle defined by the upward sloping section of the anterior wall. This allows the angle at which the fin extends into the vertebral body to be predetermined by the implant.

In some embodiments, at least of the anterior wall, posterior wall, and first and second side walls of the intervertebral spacer further comprise an upper surface 663 and a lower surface 665 that are toothed 667. These teeth provide additional fixation of the cage to the vertebral bodies. In some embodiments, each of the anterior wall, posterior wall, and first and second side walls of the intervertebral spacer further comprise upper and lower surfaces that are toothed.

Figure 6V:
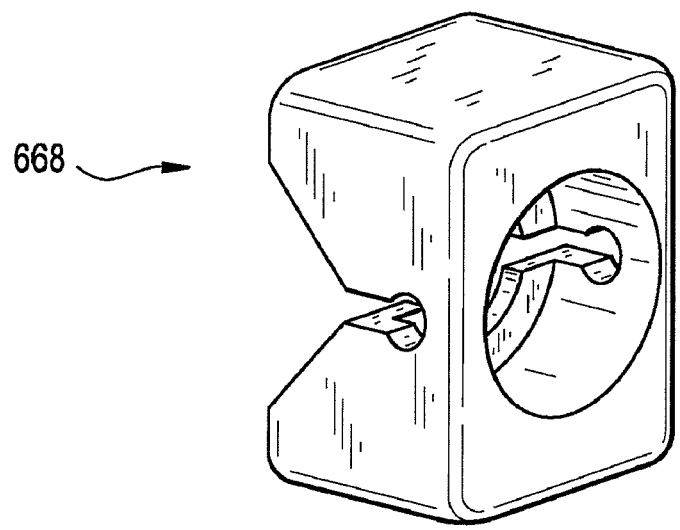
FIGS. 6V-6X discloses various components of a stand alone cage having fins.
Figure 6W:
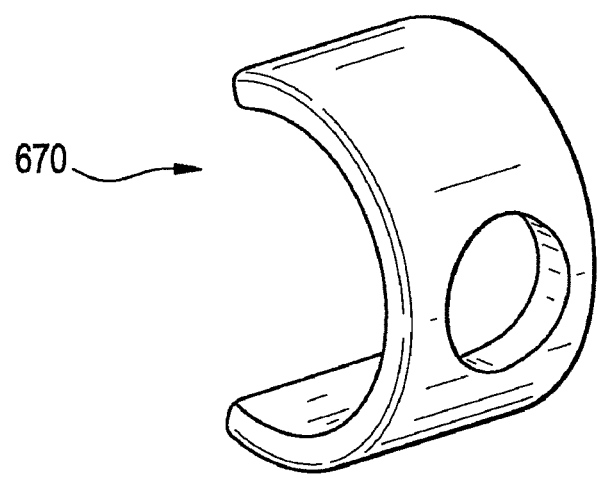
Figure 6X:
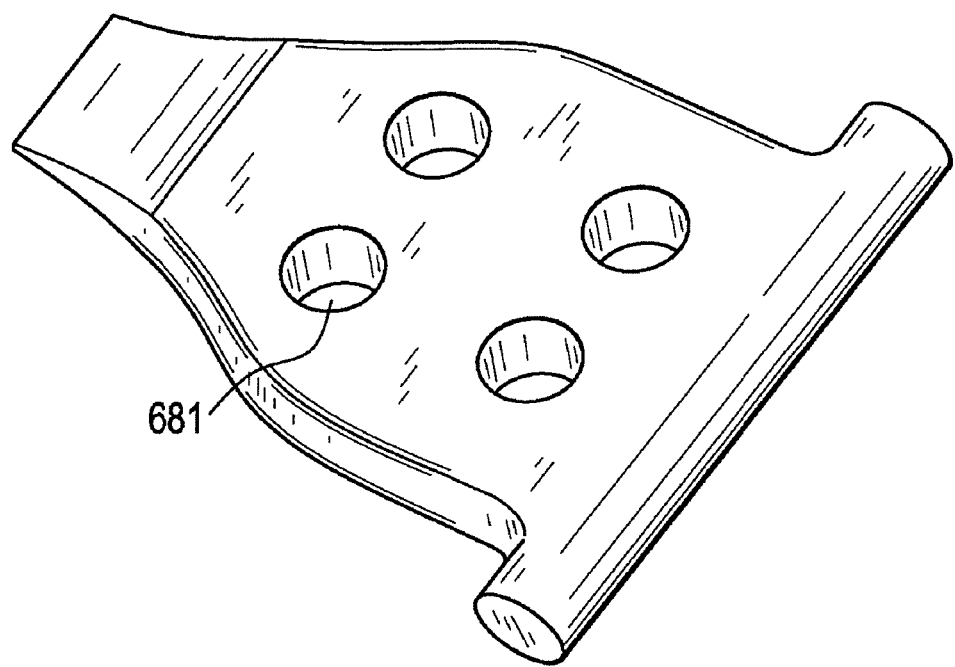

FIGS. 6V and 6W disclose are alternate embodiments of a compression cap for the blade version. Both would have a fastener (i.e, a screw) that would pass through it and would attach to the opening on the anterior face of the cage. FIG. 6V discloses cap 668 and FIG. 6W discloses cap 670.

The insertion of the cage of the present invention may follow the following procedure. Now referring to FIG. 6J, there is provided the spacer 601 of the present invention adjacent insertion device 670. Now referring to FIG. 6K, the spacer is attached to the insertion device to form assembly 671. Now referring to FIGS. 6L and 6M, the assembly is inserted into intervertebral disc space DS. Now referring to FIGS. 6N and 6O, first fin 621 is inserted into a groove 673 of the insertion device. Now referring to FIG. 6P-6R, the fin is pressed into place with inserter rod 675. Now referring to FIG. 6S-6U, compression cap 677 is inserted into the assembly to lock the fin to the spacer.

Although the cages of the present invention are preferably suited for use in the cervical spine, they may also be used in the lumbar and thoracic spine as well.

Although the cages of the present invention are preferably suited for use with a pair of bone screw, they may also be used with more than two fasteners. In some cases, the cage of the present invention is fastened with three bone screws provided in either a "one up/two down" or "two up/one down" arrangement.

Figure 7A:
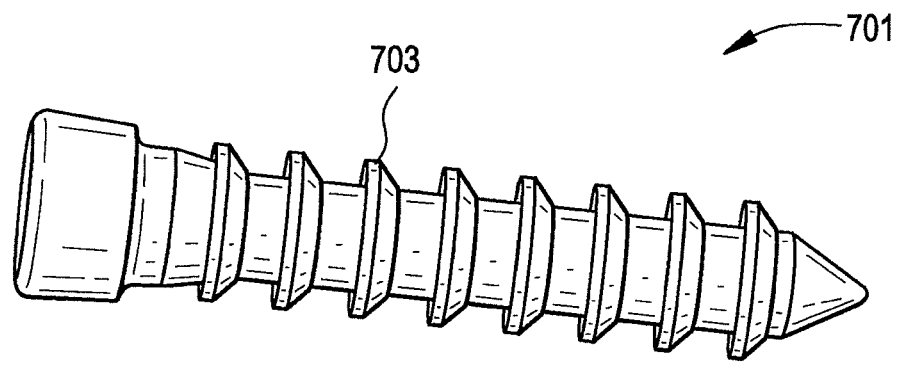
FIG. 7A-7B disclose barbed bone anchors of the present invention.
Figure 7B:
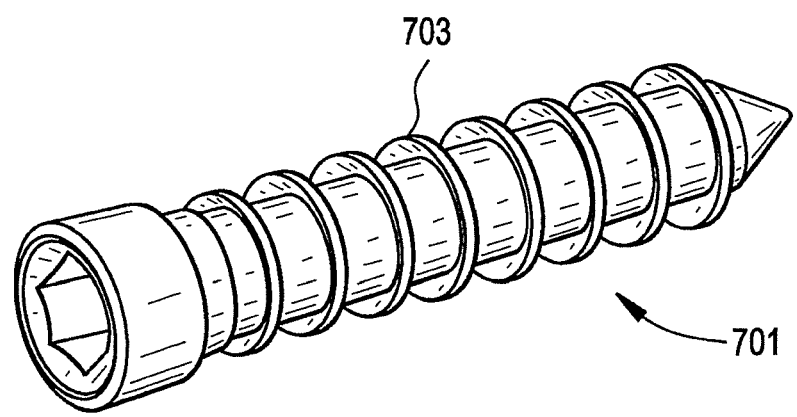

In some embodiments, and now referring to FIGS. 7A and 7B, the screw 701 used with fusion cages of the present invention is modified wherein the thread of the screw is replaced with substantially circumferential ribs 703 or barbs. In these embodiments, the device uses fins, barbs, or ribs as opposed to a threaded means for its fixation strength. This device can be tapped into a predrilled hole instead of threaded. This can lead to a faster and easier insertion of the fixation device without the risk of stripping out a threaded hole and losing fixation strength. The number of barbs and the geometry of the barbs can be designed to get the best fixation strength possible while requiring less force for insertion.

In some embodiments, the spacer comprises bone extending continuously between the anterior and posterior walls, and wherein the fins impart compression to the bone.

Seventh Aspect of the Invention

Figure 8:
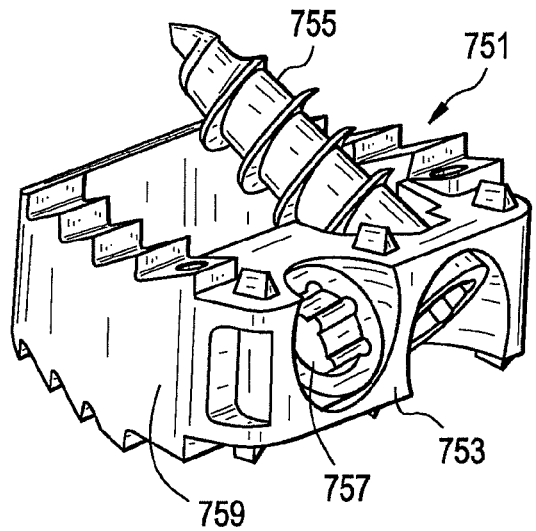
FIG. 8 discloses a fusion device wherein the posterior wall and the first and second side walls form an integral body.

Now referring to FIG. 8, there is provided an intervertebral fusion device of the present invention, comprising:
i) an intervertebral spacer 751 comprising:
   a) an anterior wall 753 having an upper surface and a lower surface, an anterior surface, and a first through-hole extending upwards from the anterior surface and a second throughhole extending downwards from the anterior surface,
   b) a posterior wall having an upper surface and a lower surface, and
   c) first and second side walls connecting the anterior and posterior walls, each side wall having an upper surface and a lower surface,
ii) a first bone anchor 755 received in the first through hole,
iii) a second bone anchor 757 received in the second through hole,
wherein the posterior wall and the first and second side walls form an integral body 759.

Figure 9:
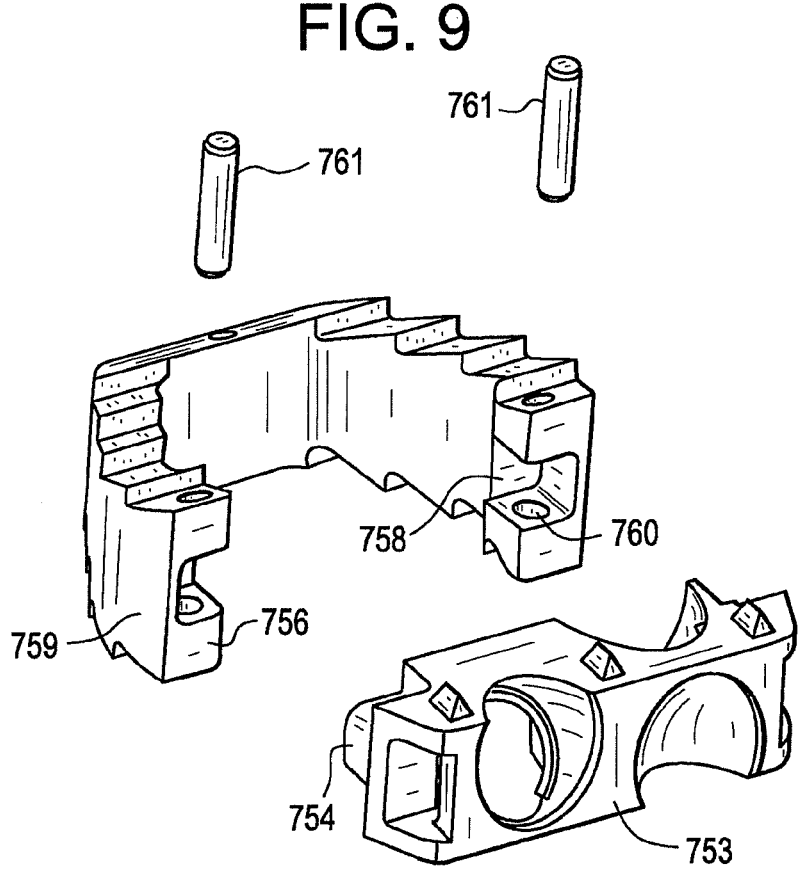
FIG. 9 discloses an exploded view of the intervertebral fusion device of FIG. 8 wherein the integral body and the anterior wall are connected by a pair of pins.

In one embodiment, the two pieces of the spacer have interlocking surfaces that are connected by transverse pins. FIG. 9 discloses an exploded view of the spacer of FIG. 8 wherein the integral body 759 and the anterior wall 753 are connected by a pair of pins 761. The anterior wall 753 has tongue features 754 having holes therein, while the anterior portion 756 of the integral body has groove features 758 having holes 760 therein, wherein the holes align when the tongue and groove interlock and receive the pins.

In other embodiments, these components may be assembled with a one-way snap feature.

Figure 10:
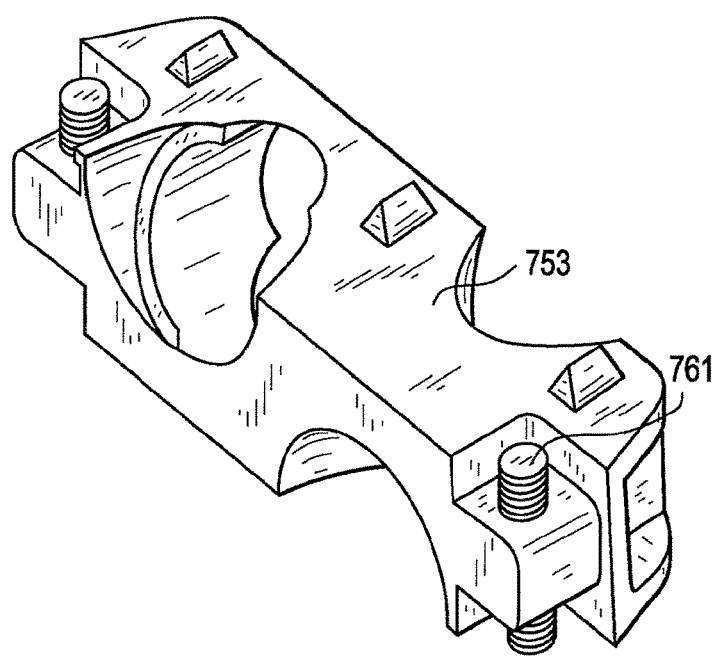
FIG. 10 discloses pins received within the interlocking features of the anterior wall.

FIG. 10 discloses how pins 761 are received within the tongue features of the anterior wall 753.

Figure 11:
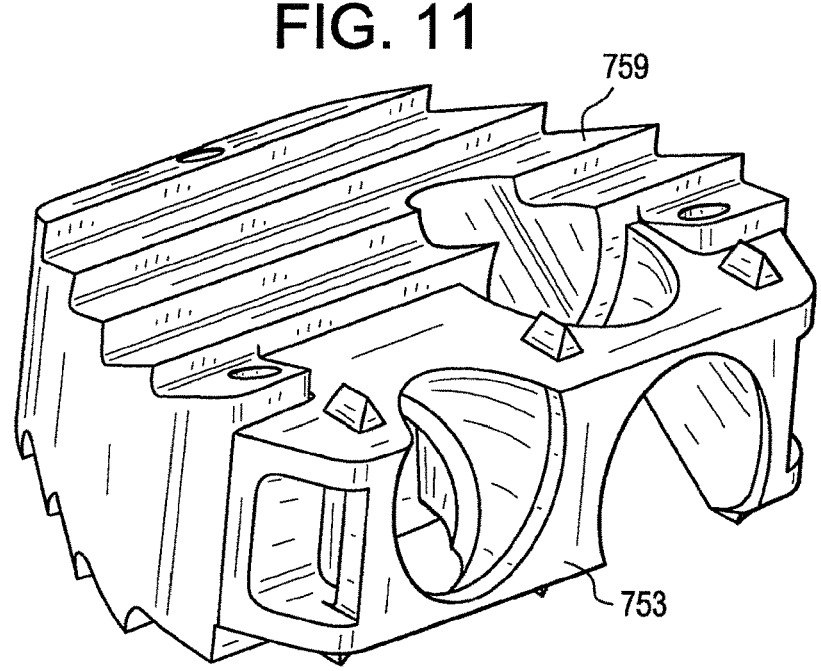
FIG. 11 discloses an embodiment of the present invention wherein the integral body comprises allogenic bone.

FIG. 11 discloses an embodiment of the present invention wherein the spacer comprises an anterior wall 753 connected to an integral body 759, wherein the integral body is substantially solid and comprises the two side walls and a posterior wall, and is made of allogenic bone.

Figure 12A:
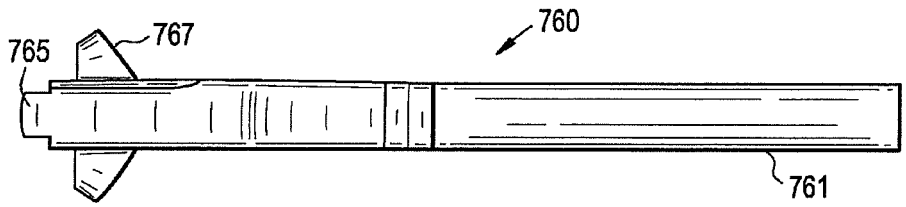
FIGS. 12A-C disclose an inserter tip of the present invention.
Figure 12B:
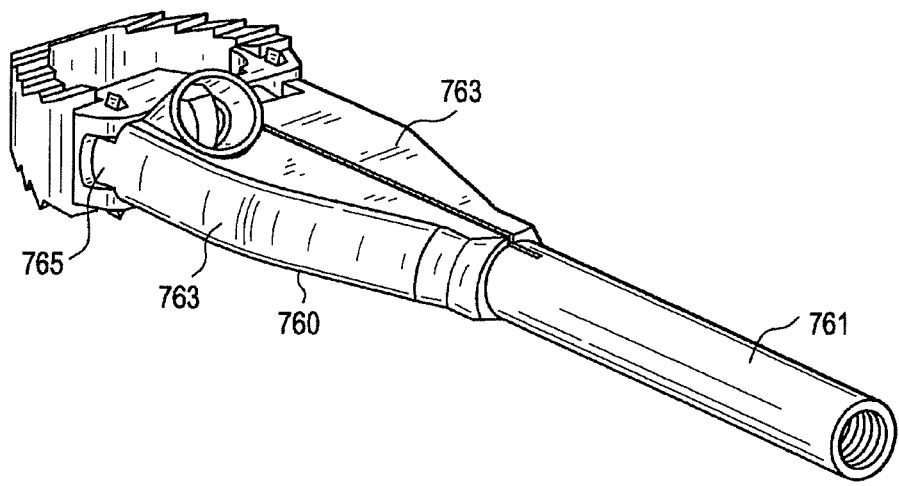
Figure 12C:
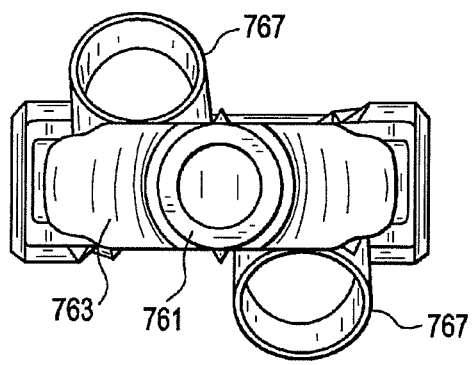

FIGS. 12A-C disclose an inserter tip 760 of the present invention. The inserter tip comprises a proximal barrel 761 forming two distal tynes 763. Each tyne has an attachment feature 765 for grabbing the implant and an annulus 767 for receiving a bone screw.

Eighth Aspect of the Invention

Conventional cervical cages are typically held in place by the use of a plate that is anchored into the adjacent vertebrae by screws. However, certain cervical intervertebral fusion cages have angled screw holes that allow anchoring screws to enter the cage and anchor into the vertebrae without the use of a plate. These cages are often referred to as "stand alone" cages. Eliminating the plate beneficially results in a lower-profile implant, fewer implant components, and a lower cost. However, it is important that the stand alone cage possess a screw retention mechanism that prevents the inserted screws from backing out of the cage, which may cause loosening of the cage or even perforation of the esophagus.

Figure 13A:
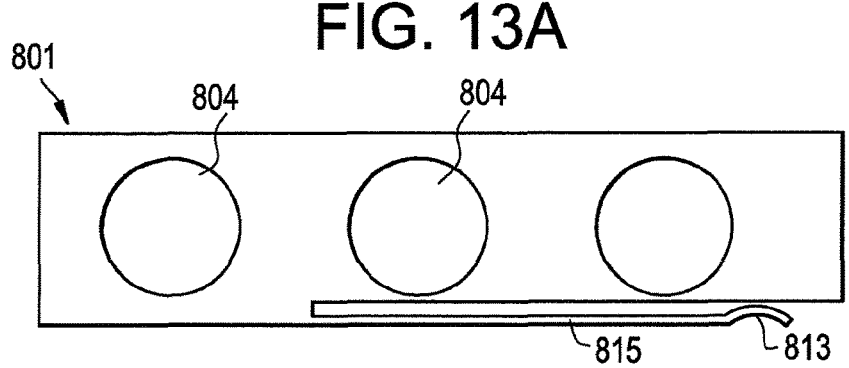
FIGS. 13A-D disclose front views of an embodiment of the present invention including a retaining plate, and components thereof FIGS. 14A-15B disclose top views of a retaining plate embodiment of the present invention including a living spring, and components thereof FIG. 16 discloses a front view of a retaining plate embodiment of the present invention including a living spring and a chamfered insertion feature.
Figure 13B:
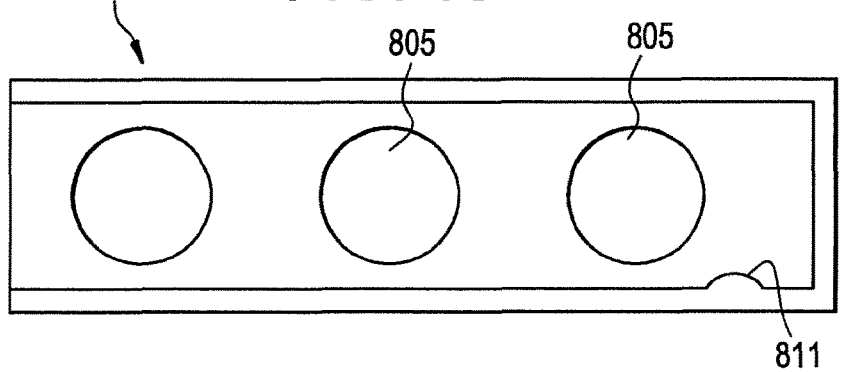
Figure 13C:
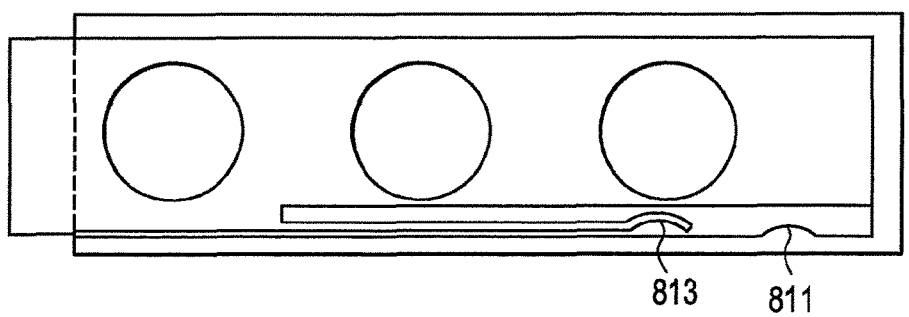
Figure 13D:
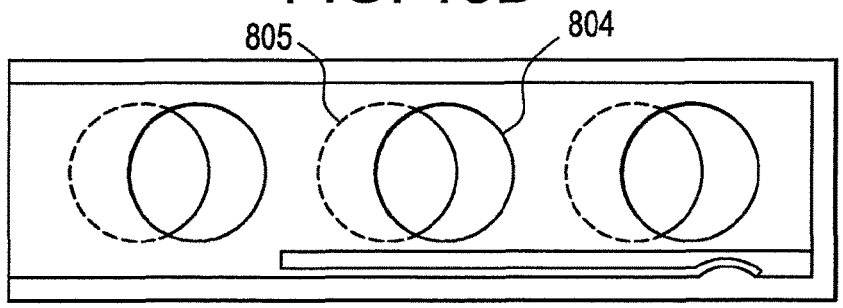
Figure 14A:
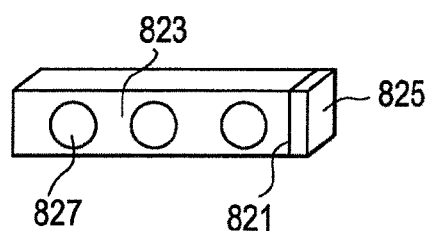
Figure 15A:
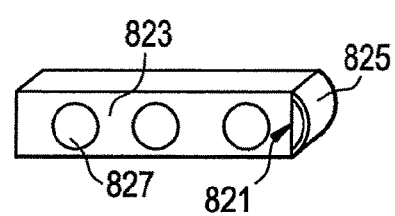
Figure 14B:
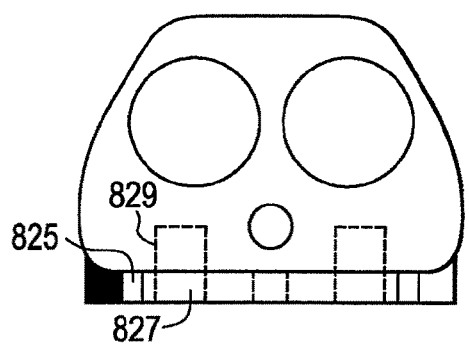
Figure 15B:
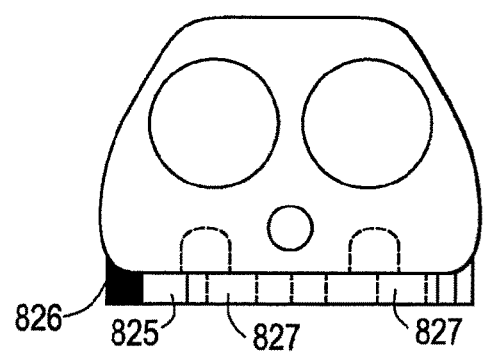

The present invention comprises a retaining element that retains these anchoring screws within the cage. It preferably includes an additional component, namely a retaining plate 801, which is shown by itself in FIG. 13A. The retaining plate is slidably mounted on the anterior face 803 of the cage, which is shown by itself in FIG. 13B. The assembly of the retaining plate upon the anterior face of the cage is shown in FIGS. 13C and 13D. This plate can be slidably mounted to the cage using conventional mounting mechanisms such as a dovetail or track. The retaining plate comprises several through-holes 804—one for each screw hole 805 provided in the cage. The cage could be inserted with the plate holes misaligned with the holes of the cage. In this condition, the plate is in its "retain" or "closed" position. After insertion, the plate is translated into an "open" position whereby the holes in the plate are aligned with the holes in the cage, as in FIG. 13C. This is the position for screw insertion. The anchor screws are then inserted through the aligned holes in the retaining plate and cage so that they anchor the cage into the vertebrae. Finally, the plate is translated into its "retain" position (of FIG. 13D) so that the through-holes of the plate are again misaligned with the screw holes of the cage. The misalignment of the screw holes prevents the screws from backing out of the cage.

Therefore, in accordance with the present invention, there is provided an intervertebral device for insertion into a disc space defined by opposing vertebral endplates, comprising:
i) an intervertebral spacer comprising:
   a) an anterior wall having an upper surface and a lower surface, an anterior surface, and a first hole extending from the anterior surface to the upper surface and a second hole extending from the anterior surface to the lower surface,
   b) a posterior wall having an upper surface and a lower surface, and
   c) first and second side walls connecting the anterior and posterior walls, each side wall having an upper surface and a lower surface,
ii) a first screw received in the first hole and having a distal tip, an intermediate shaft having a first thread, and a proximal head, and
iii) a retaining plate slidably mounted to the anterior surface of the spacer in a first and a second slidable position, the plate having first and second holes,
wherein, in the first slidable position, the first hole of the plate aligns with the first hole of the spacer to allow passage of the screw therethrough, and
wherein, in the second slidable position, the first hole of the plate mis-aligns with the first hole of the spacer to prevent back out of the screw.

Additionally, mechanisms can be provided that prevent the plate from post-operatively moving back to its initial open position. Some such mechanisms direct engagement of components in the medial-lateral direction (as in FIGS. 13C and 13D), while other direct engagement of components in the anterior-posterior direction.

In some embodiments, as in FIGS. 13A-D, a protrusion-type locking feature 811 on the anterior surface of the cage engages a mating recess 813 on a locking arm 815 on the plate, thereby preventing the plate from returning to the "open" position. This locking mechanism could be provided via a number of different embodiments, including features that move in a medial-lateral or anterior-posterior direction to produce the desired locking.

For example, in a first (medial-lateral) embodiment, and now referring to FIGS. 13A-D, a protruding mating feature 811 provided on the anterior face of the cage moves laterally to engage a recessed mating feature 813 provided on the plate when the device is in its "retain" position, thereby preventing the plate from returning to the "open" position.

Typically, one of these features is provided as a flexible or spring-like element so that the mating features snap into place, thereby locking the relative positions of the plate and cage. These mating features can also be designed to index the plate between "open" and "retain" positions. In some embodiments thereof, the protrusion can be provided at the end of a flexible arm that moves laterally across the plate to engage the recess. Alternatively, a recessed mating feature provided on the anterior face of the cage could engage a protruding mating feature provided on the plate when the device is in its "retain" position, again locking the relative positions of the plate.

In a second (anterior-posterior) embodiment, a moveable protrusion (such as a ball detent) is mounted in the cage to move in the A/P direction and engage a recess in the plate, again indexing the plate in the two positions. Alternatively, a locking arm cut into the locking plate with a deflection direction in the A/P direction could engage with a recess cut into the cage.

In one method of using the present invention, the plate-cage assembly is first loaded into the disc space. The insertion instrument used for cage insertion and screw placement has an additional mechanism that laterally slides the plate over the anterior surface of the cage. When the plate is slid into "open" position, screws are inserted therethrough. When the plate is then slid into "retain" position, the holes in the plate and cage mis-align, thereby preventing the screws from backing out.

Therefore, in some embodiments, the plate is slidable in a medial-lateral direction across the anterior face of the spacer, while in others the plate is slidable in an upper-lower direction across the anterior face of the spacer.

In some embodiments, the spacer and plate include a locking feature to retain the holes in a mis-aligned state. Preferably, the locking feature comprises a locking arm or a ball detent. In some embodiments, the locking feature locks in a medial-lateral direction, while in others the locking feature locks in an anterior-posterior direction, and in still others the locking feature locks in an upper-lower direction.

In some embodiments, the locking feature comprises a protrusion and a recess.

In another embodiment, and now referring to FIGS. 14A-15B, a sidewall 821 of the retaining plate 823 is equipped with a living spring 825. This plate is adapted to slidably engage a pair of parallel rails (not shown) extending laterally across the anterior face of the cage. The lateral movement of the plate is arrested by stop 826. The placement of through-holes 827 on the plate is predetermined so that a) the plate through-holes align with the screw holes 829 of the cage when the plate is biased so as to fully compress the spring (as in FIG. 14B), and b) the plate through-holes mis-align with the screw holes of the cage when the bias is released so as to allow expansion of the spring (as in FIG. 15B).

Figure 16:
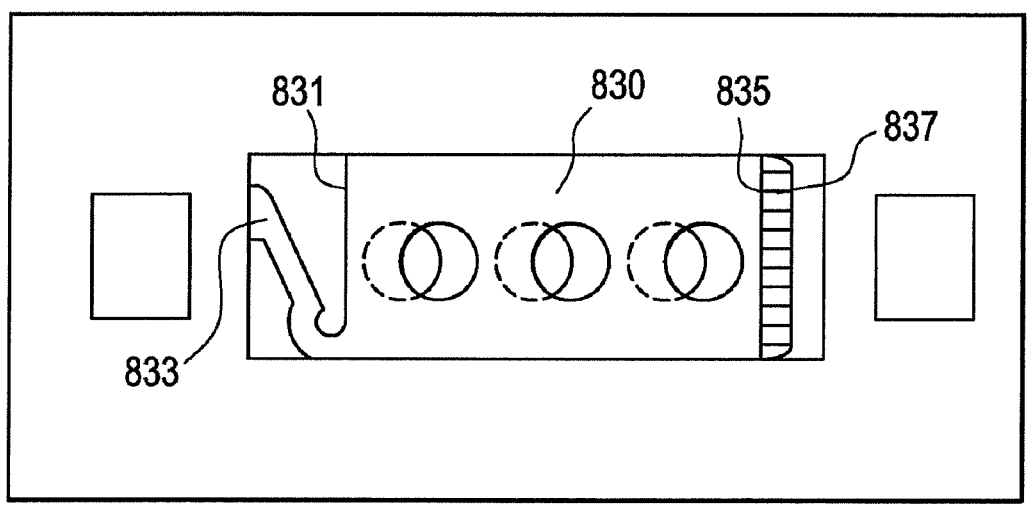
Figure 17:
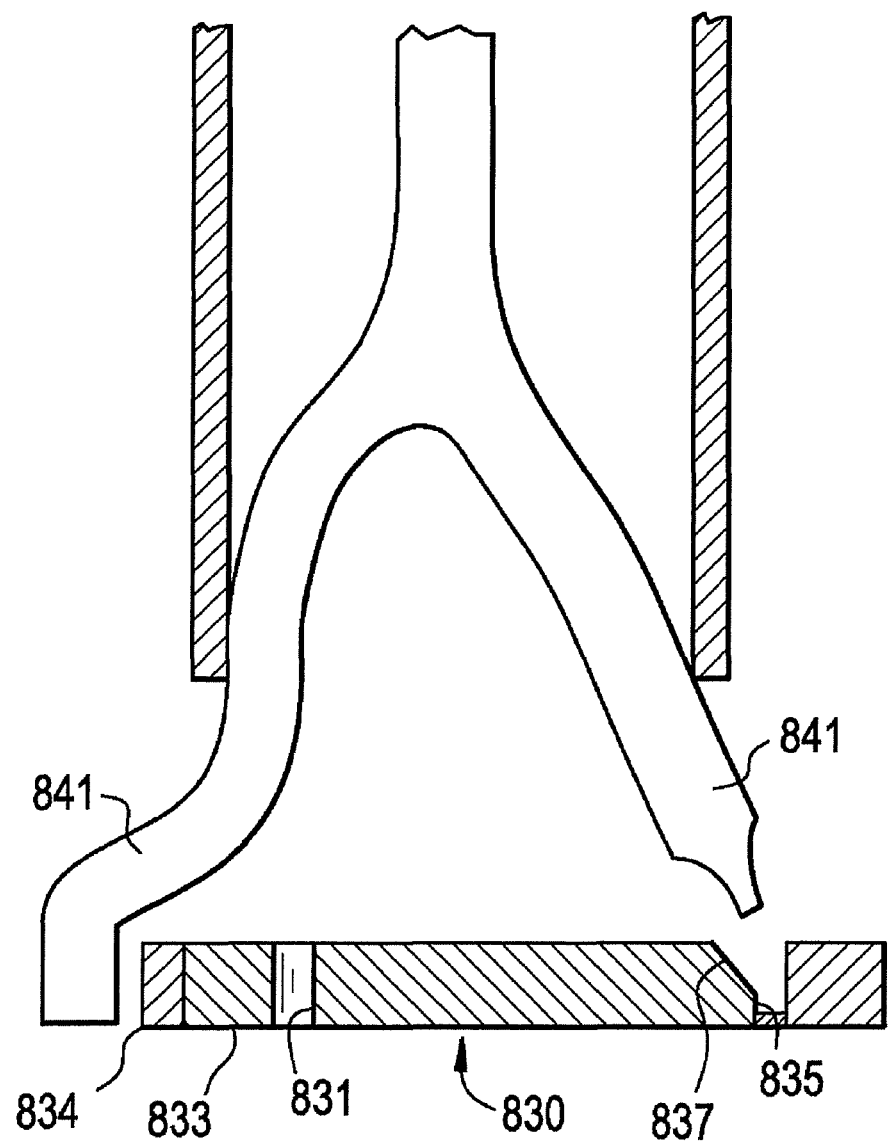
FIG. 17 discloses an inserter instrument engaged with a retaining plate of the present invention.

FIG. 16 presents another embodiment of a plate 830 having a sidewall 831 equipped with a "living spring" 833. The opposing sidewall 835 of the plate has a chamfer feature 837 that mates with a chamfered surface on a grabber instrument. In using this embodiment of FIG. 16, and now referring to FIG. 17, the device is typically installed with the plate in its unbiased position. Prior to inserting screws into the cage, opposed jaws 841 of a grabber instrument are placed about the device to contact the chamfered surface 837 of the plate and a sidewall 834 of the cage. The grabber instrument is then actuated so that its jaws 841 are compressed so as to compress the spring 833. In this biased position, the holes are aligned and screws can be inserted therethrough into the cage. Upon insertion, the jaws of the grabber can be released so as to release the bias from the spring and return the plate to its former position in which the holes are mis-aligned, thereby preventing screw backout.

In other embodiments, the living spring is replaced with a stand-alone compression spring or leaf spring.

Figure 18:
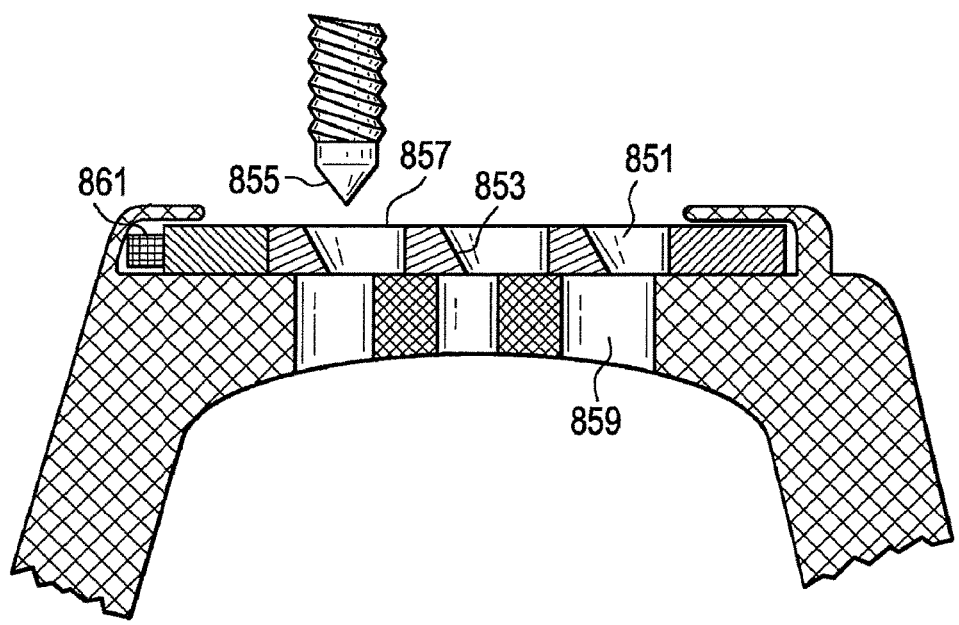
FIG. 18 discloses a chamfered retaining plate and cage (partial) of the present invention.
Figure 19A:
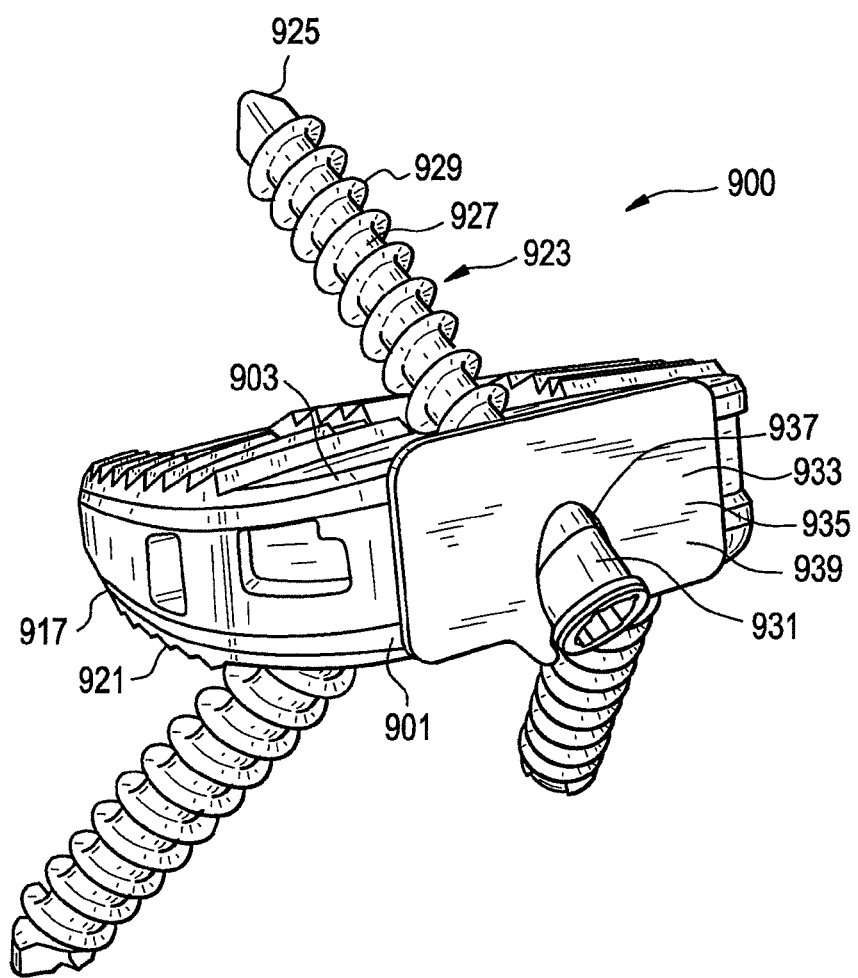
FIGS. 19A-C, 20 and 21 disclose different views of a fixation cage with a secondary washer for insertion into a disc space.
Figure 19B:
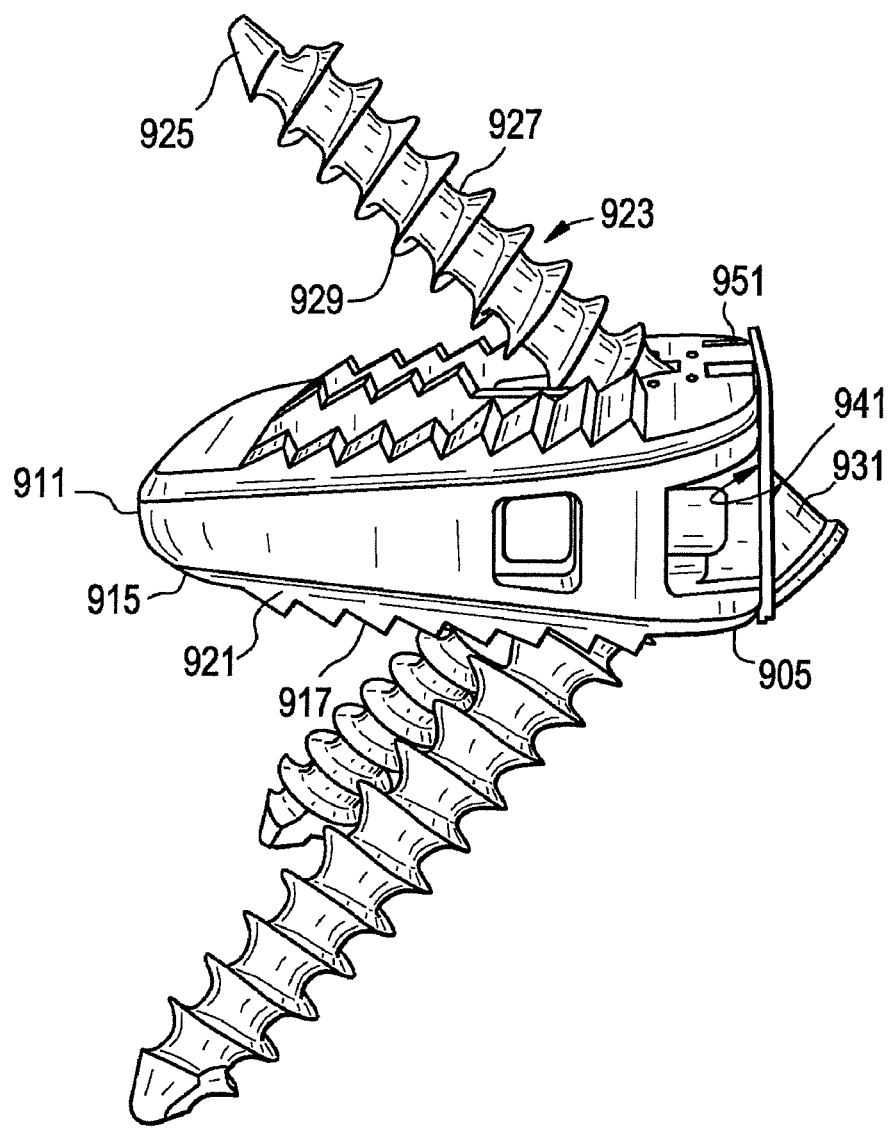
Figure 19C:
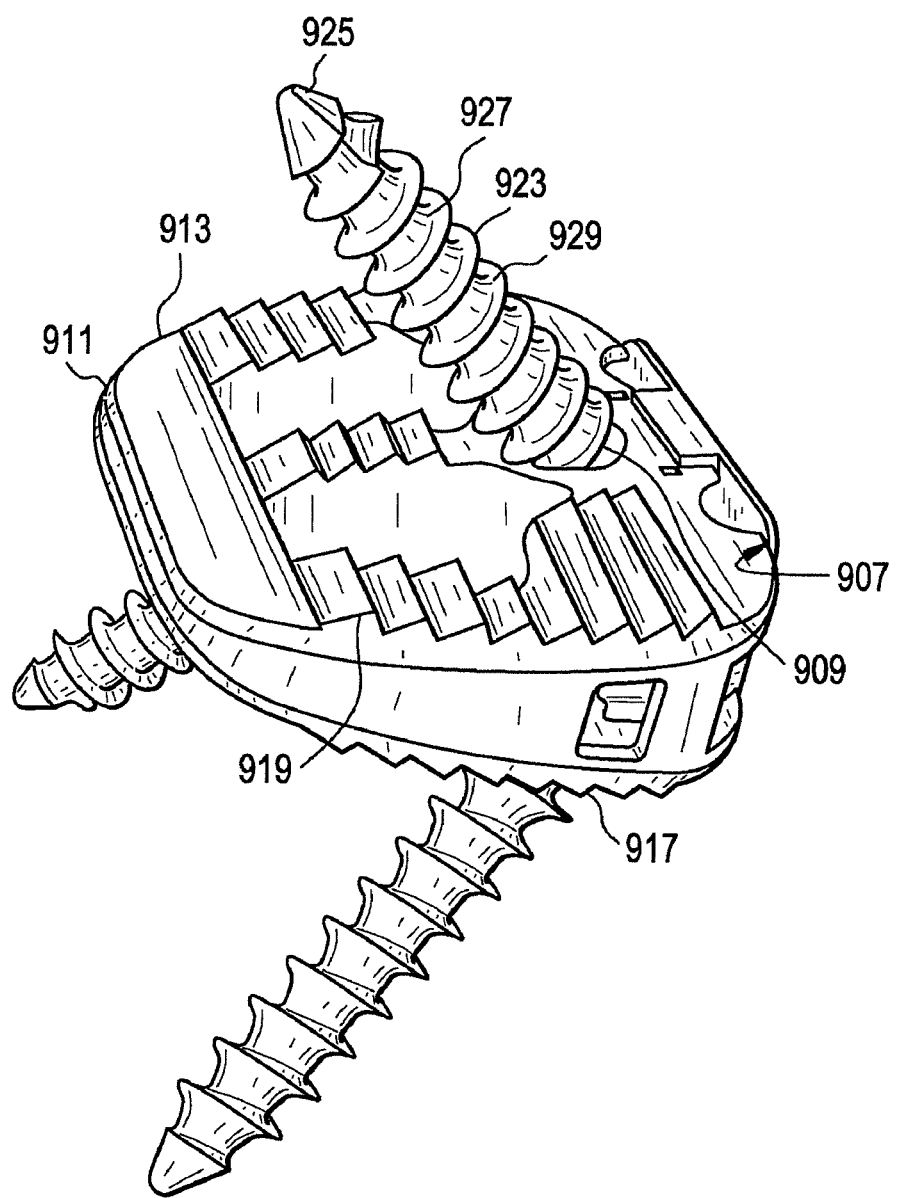
Figure 20:
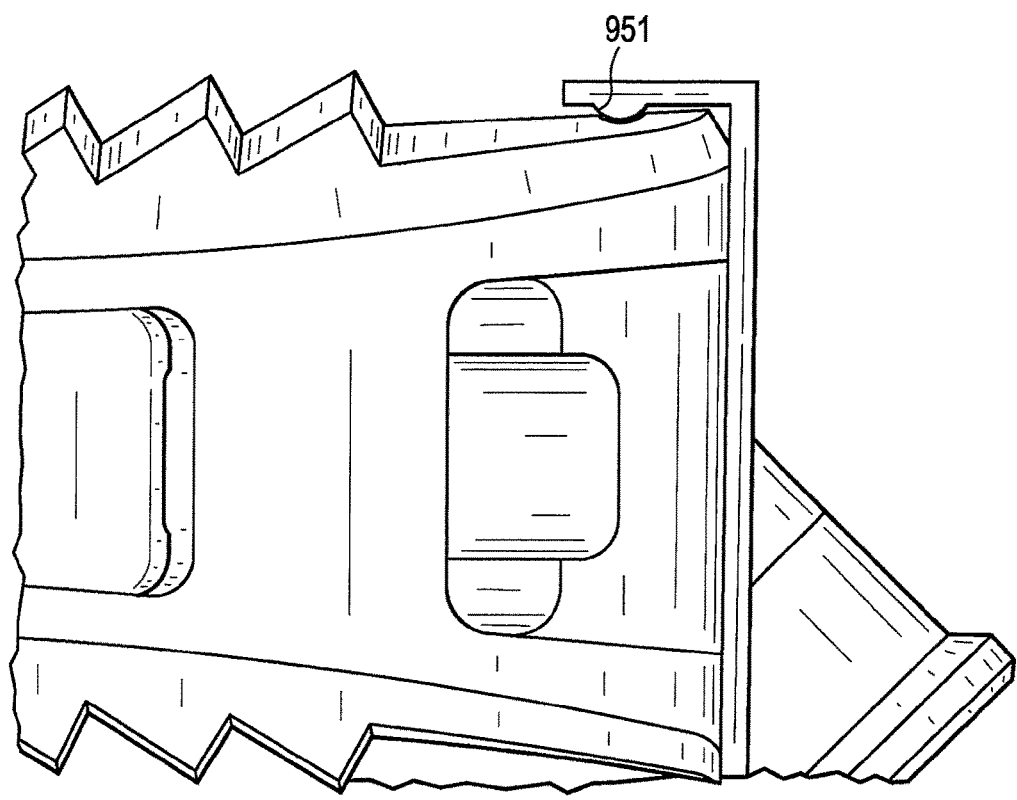
Figure 21:
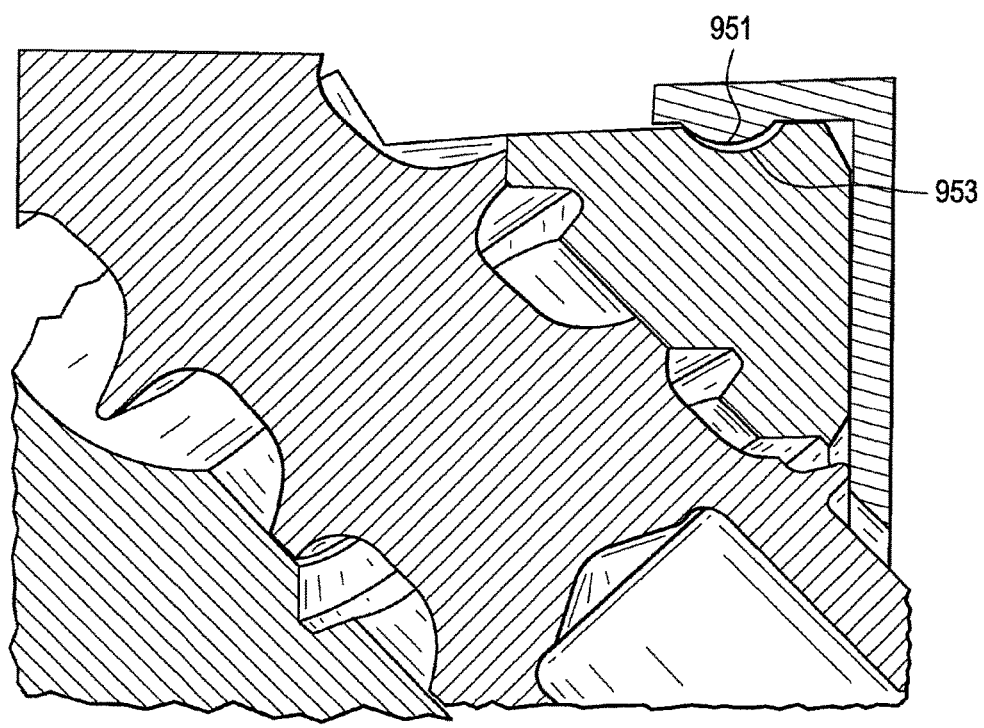

In another embodiment, and now referring to FIG. 18, the plate may be altered so as to eliminate the need for the grabber instrument discussed above. In this embodiment, the through-holes 851 of the plate are provided with unilateral chamfers 853 that mate with the distal tip 855 of the screw being inserted. Continued insertion of the tip into the through-hole causes spring 861 to compress and plate 857 to slide laterally, and thereby align the holes of the plate with the holes 859 of the cage. Once the head of the screw passes the chamfered hole of the plate, the living spring component 861 of the plate expands so as to cause mis-alignment of the holes, thereby preventing screw back-out.

Therefore, in accordance with the present invention, the plate further comprises first and second sidewalls, wherein the first sidewall comprises a living spring. In some embodiments thereof, the second sidewall of the plate comprises a feature (preferably, a chamfer) for mating with a grabber instrument. In other embodiments, the holes of the plate comprise chamfers adapted to mate with the distal tip of the screw.

Ninth Aspect of the Invention

Prior art references related to a fixation cage with a secondary washer include: U.S. Patent Publication 2010-0057206; U.S. Patent Publication 2009-0088849; U.S. Patent Publication 2010-0145459; U.S. Pat. Nos. 6,730,127; 7,662,182; 6,972,019; U.S. Patent Publication 2008-0249569; U.S. Patent Publication 2009-0105831; U.S. Pat. Nos. 7,306,605; 7,288,094; U.S. Patent Publication 2010-0312345; U.S. Patent Publication 2010-0286777; U.S. Pat. No. 6,945,973; U.S. Patent Publication 2010-0106249; U.S. Pat. Nos. 6,849,093; 6,984,234; U.S. Patent Publication 2009-0105830; U.S. Patent Publication 2009-0210062; U.S. Pat. Nos. 7,674,279; 7,452,370; 6,558,423; 6,890,335; 6,629,998.

Conventional fixation cages have several means for capturing angled bone-engaging screws and ensuring that those screws do not back out. Conventional anti-backout mechanisms include assembled rotating cover plates, cams, bushings, expanding screws, and set screws. One particular anti-backout means is a secondary cover plate that either snaps onto the cage itself or is docked to the cage and secured to the cage faceplate using additional hardware, such as a screw. This secondary cover plate can fully or partially cover the most proximal portion of the screw head and could in theory prevent any screw backout.

As noted above, FIGS. 5C-E, supra, describe some embodiments utilizing a particular anti-backout mechanism in which the proximal end portion of the screwthread has a parallel sidewall. Once the screw is threaded into position so that the entire threadform has passed over the ring, the distal portion of the screw head proximally abuts the ring, thereby preventing further advance. In addition, if the screw were to begin backout, the last turn of the screw thread (i.e., the proximal end portion of the thread having the parallel sidewall) would soon abut against the ring, thereby preventing backout.

In the present invention, the ring is replaced by a stand-alone washer positioned anterior to the screw hole.

There is no known secondary washer and/or plate in the field of anterior cervical fusion that attaches to the fixation screw (and not directly to the cage). Such a washer could float approximately around the neck of the screw or be integral with the head of the screw. This washer would cover one or more of the other angled fixation screws, thus preventing screw backout.

Thus, if a device possesses the above-discussed lag features in the screw and the helical feature in the bore of the cage, the device may further comprise a secondary washer. The purpose of the secondary washer is to further resist screw backout.

The secondary washer may preferably be loosely attached to the proximal shaft of a final fixation screw. The screw-washer combination is the last item added to the cage construct to complete the device assembly. The washer is designed to float in a predetermined zone of the fixation screw distal of the screw head, and ideally would be removed only with special equipment.

Therefore, and now referring to FIGS. 19A-C, 20 and 21, there is provided an intervertebral device for insertion into a disc space defined by opposing vertebral endplates, comprising:

i) an intervertebral spacer 900 comprising:
   a) having an anterior wall 901 having an upper surface 903 and a lower surface 905, an anterior surface 907, and a first screwhole 909 extending from the anterior surface to the upper or lower surface of the anterior wall,
   b) a posterior wall 911 having an upper surface 913 and a lower surface 915, and
   c) first and second side walls 917 connecting the anterior and posterior walls, each side wall having an upper surface 919 and a lower surface 921,
ii) a first screw 923 received in the first screwhole and having a distal tip 925, an intermediate shaft 927 having a first thread 929, and a proximal head 931,
iii) a washer 933 having a body portion 935, an aperture 937, a proximal face 939 and a distal face 941, the washer positioned anterior to the anterior face so that its aperture aligns with the first screwhole;
wherein the shaft of the screw is received in the aperture of the distal washer.

The washer is designed to seat on the anterior (proximal) face of the anterior wall of the cage, against the region of the wall surrounding the corresponding screw-hole. It may be held in place by a snap clip feature 951 and corresponding recess 953 residing on the upper or lower face of the cage (shown in FIGS. 20 and 21).

Figure 22:
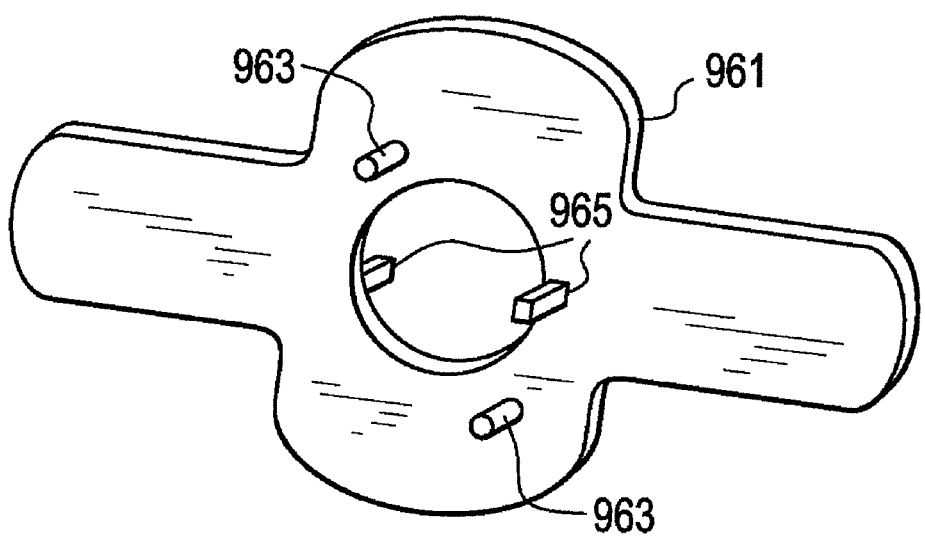
FIG. 22 depicts a washer configured to be seated in a recess in an anterior portion of a fixation cage.

In some embodiments, the washer further comprises design features that abut corresponding features in the cage to ensure proper positioning upon final seating. In one such embodiment, as in FIG. 22, the periphery of the washer has a contour 961 that matches and seats in a recess in the anterior portion of the cage.

In some embodiments, the design features may resist washer rotation. In one such embodiment, the distal face of the washer has at least one projection 963 that matches and seats in a corresponding recess in the anterior face of the cage.

In another embodiment, the proximal or distal face of the washer has at least one projection 965 that serves to interrupt screw backout.

Also, in some embodiments, the washer comprises screw engagement features. Upon the fixation screw's final rotation, the screw will pass through the aperture in the washer at an angled trajectory. Features of the washer surrounding the aperture could engage features of the screw in its final degrees of rotation so as to prevent easy counter-clockwise removal of the screw.

When the washer is integral with the screw head, the head comprises at least one flange (i.e., the washer) extending therefrom, the flange having a proximal face and a distal face.

We claim:

1. An intervertebral fusion device comprising:
   i) an intervertebral cage including;
      a) upper and lower surfaces that are spaced from each other along a first direction and are configured to engage respective vertebral bodies;
      b) a proximal wall that defines a proximal surface;
      c) a distal wall opposite the proximal wall, and
      d) first and second side walls connected between the proximal and distal walls, wherein the proximal surface defines a center that is equidistantly spaced from the first and second side walls; and
   ii) a plate that defines a through-hole extending therethrough, wherein the plate is slidable along the proximal surface of the intervertebral cage along a direction of sliding that lies in a plane that is perpendicular to the first direction; and
   iii) a screw received by the through-hole of the plate, wherein the intervertebral cage defines a hole that extends into the proximal wall, and when the screw extends into the hole of the intervertebral cage, the plate is configured to be disposed in a position whereby 1) the through-hole of the plate is offset in its entirety from the center along the plane so as to define a gap between the through-hole and the center along the plane, 2) a first portion of the hole is aligned with the through-hole of the plate, and 3) a second portion of the hole is offset from the through-hole of the plate along the plane, the second portion of the hole being different than the first portion of the hole,
   wherein the plane extends through both the through-hole of the plate and a central location of the hole of the intervertebral cage, the central location of the hole being centrally disposed in the hole with respect to the first direction.

2. The intervertebral fusion device as recited in claim 1, wherein the proximal and distal walls are spaced from each other along a second direction perpendicular to the first direction, and the plate is slidable along the proximal surface of the intervertebral cage such that an opening to the through-hole is movable from a first position to a second position that is offset with respect to the first position along a third direction that is perpendicular to each of the first and second directions, the opening disposed at a surface of the plate that faces the proximal surface of the intervertebral cage.

3. The intervertebral fusion device as recited in claim 1, wherein an opening to the through-hole defines a circle.

4. The intervertebral fusion device as recited in claim 3, wherein the plate is translatably coupled to the intervertebral cage via a track.

5. The intervertebral fusion device as recited in claim 4, wherein the track is linear.

6. The intervertebral fusion device as recited in claim 1, wherein the plate retains the screw in the intervertebral cage.

7. The intervertebral fusion device as recited in claim 6, wherein the plate prevents the screw from backing out of the intervertebral cage.

8. The intervertebral fusion device as recited in claim 7, wherein the screw is elongate along a central axis, and a portion of the plate overlaps a portion of the screw along a direction that is parallel to the central axis, so as to prevent the screw from backing out of the intervertebral cage.

9. The intervertebral fusion device as recited in claim 8, wherein the screw defines a screw head and a distal tip spaced from the screw head along the central axis, and the portion of the plate defines a surface that is disposed between the distal tip of the screw and the proximal surface with respect to the direction that is parallel to the central axis.

10. The intervertebral fusion device as recited in claim 1, wherein the screw is configured to engage an instrument that is received by the through-hole, so as to drive the screw to rotate.

11. The intervertebral fusion device as recited in claim 1, wherein the screw is externally threaded.

12. The intervertebral fusion device as recited in claim 1, wherein each of the upper and lower surfaces define teeth configured to grip the respective vertebral bodies.

13. The intervertebral fusion device as recited in claim 1, wherein the proximal and distal walls are spaced from each other along a second direction perpendicular to the first direction, the plate is slidable along the proximal surface of the intervertebral cage such that the second portion of the hole is offset with respect to the through-hole along a third direction that is perpendicular to each of the first and second directions.

14. The intervertebral fusion device as recited in claim 1, wherein a cross-section of the through-hole defines a circle.

15. The intervertebral fusion device as recited in claim 1, wherein the plane further passes through a central location of the through-hole of plate, the central location of the through-hole being centrally disposed with respect to the first direction.

16. The intervertebral fusion device as recited in claim 1, wherein the through-hole of the plate has a perimeter that is enclosed by the plate.

17. An assembly comprising:
the intervertebral fusion device as recited in claim 1; and
a second screw, the second screw having a threaded shaft configured to be driven into one of the upper and lower vertebral bodies.

18. The assembly as recited in claim 17, further comprising a third screw, the third screw having a threaded shaft configured to be driven into one of the upper and lower vertebral bodies.

19. An intervertebral fusion device comprising:
i) an intervertebral cage including;
a) a proximal wall that defines a proximal surface that extends from a first side of the intervertebral cage to a second side of the intervertebral cage such that the proximal surface defines a center that is equidistantly spaced from the first and second sides of the intervertebral cage, wherein the intervertebral cage defines a hole that extends into the proximal wall, the hole has an opening at the proximal surface, and the proximal surface defines a fully enclosed perimeter of the opening;
b) a distal wall opposite the proximal wall,
c) first and second side walls disposed at the first and second sides, respectively, and connected between the proximal and distal walls; and
d) upper and lower surfaces that are spaced from each other along a first direction and are configured to engage respective upper and lower vertebral bodies that define the intervertebral space; and ii) a plate that defines a through-hole extending therethrough, wherein the through-hole is fully enclosed by a perimeter, an entirety of the perimeter is defined by the plate, and the plate is slidable along the proximal surface of the intervertebral cage along a direction of sliding that lies in a plane that is perpendicular to the first direction; and
iii) a screw received by the through-hole of the plate along a screw direction,
wherein the intervertebral fusion device is configured to be fully implanted in an intervertebral space such that 1) the through-hole of the plate is offset in its entirety from the center, 2) a first portion of the hole is aligned with the through-hole of the plate along the screw direction, and 3) a second portion of the hole is offset from the through-hole of the plate along the direction of sliding, the second portion of the hole being different than the first portion of the hole, and
wherein the plane extends through both the through-hole of the plate and a central location of the hole of the intervertebral cage, the central location of the hole being centrally disposed in the hole with respect to the first direction.

20. The intervertebral fusion device as recited in claim 19, wherein the proximal and distal walls are spaced from each other along a second direction perpendicular to the first direction, and the plate is slidable along the proximal surface of the intervertebral cage such that an opening to the through-hole is movable from a first position to a second position that is offset with respect to the first position along a third direction that is perpendicular to each of the first and second directions, the opening to the through-hole disposed at a surface of the plate that faces the proximal surface of the intervertebral cage.

21. The intervertebral fusion device as recited in claim 19, wherein an opening to the through-hole defines a circle.

22. The intervertebral fusion device as recited in claim 21, wherein the plate is translatably coupled to the intervertebral cage via a track.

23. The intervertebral fusion device as recited in claim 22, wherein the track is linear.

24. The intervertebral fusion device as recited in claim 19, wherein the plate retains the screw in the intervertebral cage.

25. The intervertebral fusion device as recited in claim 24, wherein the plate prevents the screw from backing out of the intervertebral cage.

26. The intervertebral fusion device as recited in claim 25, wherein the screw is elongate along a central axis, and a portion of the plate overlaps a portion of the screw along a direction that is parallel to the central axis, so as to prevent the screw from backing out of the intervertebral cage.

27. The intervertebral fusion device as recited in claim 19, wherein the screw is configured to engage an instrument that is received by the through-hole, so as to drive the screw to rotate.

28. The intervertebral fusion device as recited in claim 19, wherein the screw is externally threaded.

29. The intervertebral fusion device as recited in claim 19, wherein the proximal and distal walls are spaced from each other along a second direction perpendicular to the first direction, the plate is slidable along the proximal surface of the intervertebral cage such that the second portion of the hole is offset with respect to the through-hole along a third direction that is perpendicular to each of the first and second directions.

30. The intervertebral fusion device as recited in claim 19, wherein the screw is further received in the hole of the intervertebral cage.

31. The intervertebral fusion device as recited in claim 19, wherein a cross-section of the through-hole defines a circle.

32. An assembly comprising:
   the intervertebral fusion device as recited in claim 19; and
   a second screw, the second screw having a threaded shaft configured to be driven into one of the upper and lower vertebral bodies.

33. The assembly as recited in claim 32, further comprising a third screw, the third screw having a threaded shaft configured to be driven into one of the upper and lower vertebra.

* * * * *